United States Patent
Kiprov

(10) Patent No.: US 12,005,172 B2
(45) Date of Patent: Jun. 11, 2024

(54) COMPOSITIONS AND METHODS FOR PLASMAPHERESIS

(71) Applicant: Lyfspn, Inc., Menlo Park, CA (US)

(72) Inventor: Dobri Kiprov, Menlo Park, CA (US)

(73) Assignee: LYFSPN, INC., Menlo Park, CA (US)

( * ) Notice: Subject to any disclaimer, the term of this patent is extended or adjusted under 35 U.S.C. 154(b) by 0 days.

(21) Appl. No.: 18/204,293

(22) Filed: May 31, 2023

(65) Prior Publication Data

US 2023/0380687 A1    Nov. 30, 2023

Related U.S. Application Data

(60) Provisional application No. 63/347,124, filed on May 31, 2022.

(51) Int. Cl.
*A61M 1/34* (2006.01)
*A61B 5/00* (2006.01)
*A61B 5/11* (2006.01)

(52) U.S. Cl.
CPC ......... *A61M 1/3496* (2013.01); *A61B 5/0022* (2013.01); *A61B 5/1118* (2013.01); *A61B 5/1122* (2013.01); *A61B 5/1114* (2013.01)

(58) Field of Classification Search
CPC ... A61B 5/0022; A61B 5/1118; A61B 5/1122; A61B 5/1114; A61M 1/3496
See application file for complete search history.

(56) References Cited

U.S. PATENT DOCUMENTS

| | | |
|---|---|---|
| 10,391,223 B2 | 8/2019 | Rosa-Bray et al. |
| 2008/0040153 A1 | 2/2008 | Davis |
| 2015/0153357 A1 | 6/2015 | Darashkevich et al. |
| 2019/0151360 A1 | 5/2019 | Eliaz |
| 2020/0215348 A1 | 7/2020 | Maharaj |
| 2020/0347461 A1 | 11/2020 | Horvath et al. |
| 2022/0047680 A1 | 2/2022 | Grifols Roura et al. |
| 2022/0105354 A1 | 4/2022 | Maharaj |
| 2022/0163526 A1 | 5/2022 | Macip |
| 2023/0072523 A1 | 3/2023 | Glozman |

OTHER PUBLICATIONS

Chen et al., J. Neurology (2011), vol. 258, pp. 1240-1246.*
Al-Ahmer I., et al., "Determinants of Quality of Life Changes with Plasmapheresis in Patients with Myasthenia Gravis," The Egyptian Journal of Neurology, Psychiatry and Neurosurgery, 2021, vol. 57:65, 10 pages.
Bobati S., et al., "Therapeutic Plasma Exchange—An Emerging Treatment Modality in Patients with Neurologic and Non-Neurologic Diseases," Journal of Clinical and Diagnostic Research, Aug. 2017, vol. 11, No. 8, pp. EC35-EC37.

(Continued)

*Primary Examiner* — John Kim
(74) *Attorney, Agent, or Firm* — DLA Piper LLP; Melissa M. Harwood

(57) ABSTRACT

Described herein are compositions and methods for performing plasmapheresis. The compositions and methods for performing plasmapheresis are innovative at least in their application towards the treatment and prevention of aging and conditions associated with aging. Plasmapheresis compositions and methods described herein are directed towards reducing or eliminating conditions associated with aging.

12 Claims, 23 Drawing Sheets

(56) References Cited

OTHER PUBLICATIONS

Drusini A.G., et al. "One-Leg Standing Balance and Functional Status in an Elderly Community-Dwelling Population in Northeast Italy," Aging Clin. Exp. Res., 2002, vol. 14, pp. 42-46.

International Search Report and Written Opinion for Application No. PCT/US2023/024058, dated Oct. 5, 2023, 12 Pages.

Pieper B., et al., "A Comparative Study of the Five-Times-Sit-to-Stand and Timed-Up-and-Go Tests as Measures of Functional Mobility in Persons with and without Injection-Related Venous Ulcers," Advances in Skin and Wound Care 2014, vol. 27, No. 2, pp. 82-92.

Adav S.S., et al., "Metabolomics Signatures of Aging: Recent Advances," Review, Aging and Disease, Apr. 2021, vol. 12(2), pp. 646-661.

Boada et al., A randomized, controlled clinical trial of plasma exchange with albumin replacement for Alzheimer's disease: Primary results of the AMBAR study. Alzheimer's Dement 16: 1412-1425 (2020).

Bouatra S., et al., "The Human Urine Metabolome," PLOS One, vol. 8(9), Sep. 4, 2013, 28 pages.

Campisi J., "Aging, Cellular Senescence, and Cancer," Annual Review of Physiology, 2013, vol. 75, pp. 685-705.

Chen C-R., et al., "Antibodies to Thyroid Peroxidase Arise Spontaneously with Age in NOD.H-2h4 Mice and Appear After Thyroglobulin Antibodies," Endocrinology, Sep. 2010, vol. 151(9), pp. 4583-4593.

Chia C.W., et al., "Age-related Changes in Glucose Metabolism, Hyperglycemia, and Cardiovascular Risk," Circulation research, Sep. 14, 2018, vol. 123(7), pp. 886-904.

Crisp H.C., et al., "Quantitative Immunoglobulins in Adulthood," Allergy and asthma proceedings, vol. 30(6), Nov.-Dec. 2009, pp. 649-654.

Czarnocka B., et al., "In Old Age the Majority of Thyroid Peroxidase Autoantibodies are Directed to a Single TPO Domain Irrespective of Thyroid Function and Iodine Intake," Clinical Endocrinology, 1998, vol. 48, pp. 803-808.

Dehal H., et al., "Total Plasma Exchange in Hypertriglyceridemia-Induced Pancreatitis: Case Report and Literature Review," Case Reports in Medicine, vol. 2018, 2018, 3 pages.

Dimri G.P., et al., "A Biomarker that Identifies Senescent Human Cells in Culture and in Aging Skin in vivo," Cell Biology, Proceedings of the National Academy of Sciences of the United States of America, vol. 92, Sep. 1995, pp. 9363-9367.

Ferrara A., et al., "Total, LDL, and HDL Cholesterol Decrease With Age in Older Men and Women," Circulation, vol. 96(1), Jul. 1, 1997, pp. 37-43.

Glossop J.R., et al., "Polymorphism in the Tumour Necrosis Factor Receptor II Gene is associated with circulating levels of soluble tumour necrosis factor receptors in rheumatoid arthritis," Arthritis Research & Therapy, 2005, vol. 7(6), pp. R1227-R1234.

Gudelj I., et al., "Immunoglobulin G glycosylation in Aging and Diseases," Cellular Immunology, vol. 333, 2018, pp. 65-79.

Hager K., et al., "Fibrinogen and aging," Aging Clinical and Experimental Research, vol. 6(2), 1994, pp. 133-138.

Harpole M., et al., "Current State of the Art for Enhancing Urine Biomarker Discovery," Expert Review of Proteomics, Jun. 2016, vol. 13(6), pp. 609-626.

Harris E.S., et al., "Therapeutic Plasma Exchange for the Treatment of Systemic Sclerosis: A Comprehensive Review and Analysis," Journal of Scleroderma and Related Disorders, 2018, vol. 3(2), pp. 132-152.

Huang Z., et al., "Effects of Sex and Aging on the Immune Cell Landscape as Assessed by Single-Cell Transcriptomic Analysis," Proceedings of the National Academy of Sciences of the United States of America, 2021, vol. 118(33), 11 pages.

Josephs S.H., et al., "Serum IgD concentrations in normal infants, children, and adults and in patients with elevated IgE," The Journal of Pediatrics, Mar. 1980, vol. 96(3), pp. 417-420.

Kim et al., Old plasma dilution reduces human biological age: a clinical study. GeroScience (2022).

Kiprov et al., Case Report: Therapeutic and immunomodulatory effects of plasmapheresis in long-haul COVID: a case report. F1000Research 10:1189 (2021).

Kiprov. Guest Editorial. Therapeutic plasma exchange (TPE) and blood products—Implications for longevity and disease. Transfusion and Apheresis Science 60: 103163 (2021).

Kreisberg R.A., et al., "Cholesterol Metabolism and Aging," The American journal of medicine, vol. 82 (Supp 1B), Jan. 26, 1987, pp. 54-60.

Li C., et al., "Multiple Functions of Policosanol in Elderly Patients with Dyslipidemia," Journal of International Medical Research, 2020, vol. 48(7), pp. 1-9.

Li L-H., et al., "Analytical Methods for Cholesterol Quantification," Journal of Food and Drug Analysis, 2019, vol. 27, pp. 375-386.

Lock R.J., et al., "Immunoglobulins and Immunoglobulin Subclasses in the Elderly," Annals of Clinical Biochemistry, 2003, vol. 40, pp. 143-148.

Macdonald-Dunlop et al., A catalogue of omics biological ageing clocks reveals substantial commonality and associations with disease risk. Aging 14(2): 623-659 (2022).

Masuch A., et al., "Preventing Misdiagnosis of Diabetes in the Elderly: Age-Dependent Hba1c Reference Intervals Derived From Two Population-Based Study Cohorts," BMC Endocrine Disorders, 2019, vol. 19, No. 20, 10 pages.

May M.E., et al., "Multicompartment Analysis of the Effects of Plasmapheresis. Application to Lipid Kinetics in Humans," American Journal of Clinical Pathology, Jun. 1989, vol. 91, No. 6, pp. 668-694.

Mc Auley M.T., et al., "LDL-C levels in older people: Cholesterol homeostasis and the free radical theory of ageing converge," Medical Hypotheses, 2017, vol. 104, pp. 15-19.

McGowan M.P., "Emerging Low-Density Lipoprotein (LDL) Therapies: Management of Severely Elevated LDL Cholesterol—The Role of LDL-Apheresis," Journal of Clinical Lipidology, Jun. 2013, vol. 7, No. 3S, pp. S21-S26.

Mehdipour et al., Attenuation of age-elevated blood factors by repositioning plasmapheresis: A novel perspective and approach. Transfusion and Apheresis Science 60(3): 103162 (2021).

Mehdipour et al., Rejuvenation of three germ layers tissues by exchanging old blood plasma with saline-albumin. Aging 12: 8790-8819 (2020).

Musci G., et al., "Age-Related Changes in Human Ceruloplasmin. Evidence for Oxidative Modifications," Journal of Biological Chemistry, Jun. 25, 1993, vol. 268, No. 18, pp. 13388-13395.

Nauck M., et al., "Methods for Measurement of LDL-Cholesterol: A Critical Assessment of Direct Measurement by Homogeneous Assays versus Calculation," Clinical Chemistry, 2002, vol. 48, No. 2, pp. 236-254.

Reverberi R., et al., "Removal Kinetics of Therapeutic Apheresis," Blood transfusion, 2007, vol. 5, pp. 164-174.

Ritchie R.F., et al., "Reference Distributions for Immunoglobulins A, G, and M: A Practical, Simple, and Clinically Relevant Approach in a Large Cohort," Journal of Clinical Laboratory Analysis, 1998, vol. 12, pp. 363-370.

Rufini A., et al., "Senescence and Aging: The Critical Roles of P53," Oncogene, 2013, pp. 1-15.

Salameh Y., et al., "DNA Methylation Biomarkers in Aging and Age-Related Diseases," Frontiers in Genetics, Mar. 10, 2020, vol. 11, No. 171, 11 pages.

Salvioli S., et al., "Inflamm-Aging, Cytokines and Aging: State Of The Art, New Hypotheses on the Role of Mitochondria and New Perspectives from Systems Biology," Current Pharmaceutical Design, 2006, vol. 12, No. 24, pp. 3161-3171.

Sayed N., et al., "An Inflammatory Aging Clock (iage) based on Deep Learning Tracks Multimorbidity, Immunosenescence, Frailty and Cardiovascular Aging," Nature Aging, Jul. 2021, vol. 1, pp. 598-615.

Walter M., "Interrelationships among HDL Metabolism, Aging, and Atherosclerosis," Arteriosclerosis, Thrombosis, and Vascular Biology, 2009, vol. 29(9), pp. 1244-1250.

(56) References Cited

OTHER PUBLICATIONS

Williams M.E., et al., "Principles of Separation: Indications and Therapeutic Targets for Plasma Exchange," Clinical Journal of the American Society of Nephrology, Jan. 2014, vol. 9, pp. 181-190.

Winters J.L., "Plasma Exchange: Concepts, Mechanisms, and an Overview of the American Society for Apheresis Guidelines," Hematology, 2012, pp. 7-12.

Xavier R.M., et al., "Antinuclear Antibodies in Healthy Aging People: A Prospective Study," Mechanisms of Ageing and Development, 1995, vol. 78, pp. 145-154.

Xu M., et al., "Senolytics Improve Physical Function and Increase Lifespan in Old Age," Nature Medicine, Aug. 2018, vol. 24, No. 8, pp. 1246-1256.

Yang C-S., et al., "Effect of Ageing on Human Plasma Glutathione Concentrations As Determined By High-Performance Liquid Chromatography with Fluorimetric Detection," Journal of Chromatography B, 1995, vol. 674, pp. 22-30.

Yi S-W., et al., "Total Cholesterol and All-Cause Mortality by Sex and Age: A Prospective Cohort Study among 12.8 Million Adults," Scientific Reports, 2019, vol. 9, No. 1596, 10 pages.

Buchele et al. A simplified extracorporeal photopheresis procedure based on single-dose ultraviolet A light irradiation shows similar in vitro efficacy. Transfusion 61: 883-893 (2021).

Gilmutdinova I., et al., "The Use of Therapeutic Plasmapheresis in Preventive and Sports Medicine," Bio Web of Conferences, 2022, vol. 48:01009, 7 pages.

Wang et al. Modulation of B Cells and Homing Marker on NK Cells Through Extracorporeal Photopheresis in Patients With Steroid-Refractory/Resistant Graft-vs-Host Disease (GvHD) Without Hampering Anti-Viral/Anti-leukemic Effects. Frontiers in Immunology 9 (Article 2207): 1-15 (Oct. 2018).

Xu W., et al., et al., "Markers of T Cell Senescence in Humans," International Journal of Molecular Sciences, Aug. 2017, vol. 18:1742, 13 pages.

Borgoni S., et al., "Targeting Immune Dysfunction in Aging," Ageing Research Reviews, 2021, vol. 70, 101410, 16 pages, Retrieved from the Internet: URL: https://doi.org/10.1016/j.arr.2021.101410.

Busse S, et al. Expression of HLA-DR, CD80 and CD86 in Healthy Aging and Alzheimer's Disease j Alzheimers Dis 2015, vol. 47, No. 1, pp. 177-184 (abstract).

Clinicaltrials.gov, "Plasmapheresis for Treatment of Age-Related Frailty," NCT05054894, Apr. 18, 2022, [Retrieved on Feb. 22, 2023].

Denntt N.S., et al., "Age Associated Decline in CD25 and CD28 Expression Correlate with an Increased Susceptibility to CD95 Mediated Apoptosis in T Cells," Experimental Gerontology, 2002, vol. 37, No. 2-3, pp. 271-283.

Engman J., et al., "Age, Sex and NK1 Receptors in the Human Brain -- a Positron Emission Tomography Study with [11C]GR205171," European Neuropsychopharmacology, 2012, vol. 22, No. 8, pp. 562-568.

International Search Report and Written Opinion for Application No. PCT/US2023/024058, mailed on Apr. 8, 2024, 32 pages.

Lutz C.T., et al., "Reciprocal Age Related Change in Natural Killer Cell Receptors for MHC Class I," Mechanisms of Ageing and Development, 2005, vol. 126, No., 6-7, pp. 722-731.

Martin V., et al., "Age-Related Aspects of Human IgM(+) B Cell Heterogeneity," Annals of the New York Academy of Sciences, 2015, vol. 1362, pp. 153-163.

Parker D.C., et al., "Association of Blood Chemistry Quantifications of Biological Aging With Disability and Mortality in Older Adults," The Journals of Gerontology. Series A, Biological Sciences and Medical Sciences, 2020, vol. 75, No. 9, pp. 1671-1679.

Pieren D.K.J., et al., "Co-Expression of TIGIT and Helios Marks Immunosenescent CD8+ T Cells During Aging," Frontiers in Immunology, May 16, 2022, vol. 13: 833531, 14 pages, Retrieved from the Internet: URL: https://doi.org/10.3389/fimmu.2022.833531.

Pieren D.K.J., et al., "Regulatory Kir+Ra+ T Cells Accumulate with Age and Are Highly Activated During Viral Respiratory Disease," Aging Cell, 2021, vol. 20:e13372. 18 pages, https://doi.org/10.1111/acel.13372.

Seidler S., et al., "Age-Dependent Alterations of Monocyte Subsets and Monocyte-Related Chemokine Pathways in Health Adults," BMC Immunology, 2010, vol. 11, No. 30, 11 pages, Retrieved from the Internet: URL: http://www.biomedcentral.com/1471-2172/11/30.

Shrivastava S., et al., "CCR5+ T-Cells Homed to the Liver Exhibit Inflammatory and Profibrogenic Signatures in Chronic HIV/HCV-Coinfected Patients," Viruses, 2021, vol. 13(10):2074, 12 pages, Retrieved from the Internet: URL: https://doi.org/10.3390/v13102074.

* cited by examiner

COMPOSITIONS AND METHODS FOR PLASMAPHERESIS

CROSS-REFERENCE

This application claims the benefit of U.S. Provisional Patent Application No. 63/347,124, which was filed on May 31, 2022, and which is incorporated herein in its entirety by reference.

BACKGROUND OF THE DISCLOSURE

During the past century, the earth's population has more than doubled. It is estimated that more than 20% of the world's population is aged 65 years or older. The United Nations estimates that, by 2050, this population will have increased beyond 14 billion. Aged humans almost inevitably suffer from one or more disorders associated with chronic aging. These can include Alzheimer's disease, infections, Type II Diabetes, atherosclerotic cardio vascular disease, obesity, osteoporosis, and sarcopenia. The cumulative effect is an enormous financial burden to any medical system.

SUMMARY OF THE DISCLOSURE

Described herein is a method of providing plasmapheresis to an individual in order to improve a health status of the individual, comprising steps of: (a) measuring, before an administration of plasmapheresis, one or more of a strength of the individual, a balance of the individual, a mental status of the individual, and a measure of a walking of the individual, thereby generating an indication of a pre-treatment health status of the individual; (b) administering the plasmapheresis to the individual; (c) measuring, following step (b), one or more of the strength of the individual, the balance of the individual, the mental status of the individual, and the measure of the walking of the individual, thereby generating an indication of a post-treatment health status of the individual; and (d) comparing the post-treatment health status of the individual with the pre-treatment health status of the individual in order to determine that the health status of the individual has improved as a result of the plasmapheresis administration. In some embodiments, step (a) occurs within 24 hours of the administering of the plasmapheresis to the individual in step (b). In some embodiments, the strength of the individual is measured in step (b) by measuring a grip strength of the individual. In some embodiments, balance of the individual is measured in step (a), step (c), or steps (a) and (c) by having the individual stand on one leg and measuring how long the individual remains standing with one leg raised. In some embodiments, the mental status is measured in step (a), step (c), or steps (a) and (c) using a survey comprising questions that assess emotional wellbeing. In some embodiments, the measure of the walking of the individual is measured in step (a), step (c), or steps (a) and (c) by having the individual stand from a seated position and walk. In some embodiments, the plasmapheresis that is administered in step (b) exchanges at least one unit of plasma volume. In some embodiments, the plasmapheresis that is administered in step (b) is administered over a plurality of treatment sessions. In some embodiments, two treatment sessions of the plurality of treatment sessions are administered within 72 hours of each other. In some embodiments, the plasmapheresis that is administered in step (b) is administered over a single treatment session. In some embodiments, the comparing the post-treatment health status of the individual with the pre-treatment health status of the individual in step (d) results in a determination of a quantitative difference between the post-treatment health status of the individual and the pre-treatment health status of the individual. In some embodiments, the method further comprises repeating steps (b)-(d) until the quantitative difference is a specific value. In some embodiments, the method further comprises repeating steps (a)-(d) until the quantitative difference is a specific value.

Described herein is a method for treating a condition associated with aging in an individual, comprising: (a) administering plasmapheresis to the individual; and (b) monitoring for a change in the condition. In some embodiments, the condition associated with aging comprises a loss of strength. In some embodiments, the strength of the individual is monitored in step (b) by measuring a grip strength of the individual. In some embodiments, the condition associated with aging comprises a loss of balance. In some embodiments, balance of the individual is monitored in step (b) by having the individual stand on one leg and measuring how long the individual remains standing with one leg raised. In some embodiments, the condition associated with aging comprises diminished ability to walk. In some embodiments, the ability to walk of the individual is monitored in step (b) by having the individual stand from a seated position and walk. In some embodiments, the plasmapheresis that is administered in step (a) exchanges at least one unit of plasma volume. In some embodiments, the plasmapheresis that is administered in step (a) is administered over a plurality of treatment sessions. In some embodiments, two treatment sessions of the plurality of treatment sessions are administered within 72 hours of each other. In some embodiments, the plasmapheresis that is administered in step (a) is administered over a single treatment session. In some embodiments, the method further comprises repeating steps (a)-(b) until the change in the condition is achieved.

Described is a method for using plasmapheresis to treat an individual by using the plasmapheresis to modulate an amount of expression of a cell surface marker on the cell surface of a white blood cell of the individual, comprising the steps of: (a) measuring, before an administration of plasmapheresis, a level of expression of the cell surface marker in blood of the individual; (b) administering the plasmapheresis to the individual; and (c) measuring, following step (b), the level of expression of the cell surface marker in the blood of the individual and determining that the expression of the cell surface marker on the cell surface of the white blood cell of the individual has been modulated. In some embodiments, the white blood cell comprises a lymphocyte. In some embodiments, the lymphocyte comprises a T-cell. In some embodiments, the white blood cell comprises a monocyte. In some embodiments, the white blood cell comprises a basophil. In some embodiments, the white blood cell comprises a neutrophil. In some embodiments, the white blood cell comprises an eosinophil. In some embodiments, to modulate the amount of expression of the cell surface marker on the cell surface of the white blood cell of the individual is to change the amount of expression of the cell surface marker to a degree that is measurable in the blood of the individual following the administering of plasmapheresis in step (b). In some embodiments, the cell surface marker comprises CD16. In some embodiments, the cell surface marker comprises CD25. In some embodiments, the cell surface marker comprises CD27. In some embodiments, the cell surface marker comprises CD38. In some embodiments, the cell surface marker comprises CD57. In some embodiments, the cell surface marker comprises CD80. In some embodiments, the cell surface marker comprises HLADR. In some embodiments, the cell surface marker comprises IgM. In some embodiments, the cell surface marker comprises KTR. In some embodiments, the cell surface marker comprises KLRG1. In some embodiments, the cell surface marker comprises NK1. In some embodiments, the cell surface marker comprises NKg2a. In some embodiments, the cell surface marker comprises TIGIT. In some embodiments, step (a) occurs within 24 hours of the administering of the plasmapheresis to the individual in step (b). In some embodiments, the plasmapheresis that is administered in step (b) exchanges at least one unit of plasma volume. In some embodiments, the plasmapheresis that is administered in step (b) is administered over a plurality of treatment sessions. In some embodiments, two treatment sessions of the plurality of treatment sessions are administered within 72 hours of each other. In some embodiments, the plasmapheresis that is administered in step (b) is administered over a single treatment session. In some embodiments, the expression of the cell surface marker is measured using flow cytometry. In some embodiments, the expression of the cell surface marker is measured using a fluorescent conjugated antibody. In some embodiments, the modulation is a measurable decrease between level of expression of the cell surface marker that is measured in step (a) and the level of expression of the cell surface marker measured in step (c). In some embodiments, the method further comprises repeating steps (b)-(c) until the cell surface modulation having a specific value is achieved. In some embodiments, the method further comprising repeating steps (a)-(c) until the cell surface modulation having a specific value is achieved.

Described herein is a method for treating aging in an individual by using plasmapheresis to reduce cellular senescence in the individual, comprising the steps of: (a) measuring, before an administration of plasmapheresis, a level of expression of a marker associated with the cellular senescence in blood of the individual; (b) administering the plasmapheresis to the individual; and (c) measuring, following step (b), the level of expression of the marker associated with the cellular senescence and determining that the cellular senescence in the individual has been reduced. In some embodiments, a cell in which the cellular senescence is reduced comprises a lymphocyte. In some embodiments, the lymphocyte comprises a T-cell. In some embodiments, a cell in which the cellular senescence is reduced comprises a monocyte. In some embodiments, a cell in which the cellular senescence is reduced comprises a basophil. In some embodiments, a cell in which the cellular senescence is reduced comprises a neutrophil. In some embodiments, a cell in which the cellular senescence is reduced comprises an eosinophil. In some embodiments, the marker associated with the cellular senescence comprises senescence-associated beta-galactosidase ("SA-β-gal"). In some embodiments, step (a) occurs within 24 hours of the administering of the plasmapheresis to the individual in step (b). In some embodiments, the plasmapheresis that is administered in step (b) exchanges at least one unit of plasma volume. In some embodiments, the plasmapheresis that is administered in step (b) is administered over a plurality of treatment sessions. In some embodiments, two treatment sessions of the plurality of treatment sessions are administered within 72 hours of each other. In some embodiments, the plasmapheresis that is administered in step (b) is administered over a single treatment session. In some embodiments, the expression of the marker associated with the cellular senescence is measured using flow cytometry. In some embodiments, the expression of the marker associated with the cellular senescence is measured using a fluorescent conjugated antibody. In some embodiments, the modulation is a measurable decrease between level of expression of the marker associated with the cellular senescence that is measured in step (a) and the level of expression of the marker associated with the cellular senescence that is measured in step (c). In some embodiments, the method further comprises repeating steps (b)-(c) until a specific value is achieved for the reduction of the level of expression of the marker associated with the cellular senescence. In some embodiments, the method further comprises repeating steps (a)-(c) until a specific value is achieved for the reduction of the level of expression of the marker associated with the cellular senescence.

Described herein is a method for performing plasmapheresis for use in treating or preventing a condition that is associated with aging in an individual, the method comprising: removing, from within a vascular system of an individual, at least 70% of a factor that is associated with aging by performing plasmapheresis on the individual at least two times within a 72 hour period and thereby treating or preventing the condition that is associated with aging in the individual. In some embodiments of the method, each of the at least two times that plasmapheresis is performed comprises removing at least one plasma volume from the individual. In some embodiments of the method, a volume of exchange fluid that is returned to the individual is equal in volume to the at least one plasma volume that is withdrawn. In some embodiments of the method, a volume of exchange fluid that is returned to the individual is greater in volume than the at least one plasma volume that is withdrawn. In some embodiments of the method, at least one of the at least two times that plasmapheresis is performed comprises removing at least one- and one-half plasma volumes from the individual. In some embodiments of the method, a volume of exchange fluid that is returned to the individual is equal to the at least one- and one-half plasma volumes that is withdrawn. In some embodiments of the method, a volume of exchange fluid that is returned to the individual is greater than the at least one- and one-half plasma volume that is withdrawn. In some embodiments of the method, the plasmapheresis includes infusing an exchange fluid into a vascular system of the individual and wherein the exchange fluid comprises at least one of: saline, Lactated Ringer's, albumin, or therapeutic. In some embodiments of the method, the therapeutic comprises at least one of: an anti-inflammatory or an immune-modulator. In some embodiments of the method, the immune-modulator comprises intravenous immunoglobulin. In some embodiments of the method, the method comprises the step of administering a therapeutic to the individual following at least one of the at least two times that the plasmapheresis is performed. In some embodiments of the method, the therapeutic comprises at least one of: an anti-inflammatory or an immune-modulator. In some embodiments of the method, the immune-modulator comprises intravenous immunoglobulin.

Described herein is a method for performing plasmapheresis for use in treating or preventing a condition that is associated with aging in an individual, the method comprising: (a) determining a biological age of an individual; (b) performing plasmapheresis on the individual; and (c) repeating steps (a) and (b) until the biological age of the individual is below a threshold value. In some embodiments of the method, the biological age of the individual is determined using an albumin blood level of the individual. In some embodiments of the method, the biological age of the individual is determined using a degree of glycation of albumin in blood of the individual. In some embodiments of the method, the biological age of the individual is determined using a ceruloplasmin blood level of the individual. In some embodiments of the method, the biological age of the individual is determined using a level of an immunoglobulin in the blood of the individual. In some embodiments of the method, the biological age of the individual is determined using a glutathione blood level of the individual. In some embodiments of the method, the biological age of the individual is determined using an antibody assay, and wherein the antibody assay comprises at least one of an antinuclear antibody screen, a rheumatoid factor assay, a thyroid peroxidase antibody assay, or a quantitative immunoglobulin assay. In some embodiments of the method, the biological age of the individual is determined using a proteomic assay, and wherein the proteomic assay comprises at least one of a fibrinogen assay, a creatinine kinase assay, or a hemoglobin A1C assay. In some embodiments of the method, the biological age of the individual is determined using a metabolomic assay, and wherein the metabolomic assay comprises at least one of a cholesterol assay or a blood glucose assay. In some embodiments of the method, the biological age of the individual is determined using a urinalysis. In some embodiments of the method, the biological age of the individual is determined using a peripheral blood mononuclear cell analysis. In some embodiments of the method, the biological age of the individual is determined using a cellular senescence assay. In some embodiments of the method, the biological age of the individual is determined using a genomic methylation assay. In some embodiments of the method, the biological age of the individual is determined using an inflammatory marker analysis. In some embodiments of the method, the biological age of the individual is determined using at least one of a complete blood count, a total protein assay, a liver function assay, a blood urea nitrogen assay, a creatinine assay, or a c-reactive protein assay.

Described herein is a method for performing a plasmapheresis regimen, comprising the steps of: (a) withdrawing at least 1 plasma volume of whole blood from an individual; (b) separating the whole blood into a cellular fraction and a plasma fraction; (c) returning the cellular fraction to the individual; (d) infusing an exchange fluid to the individual simultaneously with step (a); and (e) repeating steps (a)-(d) until at least one component found in plasma of the individual is diluted by at least 60% as compared to before the plasmapheresis regimen was initiated.

Described herein is a method for treating a condition associated with aging in an individual, comprising performing plasmapheresis on the individual and removing at least one plasma volume from the individual during the plasmapheresis. In some embodiments, the condition associated with aging is a decrease in strength of the individual. In some embodiments, wherein the condition associated with aging is a decrease in ambulation of the individual. In some embodiments, the condition associated with aging is a decrease in balance in the individual. In some embodiments, the condition associated with aging is a decrease of the mental status of the individual. In some embodiments, the condition associated with aging is an increase inflammation in the individual. In some embodiments, the increase in the inflammation in the individual is associated with a change in level of expression of a cell surface protein expressed on the surface of a white blood cell. In some embodiments, the white blood cell comprises a lymphocyte. In some embodiments, the lymphocyte comprises a T-cell. In some embodiments, the white blood cell comprises a monocyte. In some embodiments, the white blood cell comprises a basophil. In some embodiments, the white blood cell comprises a neutrophil. In some embodiments, the white blood cell comprises an eosinophil. In some embodiments, the cell surface protein comprises CD16. In some embodiments, the cell surface protein comprises CD25. In some embodiments, the cell surface protein comprises CD27. In some embodiments, the cell surface protein comprises CD38. In some embodiments, the cell surface protein comprises CD57. In some embodiments, the cell surface protein comprises CD80. In some embodiments, the cell surface protein comprises HLADR. In some embodiments, the cell surface protein comprises IgM. In some embodiments, the cell surface protein comprises KTR. In some embodiments, the cell surface protein comprises KLRG1. In some embodiments, the cell surface protein comprises NK1. In some embodiments, the cell surface marker comprises NKg2a. In some embodiments, the cell surface protein comprises TIGIT.

A plasmapheresis exchange fluid composition for use in administering plasmapheresis for treating or preventing a condition that is associated with aging in an individual, wherein a total volume of the plasmapheresis exchange fluid composition is equal to at least one plasma volume of the individual. In some embodiments, the composition comprises 5% albumin. In some embodiments, the composition comprises IVIG. In some embodiments, the condition associated with aging is a decrease in strength of the individual. In some embodiments, the condition associated with aging is a decrease in ambulation of the individual. In some embodiments, the condition associated with aging is a decrease in balance in the individual. In some embodiments, the condition associated with aging is a decrease of the mental status of the individual. In some embodiments, the condition associated with aging is an increase inflammation in the individual. In some embodiments, the increase in the inflammation in the individual is associated with a change in a level of expression of a cell surface protein expressed on the surface of a white blood cell. In some embodiments, the white blood cell comprises a lymphocyte. In some embodiments, the lymphocyte comprises a T-cell. In some embodiments, the white blood cell comprises a monocyte. In some embodiments, the white blood cell comprises a basophil. In some embodiments, the white blood cell comprises a neutrophil. In some embodiments, the white blood cell comprises an eosinophil. In some embodiments, the cell surface protein comprises CD16. In some embodiments, the cell surface protein comprises CD25. In some embodiments, the cell surface protein comprises CD27. In some embodiments, the cell surface protein comprises CD38. In some embodiments, the cell surface protein comprises CD57. In some embodiments, the cell surface protein comprises CD80. In some embodiments, the cell surface protein comprises HLADR. In some embodiments, the cell surface protein comprises IgM. In some embodiments, the cell surface protein comprises KTR. In some embodiments, the cell surface protein comprises KLRG1. In some embodiments, the cell surface protein comprises NK1. In some embodiments, the cell surface protein comprises NKg2a. In some embodiments, the cell surface protein comprises TIGIT.

Described herein is a plasmapheresis exchange fluid composition for use in administering plasmapheresis for reducing cellular senescence in an individual, wherein a total volume of the plasmapheresis exchange fluid composition is equal to at least one plasma volume of the individual. In some embodiments, the composition comprises 5% albumin. In some embodiments, the composition comprises IVIG. In some embodiments, a cell in which the cellular senescence is reduced comprises a lymphocyte. In some embodiments, the lymphocyte comprises a T-cell. In some embodiments, a cell in which the cellular senescence is reduced comprises a monocyte. In some embodiments, a cell in which the cellular senescence is reduced comprises a basophil. In some embodiments, a cell in which the cellular senescence is reduced comprises a neutrophil. In some embodiments, a cell in which the cellular senescence is reduced comprises an eosinophil. In some embodiments, a marker associated with the cellular senescence comprises senescence-associated beta-galactosidase ("SA-β-gal") and wherein the cellular senescence is measured by measuring the marker. In some embodiments, the plasmapheresis that is administered is administered over a plurality of treatment sessions. In some embodiments, two treatment sessions of the plurality of treatment sessions are administered within 72 hours of each other. In some embodiments, the plasmapheresis that is administered is administered over a single treatment session. In some embodiments, the cellular senescence is reasured by measuring a marker associated with the cellular senescence, and wherein expression of the marker is measured using flow cytometry. In some embodiments, the expression of the marker is measured using a fluorescent conjugated antibody.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein) of which:

DETAILED DESCRIPTION

Aging

Figure 1:
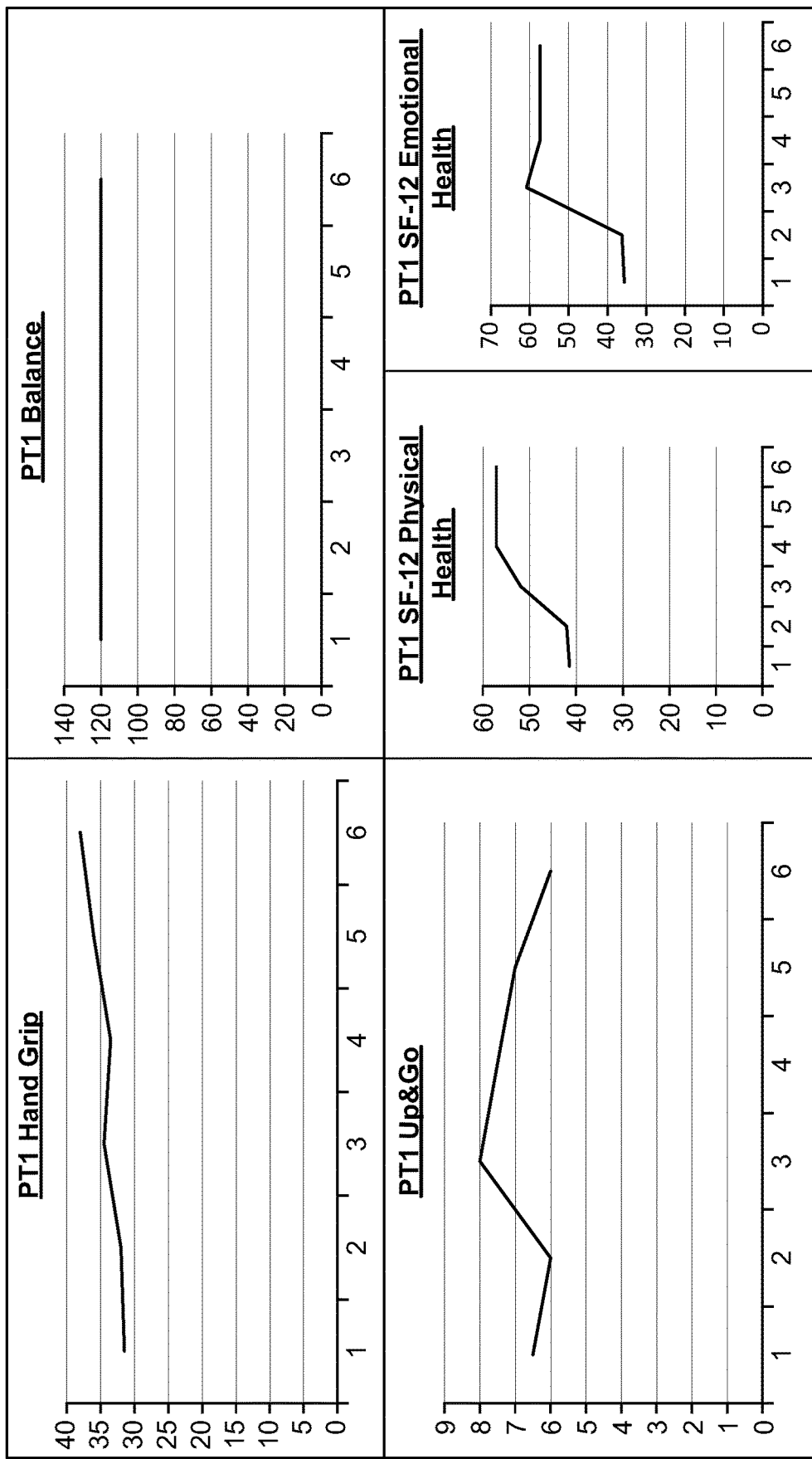
FIG. 1 is a series of graphs of physical, and mental macro data for a female collected over the course of six plasmapheresis treatments.

Aging coincides with progressions which affect recognizable and often deleterious changes in comfort, fitness, appearance and cognition. While some of these progressions manifest as readily identifiable changes in appearance (e.g., in humans, looser skin, increased mouth and nose width, and eye droop), the underlying biochemistry—which is believed to involve, among other things, complex and multifaceted changes in molecular and signaling pathways over time—is not yet fully understood. A great deal of research is currently being conducted to better understand the science of aging and changes (e.g. genetic, physiologic) associated with aging at both the micro and macro level of different organisms including humans. Generally, changes and conditions that are associated with aging are considered negative and there is a great deal of benefit in treatments described herein that can improve a health status of an individual by addressing changes and conditions associated with aging.

Effects of Aging

Many age-related developments are considered unwelcome and deleterious to quality of life, such as, for example, hearing and vision loss, arthritis, and loss of cognitive function. This phenomenon is nearly ubiquitous across species, wherein past a certain point, aging coincides with diminished capabilities and biological function. In addition, certain diseases are highly associated with and possibly interrelated with aging, because, for example, aging corresponds with: degenerative processes, diminished recovery or healing capacity, increased propensity for acute stress and immune response; all of which create an environment where certain disease processes can occur. As an example, rheumatoid arthritis is a disease highly associated with aging, the pathophysiology of which is associated with tissue degeneration, diminished recovery or healing and increased propensity for acute stress and immune response.

Physiological effects of aging (i.e. conditions associated with aging) include decreased strength, decreased mobility (and specifically decreased ability to walk), decreased balance, and subjective changes in mental wellbeing.

Mechanisms of Aging

The mechanisms associated with aging are not at this time fully understood, however, a number of observations provide at least empirical insight into factors associated with aging. Observations have, for example, shown that aging is likely influenced by a number of health and lifestyle factors (i.e. ostensibly non-genetic factors), including stress, diet, sleep hygiene, and sun exposure. To say that age is influenced by these factors is to say that observations seem to indicate that affecting a change in one or more of these factors can influence a rate and/or severity of aging. For example, affecting diet through moderate caloric restriction is a well established and reliable means for slowing aging which strongly suggests that diet is an important component of the aging process.

It is also strongly believed, and supported by certain research, that there is a genetic component to aging as well, wherein expression of certain genes is believed to drive aging related processes and either over or under expression of certain genes can lead to slowing or acceleration of the aging process. Gene expression, in the context of aging, can result in the production of peptides capable of acting on or otherwise affecting targets located relatively remotely, within the body, from the cell that contains the genes that are expressed. In this way, genes expressed in one cell type or one tissue type can have effects on cells or tissues that are remote from where the gene was originally expressed.

Peptides produced by expression of genes associated with aging may be modified within the body by other chemical processes which then may affect the function of the peptide. Such chemical processes that modify post-translational peptides include but are not limited to methylation, glycation, and glycosylation. The type of chemical modification as well as the degree of chemical modification of certain post-translational peptides may be both a cause of age-related changes and also a marker of aging as well. For example, a degree of glycation of a peptide found in blood such as, for example, albumin may directly corelated with aging generally or a specific aging process. A degree of chemical modification of a post-translational peptide can refer to the percent of peptides found to have undergone the particular modification and/or a degree of modification seen within one or more of the peptides.

Aging is also associated with an increase in the levels of pro-inflammatory markers in blood and tissues, which is a strong risk factor for multiple diseases that are highly prevalent and frequent causes of disability in elderly individuals. This phenomenon is referred to as "inflammaging." Reducing or even reversing inflammaging in aging patients is a pathway to treating conditions associated with aging and even treating or reversing aging itself.

Effect of Aging on Lifespan and Longevity

The term "lifespan" as used herein is the duration of the life of the individual. Whereas when measured in a population of individuals lifespan can be any cumulative measure across the entire population or a portion of the population (i.e. a sub-population), such as, for example, an average lifespan of the population or sub-population, a median lifespan of the population or sub-population, a variance in lifespan of the population or sub-population, and so on.

The term "longevity" as used herein means that an individual or population of individuals has a lifespan or expected lifespan that lasts longer than a reference lifespan. For example, historical data can provide expected lifespans for a population which can serve as a reference lifespan. An "expected lifespan" as used herein may describe any measure of a lifespan of an individual or lifespans within a population that can be reasonably used as a predictor or marker for a lifespan of another individual or individuals within a population. For example, an expected lifespan of an individual having a particular physiology can be obtained by calculating an average lifespan for a population of individuals having the same particular physiology so that the average lifespan can serve as a reference lifespan. It should be understood that there are a multitude of ways to determine a reference lifespan including using statistical techniques for data of a relevant population such as, for example, mean, median, mode, standard deviation, and variance.

The aging process counters or limits longevity in the sense that aging has a shortening effect on lifespan. It is well understood that the aging process is not only associated with adverse physiologic change and increased likelihood of development of life threatening disease, but is also either a direct or indirect cause of death, which of course shortens lifespan. It is also well understood that mitigating, preventing, halting, and/or reversing the effects of aging will promote increased lifespan and therefore promote longevity. Generally speaking, if you can significantly counter aging, you promote the ability to avoid death and therefore live longer, thereby, increasing lifespan and promoting longevity. This is true for individuals as well as a population of individuals. Therefore, aside from aging being a good target for therapy in its own right, therapies that address aging are expected to promote longevity as well.

Therapies that promote longevity can, therefore, be defined as those that promote a relative increase in lifespan in an individual or a population and/or therapies that treat, mitigate, and/or prevent the effects of aging. For example, an expected lifespan for a male human having a particular physiologic feature or features, such as, for example, dark hair and green eye color, may correspond to 89.4 years, where 89.4 years is the average lifespan of a population of males with dark hair and green eyes. It can then be said that a male human with these same physiologic features (i.e. dark hair and green eyes) experiences longevity when he outlives the expected lifespan by, for example, living until the age of 91 years old. Similarly, a population of males from a particular geographic region, such as, for example, Greece, with these same physiologic features (i.e. a subset of the larger population of males with dark hair and green eyes but from the specific geographic region of Greece) can be said to have longevity if they all individually have a lifespan that is longer than 89.4 years. Therefore, a therapy associated with or that results in the lifespan of the individual or the lifespans of individuals in a population being longer than an expected lifespan can be said to be a therapy that promotes longevity.

In addition, therapies that promote longevity can also be defined as those therapies that cause an increase in an expected lifespan of an individual relative to an existing expected lifespan of a reference individual or reference population. For example, a person who is a smoker and has initial expected lifespan, then undergoes a therapy that causes him to quit smoking and the quitting of smoking results in a longer expected lifespan.

Biological Age

As used herein, the term "chronological age" refers to the number of years that an individual has existed which is a duration of time which can be expressed as "age" or "years old". Chronological age is purely a chronological measurement of time having a start point (typically at birth) and an end point at death and is not determined based on any property of the individual either physical or biological. For example, an individual's chronological age does not change based on how old their physical appearance makes them appear nor does it change based on a family history or genetic feature that would suggest a specific lifespan for the individual. The term "biological age," as used herein, on the other hand, is a measure of the aging process and takes into account physical, biological, genetic, and biochemical features of an individual, including but not limited to biological progressions, genetic and epigenetic features, homeostasis measurements, disease-risk, and various molecular changes associated with an individual.

Biological age may be expressed as a duration of years similar to how chronological age is expressed. Biological age may refer to an individual as a whole or other aspects such as, for example, an organ, an organ system, or other functional system of the individual. For example, an individual as a whole may have the biological age of 35 and an immune system age of 27 (i.e. where an immune system age is a subset or type of biological age).

It is notable that biological age and chronological age may be decoupled, leading to appearances, energy levels, and/or biological profiles of chronologically older or younger individuals. For example, an individual may be 55 years old (in terms of chronological age) but have the biological age of 42 years old. Likewise, an individual who is 35 years old may have a biological age of 51 years old.

Biological age, at least in some respects, can be thought of as a measurable performance metric, wherein it is favorable for an individual to have a biological age—as a whole or with respect to a particular feature of the individual—that is less than the chronological age of the individual. For example, an individual who has a chronological age of 70 years, assuming that they have their own liver and not a transplanted liver, has a liver which has a chronological age of 70 years as well. The same individual of the example may have—based on, for example, one or more measures discussed above—a biological age of 68 years as an individual. And, the same individual of the example, may have—based on, for example, one or more measures discussed above—a liver with a biological age of 65 years. That is, in this example an individual may have an overall biological age of 68 years whereas an organ of the same individual (in this example, their liver) has a biological age of 65 years old. In this way biological age can be considered a holistic measure or a measure of individual systems and/or a measure of a processes within the body of an individual.

In both examples, biological age may be computed using one or more markers or factors that correlate with or indicate the biological age of an individual. Such markers or factors may be measured and/or detected through testing of a biological sample such as, for example, blood, urine, sputum, and sweat.

In addition to population-level variation, biological aging can progress at multiple rates within an individual. Owing to genetics, lifestyle, health, and environmental factors, separate organs, tissue-types, or cells within the individual may exhibit disparate biological ages. For example, among a multitude of cumulative and deleterious effects, obesity, diabetes, and renal diseases often accelerate aging in kidneys, such that apparent ages of such a person's kidneys can be much higher than those of their other organs and omic profiles (e.g., plasma proteomics). Even in healthy individuals, marked biological age variation can occur.

While biological aging rates appear to be responsive to ranges of genetic and environmental factors, most organisms appear to follow innate and encoded aging timelines. Although biological aging exhibits some intraspecies variation, upper and lower bounds for aging rates appear to be primarily determined by species type. For example, while there are no known cases of humans living past 125 years of age, bowhead whales routinely reach 200 years of age, and certain species of clams consistently live beyond 500 years. Exemplifying the other extreme, African killifish typically only live for between 4 and 6 months, and exhibit signs of advanced aging as early as 2 months. Supporting a genetic underpinning for aging, a number of human diseases modify biological aging rates, with Hutchinson-Gilford Syndrome, Werner Syndrome, and Down Syndrome increasing biological aging by about 100-800%.

Biological Age Markers

Aging coincides with diverse and complex progressions at molecular, cellular, and tissue levels. As disclosed herein, select aspects of these progressions can be monitored to determine biological age in a subject. As many markers for aging can also be responsive to health, lifestyle, and environment, methods for determining biological age can utilize multiple biological markers, and may further use non-age responsive biomarkers as calibrants.

Exemplary biomolecules, genetic and epigenetic markers, expression patterns, and associated measurement methods which can be useful for diagnosing chronological and biological age are outlined below. While the biomarkers outlined in this section are of particular utility, they are intended to serve as examples of age-diagnostic species, and are not intended to be limiting.

Blood-Based Biomarkers

Many of the molecular and biological changes associated with aging manifest in altered blood composition. At a population level, aging correlates with consistent, if nonetheless complex, changes in blood phenotypes. While some of these changes can be mapped to straightforward increases or decreases of single biomarkers, such as progressive increases in inflammatory peptide biomarker (e.g., interleukin (IL)-6), C-reactive protein, and tumor necrosis factor-α (TNF-α)) levels with age, aging can also correlate with changes in biomarker processing (e.g., immunoglobulin glycosylation patterns) and ratios among groups of species.

(i) Albumin

For many individuals, albumin, the highest abundance serum protein, can serve as a robust biomarker for aging. Albumin is a family of globular transport proteins essential for lipid, hormone, and metabolite clearance and homeostasis. Following typical peak concentrations of 40 to 50 mg/mL during late adolescence, serum albumin concentrations often decrease by hundreds of μg/mL annually, and exhibiting accelerated rates of diminution at advanced ages. While a typical serum albumin level is about 45 and 42 mg/mL for 30-year-old males and females, respectively, by age 60, mean levels decrease to about 42 and 40 mg/mL for males and females, respectively.

Furthermore, albumin often exhibits age-dependent structural changes which may be useful for aging diagnostics. In most humans, the proportion of glycated albumin increases with age, and typically leads to diminished function. As albumin activity is essential for multiple forms of homeostasis, the combined impact of diminished albumin levels and activity can contribute to adverse symptoms of aging (e.g., diminished energy), and may even augment biological aging rates. Albumin glycation can also evidence other age-related developments, including diminished concentrations and functions of regulatory proteins such as insulin. Accordingly, serum albumin concentration, isoform ratios, and post-translational modifications (e.g., glycation patterns) can not only serve as diagnostic markers for age, but can evidence the severity of age-related symptoms.

(ii) Ceruloplasmin

For many individuals, changes in ceruloplasmin levels and morphology can be used to quantitate biological age. Ceruloplasmins are a class of copper proteins which participate in iron oxidation and trafficking. Accordingly, ceruloplasmins perform central roles in iron trafficking and reactive oxygen species prevention. Ceruloplasmins exhibit progressive changes in post-translational modification and isoform populations with aging, which can affect activity, localization (e.g., intravascular versus extravascular distribution), and clearance rate.

While ceruloplasmin consortia typically contain complex arrays of isoforms and post-translational modification patterns, age-related progressions often manifest as detectable changes in ceruloplasmin copper centers. Such changes can be detected with paramagnetically sensitive spectroscopies such as electron paramagnetic resonance and magnetic circular dichroism, and can evidence broader changes in structure, isoform ratio, and post-translational modification patterns (e.g., see Musci et al. *J Biol Chem*, 1993; 268(18): 13388-95). Ceruloplasmin also often exhibits age-dependent carbonylation and net charge, with greater than 3-fold more carbonylation (e.g., as measured by mass spectrometry) and 0.1 higher isoelectric points (e.g., as measured by 2-dimensional gel electrophoresis) in 65-year-old than in 15-year-old subjects. Accordingly, ceruloplasmin structure, isoform ratios, post translational modification patterns, and combinations thereof can be used to assess biological age.

(iii) Immunoglobulins

As immunoglobulins are present within blood as complex consortia spanning varied structural forms, targets, immune activities (e.g., effector functions and complement binding affinities), and glycosylation patterns, variations in immunoglobulin populations can serve as strong markers for biological aging. Humans express five immunoglobulin isotypes (IgG, IgA, IgM, IgD, and IgE) spanning multiple subclasses (e.g., IgG1, IgG2, IgA1, etc.) and differing in structure, concentration, biodistribution, and immunomodulatory activity. While IgG, IgA, and IgM are the second, fifth, and ninth highest abundant proteins in serum, each with mg/mL resting levels, IgD and IgE are typically present in serum in μg/mL and ng/mL quantities, respectively.

Total immunoglobulin concentrations tend to peak during early adulthood, and then decrease steadily with age. Nonetheless, only some immunoglobulin isotypes and subclasses exhibit age-dependent changes in serum levels. A recent study (Ritchie et al. *J Clin Lab Anal*, 1998, 12:363-370) identified increases in IgA levels and decreases in IgM levels with age, as well as age-invariance for total IgG concentrations. However, a follow-on study (Lock and Unsworth. *Ann Clin Biochem*, 2003; 40:143-148) determined that, for certain subjects, only IgG1 and IgG3 levels are invariant with age, while IgG2 and potentially IgG4 can exhibit age dependent concentration declines. Contrasting IgA, IgG, and IgM concentration trends, IgD may peak during the first year of life, but remain relatively stable thereafter (Josephs and Buckley, *J Pediatr*, 1980; 96(3): 417-420). For certain subjects, ratios between immunoglobulin isotype and subclass concentrations can provide a strong diagnostic marker for age. For example, the ratio between IgA and IgM, IgA and IgG2, IgA and IgG4, IgM and IgG2, IgM and IgG4, and/or IgG2 and IgG4 serum levels can evidence age.

Immunoglobulin consortia can also exhibit age-dependent changes in glycosylation. All five human isotypes exhibit diverse glycan modifications which affect immunomodulatory and biodistribution behavior. Within each isotype, glycosylation patterns (glycomes) exhibit high degrees of heterogeneity, as well as health and population variance. For example, IgG antibody populations typically exhibit greater than 30 types of glycans at asparagine 297, in addition to variable Fab and hinge region glycosylation, some of which vary with disease status. Nonetheless, age dependent changes in glycosylation patterns have been observed for all five human isotypes. Within IgG antibody populations, increases in agalactosylation and GlcNAc bisection and decreases in digalactosylation, sialylation, and afucosylation are typically observed with aging. Furthermore, there is some evidence that IgG glycosylation is not only responsive to age, but is a determinant for the rate of biological aging (Gudelj et al. *Cellular Immunology*, 2018; 333:65-79).

(iv) Glutathione

Glutathione is a versatile biomolecule which participates in oxidative homeostasis, nitric oxide signaling, aldehyde catabolism, and multiple forms of anabolism. Glutathione is present in micromolar (μM) concentrations in blood as a mixture of reduced monomers and oxidized disulfide dimers. The ratio of these two forms is not only responsive to blood conditions, such as reactive oxygen species levels, but shift with age. Augmenting this effect, systemic glutathione levels steadily diminish with age. As glutathione is critical for mitigating oxidative stress, diminished glutathione levels may be partially responsible for increased oxidative stress and the progression of stress-related conditions (e.g., Parkinson's disease) among elderly individuals. Accordingly, systemic glutathione levels and monomer-dimer ratios can serve as a strong diagnostic marker for biological age. In men and women, serum glutathione concentrations steadily diminish from about 1 μM at the age of 20 to about 0.5 μM at the age of 60 (Yang et al. *J Chromatogr B Biomed Appl*, 1995; 674(1):23-30).

Physical Function and Appearance

In spite of extensive variation in physical fitness and appearance among individuals, diminishing physical abilities and changes in appearance are universal attributes of aging in humans, including diminished strength, diminished ambulation (or walking), and diminished balance.

Methods for Measuring Biological Age

The present disclosure provides a range of methods for ascertaining biological age and biological aging rates with biomarker analysis. Underlying the molecular complexity of aging, a number of species change in predictable manners during aging, and therefore provide metrics for biological and chronological age. As an individual ages, certain biomarkers can include an increase or decrease in concentration, an alteration in state (e.g., glycation of albumin and methylation/demethylation of genomic DNA), a change in form (e.g., isoform ratios of a particular protein), a change in activity, or a combination thereof. Accordingly, as detailed further herein, assessment of one or more of these biomarkers (e.g., identifying concentration, state, form, and/or activity) can be used to determine biological age.

While some biological age measurements can identify a biological age of an individual, others identify biological ages of individual cells, tissues, organs, or systems (e.g., immune or endocrine systems). In many individuals, biological aging progresses in cell-, tissue-, organ-, and/or system-specific manners, reflecting distinct environments, stresses, and genetic and regulatory architectures. In the absence of trauma or aberrant health, the range of biological ages of an individual's tissues and cells is often small, for example less than age measurement experimental error. However, many individuals exhibit multiple, disparate ages. For example, relative to their chronological age, an individual may have a young brain age and advanced immune age. For such an individual, biological age may reflect a sort of median of cell, tissue, organ, and/or system-specific biological ages. Alternatively, the biological age of the individual may be expressed as a set of distinct, organ or system specific biological ages.

A biological age measurement can utilize one biological age marker or a plurality of biological age markers. In many cases, the accuracy of a biological age determination method increases as more age markers are utilized for analysis. However, for many individuals, use of a single age marker or a small set of age markers are sufficient for accurately determining biological age and/or biological aging rate, for example with a standard error of less than 7 years, less than 5 years, or less than 3 years. Examples of methods for assessing biological age are provided in TABLE I.

A method for biological age determination can utilize a single assay or a plurality of assays from TABLE I, a cytokine inflammatory marker panel, a metabolomic assay, peripheral blood mononuclear cell (PBMC) analysis, genomic methylation analysis, inflammatory marker analysis, or a combination thereof. The assay or plurality of assays can assess holistic biological age, organ and/or system-specific biological age, or a combination thereof. The biological age(s) determined for a subject can be used to calibrate a treatment, such as a treatment for aging disclosed herein.

The assay or plurality of assays can be performed at regular intervals, for example once per month, once every three months, once every six months, or once per year. In this way (as well as with aging rate-diagnostic methods), biological age(s) determined from the assay or plurality of assays can also be used to determine biological aging rate in the subject, for example to determine whether an aging treatment is slowing a rate of aging in a subject, to calibrate a treatment method to achieve a target age or aging rate in a subject, to decouple disease markers from aging-related symptoms (e.g., to determine whether raised HbA1c levels stem from disease or aging), or a combination thereof.

TABLE I

Exemplary Age-Measurement Assays

Antibody Assays

Antinuclear Antibody (ANA) Screen (IFA) with Reflex to Titer Assay
Rheumatoid Factor Assay
Thyroid Peroxidase Antibody (Anti-TPO) Assay
Quantitative Immunoglobulin Assay
Proteomic Assays Fibrinogen Assay
Creatinine Kinase Assay
Hemoglobin A1C Assay
Metabolomic Assays Cholesterol, Direct LDL Assay
HDL Cholesterol Assay
Total Cholesterol Assay
Blood Glucose Assay
Other Urine Analysis Antibody Assays A method for determining biological age can include an assessment of antibody concentration, type, and structure. While antibodies are present as complex consortia spanning multiple isotypes (in humans, IgA, IgD, IgE, IgG, and IgM), paratope structures, and processing (e.g., glycanation), changes among these consortia can be diagnostic of biological aging. For example, as further detailed herein, ratios of antibody isotypes typically shift with aging. Furthermore, individual antibody types, such as anti-nuclear and anti-thyroid peroxidase antibodies, change in concentration with age, and can thereby serve as markers for aging. A number of illustrative antibody assays are outlined below. It is contemplated herein that additional antibody assays may be used with methods of the present disclosure.

(i) Anti-Nuclear Antibody Screen

An anti-nuclear antibody (ANA) screen measures cell nucleus-binding antibody concentrations in blood, plasma, or serum. While a range of ANA subtypes are present in humans, most ANA screens measure total ANA antibody concentration, most commonly with indirect immunofluorescence and enzyme-linked immunosorbent (ELISA) detection following cell binding (e.g., to HEp-2 cells). ANAs are associated with a range of disorders, many of which are associated with aging. However, even among healthy individuals, ANA blood concentrations tend to increase with age, with elderly individuals often exhibiting 3- or greater-fold ANA levels relative to younger individuals (Xavier et al. *Mech Aging Dev,* 1995; 78(2):145-54). Accordingly, a method consistent with the present disclosure can utilize a blood ANA concentration measurement to determine biological age or biological aging rate.

(ii) Rheumatoid Factor Assay

An age-diagnostic method can assess blood (e.g., whole blood, serum, plasma) levels of rheumatoid factor (RF) factor, an autoantibody against the Fc portion of IgG and implicated in a number of age-related conditions, including rheumatoid arthritis and diminished bone density. While rheumatoid factor can present as a combination of immunoglobulin isotypes (e.g., IgA, IgD, IgE, IgG, and IgM) with ranges of Fc epitopes and binding affinities, total rheumatoid factor levels can be identified with a number of binding assays, including indirect immunofluorescence and enzyme-linked immunosorbent (ELISA). In most people, Rheumatoid factor typically appears between the age of 30 and 70 and progressively increases in concentration with age. Accordingly, a method for measuring biological age consistent with the present disclosure can include measuring blood RF concentration.

(iii) Thyroid Peroxidase Antibody Assay

A thyroid peroxidase antibody assay measures concentration of autoantibodies which target thyroid peroxidase (TPO), an enzyme essential for thyroid hormone production. As thyroid peroxidase is the typically the most prevalent thyroid autoantigen, thyroid peroxidase antibody levels can be reflective of total anti-thyroid antibody levels. While thyroid antibodies (including thyroid peroxidase antibodies) are implicated in a number of diseases, thyroid antibody levels also tend to increase spontaneously with age (Chen et al. *Endocrinology,* 2010; 151(9):4583-4593), thereby allowing them to serve as markers for biological aging. Accordingly, a method of the present disclosure can utilize blood thyroid antibody and/or blood thyroid peroxidase antibody levels to determine biological age. Furthermore, in some subjects, the targets of thyroid peroxidase antibodies shift with age, with anti-domain A antibodies typically increasing in prevalence (Czarnocka et al. Clin Endocrinol (Oxf), 1998; 48(6):803-8).

(iv) Quantitative Immunoglobulin Assay

A quantitative immunoglobulin assay can assess total antibody levels in a subject sample. Typically, quantitative immunoglobulin assays measure total antibody levels in blood. However, some assays assess concentration by antibody isotype or subtype. For example, a quantitative immunoglobulin assay may measure total IgG and IgA concentrations, or may separately determine concentrations of individual antibody subtypes (e.g., IgG1, IgG2, IgA1, IgA2, etc.). As in many subjects, total antibody, antibody isotype, and antibody subtype concentrations change with age (Crisp and Quinn. *Allergy Asthma Proc,* 2009; 30(6):649-54), quantitative immunoglobulin assays can be used to determine biological age.

(v) Glycanation Assays

Biological aging can be evidenced by immunoglobulin glycosylation profiles. All five human antibody isotypes exhibit glycosylation patterns. While the positions of glycosylation are partially isotype dependent, the types of oligosaccharides, or glycans, which couple at these positions can affect antibody localization, subcellular partitioning, aggregation, and Fc and complement receptor affinities. Furthermore, these glycation patterns can be reflective of age, environment, and health status. For example, IgG galactosylation often decreases with age, while fucosylation, sialylation, and bisection can respond to age in a gender-specific manner (Gudelj et al. *Cellular Immunology,* 2018; 333:65-79). Accordingly, a method can utilize an antibody glycanation profile to assess biological age.

In addition, a glycanation assay for use in assessing biological age is currently marketed as the Glycanage test.

Proteomic Assays

Humans are estimated to have between 20 thousand and 5 million proteins, depending in part on structural variant classifications (e.g., whether splicing variants constitute distinct proteins), such that proteomic shifts with aging and changes in health status are often complex. Nonetheless, as proteins participate in and regulate the majority of biological processes, changes in physiology, including those associated with aging, are often reflected in protein expression and activity. To this point, changes in the human proteome with age are thought to include both drivers of (e.g., diminished superoxide dismutase and catalase activity) and responses to (e.g., increased fibrinogen concentration) biological aging. Changes in the human proteome with age include up- and downregulation of individual proteins, as well as proteome-wide changes in abundances, ratios, and activity levels. Despite the complexity of the human proteome, a number of proteins are known to change with aging in detectable manners. Accordingly, a method for determining biological age can include measuring the abundance, state, distribution, modification, or activity of an individual protein or collection of proteins. In many such cases, the method includes measuring the concentrations of a small number of blood proteins.

However, a method for determining biological age can also take a broad, proteomic view to assess biological age. As human blood contains over 5000 types of proteins, aggregate analysis of tens, hundreds, or thousands of proteins can often correlate small proteomic shifts to biological age, even in the absence of statistically significant individual protein biomarkers. Advances in high-throughput proteomic analysis, such as in liquid chromatography-mass spectrometry, protein sequencing, and multiplexed immunoassays, can enable rapid quantification of hundreds or thousands of proteins from individual samples.

(i) Fibrinogen Assays

Fibrinogen activity and blood level often changes with age. Fibrinogen is blood-based glycoprotein complex which polymerizes to fibrin to facilitate blood clotting. While fibrinogen levels can be responsive to health and inflammation, baseline fibrinogen levels typically increase with age, rising by about 250 µg/mL per decade, or from about 2.2 mg/mL to about 3.2 mg/mL from the age of 25 to the age of 65 in many individuals (Hager et al. *Aging (Milano),* 1994; 6(2):133-8). As elevated fibrinogen levels are associated with a number of age-related conditions, including increased cardiovascular disease susceptibilities and diminished kidney and liver function, fibrinogen levels often correlate with many recognizable, qualitative aspects of aging.

Fibrinogen assays typically assess at least one of fibrinogen activity and concentration. Fibrinogen activity is typically measured indirectly with blood clotting tests, such as thrombin and prothrombin time tests, thromboelastometry, and qualitative clotting assays. However, these assays can have limited ability to distinguish between low fibrinogen levels and diminished fibrinogen activity. Alternatively or in addition to activity analyses, some assays directly measure blood fibrinogen concentration, with a wide range of immunoassays commercially available for such measurements.

(ii) Creatinine Kinase Assays

Changes in the creatine system, which furbishes muscle cells with phosphocreatine for rapid energy production, can reflect aging, with creatine and associated metabolite levels typically decreasing with aging. Nonetheless, creatinine, the primary breakdown product of phosphocreatine catabolism, typically increases in blood concentration with age. This discrepancy is likely due to diminished capacity for creatinine recycling and clearance. Creatinine kinase, an intramuscular enzyme which converts creatinine back into phosphocreatine for further use, diminishes in concentration with age, leading to higher levels in creatinine in blood, muscles, and some extravascular spaces. Accordingly, blood and muscle creatinine kinase levels can be effective for determining biological age.

(iii) Hemoglobin A1c Assays

During circulation, hemoglobin can promiscuously couple to blood glucose in a process referred to as glycation. While the baseline rate for glycation is typically low, hyperglycemia, hormonal insensitivities, and aging can enhance glycation rate, leading to higher concentrations of glycated hemoglobin. One of the most prevalent forms of the resultant glycated hemoglobin is HbA1c (also referred to as hemoglobin A1c), which contains glucose attached at one or both (3-peptide N-terminal valines. While high levels of HbA1c are most commonly ascribed to hyperglycemia in diabetes, changes in glucose tolerance and glycemic regulation with aging tend to increase HbA1c baselines irrespective of health status, leading to age-related shifts in HbA1c populations which can be small (for example 5.4% to 5.6% from the age of 25 to greater than 65), but nonetheless significant. When corrected for health and environmental factors, HbA1c levels can be diagnostic for biological age (Masuch et al. *BMC Endocrine Disorders,* 2019; 19, 20). HbA1c can be measured with a variety of techniques, including quantitative chromatography (e.g., by high-performance liquid chromatography), immunoassays, and capillary electrophoresis.

(iv) Cytokine and Inflammatory Marker Panels

A method for assessing biological age can include analysis of one or more cytokines. In many cases, the biological age assessment includes determination of one or more blood cytokine concentrations. Often referred to as inflammaging, aging often coincides with increased blood cytokine levels through increased cytokine production and diminished anti-inflammatory responses. Central to this process, a number of pro-inflammatory markers, such as C-reactive protein and serum amyloid A, increase by multiple-fold levels through middle and advanced age, often leading to an imbalance between pro- and anti-inflammatory cytokines. As these changes in cytokine levels often foster chronic inflammation, weakened immune states, and diminished energy metabolism (Salvioli et al. *Current Pharmaceutical Design,*

2006; 12:3161-71), cytokine imbalance is likely both a cause and effect of aging. Accordingly, blood cytokine concentrations can be correlated with progressive age-related changes in cytokine levels to assess biological age.

A method for determining biological age can include measuring blood concentrations of one or more cytokines. While a blood concentration of a single cytokine can be sufficient for determining biological age, in many cases the method includes measuring blood concentrations of multiple cytokines. As non-limiting examples, a method for determining biological age can assess levels of one or more of C-reactive protein, soluble tumor necrosis factor receptor 1 (sTNF1), soluble tumor necrosis factor receptor 2 (sTNF2), tumor necrosis factor α (TNF-α), interleukin-1 α (IL-1α), interleukin-1 β (IL-1β), interleukin-6 (IL-6), and interleukin-10 (IL-10), all of which typically increase in concentration with age (Salvioli et al.; Glossop et al. *Arthritis Research & Therapy,* 2005; 7:R1227). Among these cytokines, C-reative protein, TNF-α, IL-1α, IL-10, IL-6, and IL-10 are implicated in increased proinflammatory responses with aging, and may play roles in atherosclerosis, and insulin insensitivity, among other conditions (Salvioli et al.), while sTNF1 and sTNF2 likely aggravate arthritis (Glossop et al.). Accordingly, blood concentrations of one or more cytokines can evidence aging and age-related symptoms.

In addition, a test for inflammatory changes in the context of biological age (i.e. an inflammatory age test) is currently marketed as the iAge test.

Expression of certain cell surface proteins may be associated with inflammatory processes as well including CD16, CD25, CD27, CD38, CD57, CD80, HLADR, IgM, KIR, KLRG1, NK1, NKg2a, and TIGIT. These cell surface proteins may be measured and quantified using flow cytometry.

Metabolomic Assays

As metabolism encompasses the biochemistry of growth, energy production and consumption, and certain forms of signaling, age-related changes are often reflected by metabolomic shifts. As with proteomic analysis, metabolomic profiling can query individual biomolecules which are responsive to aging, can broadly profile portions of a subject's metabolome (e.g., by profiling tens, hundreds, or thousands of metabolomic biomarkers), or can include a combination thereof. Owing to a higher number of available metabolites and lower variance than cell and tissue profiling, metabolomic analysis often focuses on blood metabolites. As over 18000 metabolites have been identified in human blood (Adav and Wang. *Aging Dis,* 2021; 12(2):646-661), a biological age measurement could, in theory, accurately determine biological age with a broad, non-targeted profiling approach, even in the absence of a strong diagnostic aging marker. However, a number of age diagnostic studies have identified robust metabolite biomarkers, which, alone or in combination with other measurements, can accurately measure biological age.

(i) Total Cholesterol Assays

Cholesterol is complexed in a variety of lipid-protein macromolecular structures, commonly referred to as lipoproteins, for transport through the blood. Although lipoproteins differ in terms of a number of properties, including size, composition, and receptor affinities, in humans, lipoproteins are divided into five major classes based primarily by on densities. High-density lipoproteins (HDL) tend to have the lowest volumes and highest protein and phospholipid contents of the five classes of lipoproteins, with diameters typically ranging from 5-15 nm, densities of greater than 1.063 g/mL, and protein accounting for approximately ⅓ of their mass. Low-density lipoproteins (LDL) tend to have slightly lower masses of between about 1.019 and 1.063 g/mL, slightly larger diameters of about 18-28 nm, and higher cholesterol content approaching nearly 50% (by mass). Intermediate-density lipoproteins (IDL), tend to have densities of between 1.006 and 1.019 g/mL, similar cholesterol content as high-density lipoproteins, and diameters ranging from 25 to 50 nm. Very low-density lipoproteins (VLDL) are usually characterized as having densities of between 0.95 and 1.006 g/mL, relatively low protein content (typically about 10% by mass), and diameters of between about 30 and 80 nm. Finally, chylomicrons, the largest lipoproteins, typically have densities below 0.95 g/mL, protein content below 2% (by mass), and diameters ranging from 75 to 1200 nm.

Cholesterol analysis often distinguishes between at least some lipoprotein types when assessing cholesterol levels. For example, lipid panels typically distinguish between HDL and LDL-bound cholesterol, and sometimes further distinguish VLDL, IDL, and chylomicron cholesterol content. However, for many conditions, total blood cholesterol content is sufficient for accurate diagnosis.

In particular, for some individuals, total cholesterol content can be indicative of biological age. In men, blood cholesterol levels tend to steadily increase from about 1.6 mg/mL at the age of 18 to about 2 mg/mL at the age of 50, after which time blood cholesterol levels tend to drop by about 0.05 mg/mL every decade. Slightly more punctuated trends tend to be observed in women, with blood cholesterol levels typically increasing from about 1.7 to 2.1 mg/mL between the ages of 18 and 60, and then plateauing or declining at a slower rate than in men through advanced aging (Yi et al. *Scientific Reports,* 2019; 9:1596). Accordingly, a method disclosed herein can use blood cholesterol level to determine biological age.

A number of enzymatic, chemical, electrochemical, and spectroscopic methods can be used to determine cholesterol levels. Commonly, cholesterol, either pooled or collected from a lipoprotein fraction, is coupled to a chromophore or fluorophore through its C3-hydroxyl, and quantitated spectrophotometrically (Li et al. *Journal of Food and Drug Analysis,* 2019; 27(2):375-386).

(ii) Cholesterol, Direct LDL Assays

In many individuals, low-density lipoprotein (LDL), one of the primary carriers for cholesterol in blood, increases in concentration through middle age, and then remains stable or decrease with advanced aging (McAuley and Mooney. *Med Hypotheses,* 2017; 104:15-19). In men, LDL tends to plateau between 50 and 60 years of age, whereas in women, this trend is prolonged, with maximum concentrations typically occurring between 60 and 70 years of age (Kreisberg and Kasim, 1987; 82(1): 54-60). Although often requiring corrections for certain factors, such as estrogen levels in women, LDL levels can be a powerful metric for biological age. Accordingly, a method for determining biological age can include determining an LDL level of a subject.

Often, LDL is simultaneously measured along with other lipids and lipoproteins as part of lipid profiles or panels. In some panels, LDL is indirectly identified through total cholesterol measurements. An LDL measurement can identify LDL, LDL-cholesterol (LDL-C, the amount of cholesterol contained within low-density lipoproteins), or both. As cholesterol is primarily carried within LDL, high-density lipoproteins (HDL), and very low-density lipoproteins (VLDL), LDL levels are often determined without measuring LDL, but rather by subtracting non-LDL abundances from a measured level of cholesterol. For example, lipid panels in the United States commonly estimate LDL levels by subtracting measured HDL and triglyceride levels from measured total blood cholesterol.

LDL can also be measured directly. In many cases, these methods involve separation of LDL from other lipoproteins and lipids, including HDL, VLDL, and lipoprotein a (Lp(a)). Common methods for achieving these separations include centrifugation (e.g., ultracentrifugation) which can separate lipoproteins and lipids by density; electrophoresis, which can separate lipoproteins and lipids based on size and charge; precipitation, in which lipoproteins and/or lipids are selectively drawn from solution; by homogeneous methods, which utilize combinations of conditions, binding molecules, and polymers to separate lipoprotein fractions; and by combinations thereof. The separated lipoproteins and lipids can then be quantified with a range of enzymatic, electrochemical, chemical, and spectroscopic methods (Nauck et al. *Clinical Chemistry,* 2002; 48(2):236-254).

(iii) Cholesterol, Direct HDL Assays

Similar to LDL, HDL levels tend to decrease in concentration with advanced age. Complicating the relationship between HDL and aging, low HDL may correlate with mortality, potentially obfuscating otherwise reliable trends in lowered HDL abundance with age (Walter, *Arteriosclerosis, Thrombosis, and Vascular Biology,* 2009; 29:1244-1250). Nonetheless, a number of studies have defined clear decreases in HDL as a function of age, especially among males (Ferrara et al. *Circulation,* 1997; 96:37-43). Accordingly, HDL levels, alone or in combination with other cholesterol data (e.g., LDL, total cholesterol, etc.), can be used to assess biological age.

As with LDL-cholesterol, HDL-cholesterol is typically measured through separation followed by cholesterol quantification. However, a number of methods (in particular some homogeneous methods) allow HDL-cholesterol to be measured simultaneously with other forms of cholesterol.

(iv) Blood Glucose Assays

In many individuals, aging coincides with increased resting and post-meal glucose levels. As blood glucose levels are responsive to multiple age-sensitive regulatory mechanisms, including insulin and incretin sensitivities, and can contribute to age-related developments, such as increase HbA1c and albumin glycation, blood glucose levels can capture a broad spectrum of aging-related progressions, and can serve as reliable diagnostic markers for aging. In men and women, resting and post-meal glucose levels tend to increase at rates of about 7 to 11 µg/mL per decade, while 2-hour-post-meal levels tend to increase by a more pronounced rate of 56-66 µg/mL per decade (Chia et al. *Circulation Research,* 2018; 123(7):886-904). Following from these trends, blood glucose levels (either resting, post-meal, or a combination thereof) can be used to determine biological age.

A number of cheap methods are available for blood glucose measurement. Most commonly, blood glucose is detected through enzymatic (e.g., through hydrogen peroxide generation by glucose oxidase) or chemical oxidation.

Urine Analysis

While water, urea, and sodium chloride account for greater than 96% of its mass, urine contains a complex mixture of chemicals which can acutely reflect age, health and environment. Over 450 species of microbiota and 3000 molecules have been identified in urine, of which 480 have not been detected in blood (Bouatra et al. *PLoS One,* 2013; 8(9):e73076). Many of the molecules in urine are waste materials, including biproducts of metabolism and damaged and solubilized biomolecules. Accordingly, age-related changes within a subject, in particular their kidney, liver, and bladder ages, are often reflected in urine composition (Harpole et al. *Expert Rev Proteomics,* 2016; 13(6):609-626).

Peripheral Blood Mononuclear Cell Analysis

A method for determining biological age can include peripheral blood mononuclear cell (PBMC) analysis. PBMCs include blood cells with round nuclei, such as T lymphocytes, B lymphocytes, natural killer cells, and monocytes (and contrasting non-nucleated cells, such as erythrocytes, and cells with monolobed nuclei such as granulocytes). A number of PBMC phenotypic distributions have been shown to shift with age. In certain individuals, T cell populations shift from CD28+ towards CD95+ with age, suggesting reduced proliferation and increase apoptosis (Li et al. *J Int Med Res,* 2020; 48(7)). Furthermore, aging often coincides with increased monocyte and regulatory T cell and decreased naïve T cell populations (Huang et al. *PNAS,* 2021; 118(33):e2023216118). Accordingly, PBMC populations and subpopulation polarization can be used for biological age analysis. Such analysis may include PBMC immunophenotyping, for example to identify T lymphocytes, B lymphocytes, and natural killer cells, as well as CD4, CD8, CD28, naïve, effector, and central memory cell subpopulations. As an illustrative example, PBMCs can be isolated from whole blood, and characterized with flow cytometry, for example as outlined in Li et al.

Flow cytometry may also be combined with fluorescent conjugated antibodies so that in addition to identifying certain cell types, cell surface proteins may be identified and/or quantified as well. Types of cell surface markers (i.e. proteins located on a cell surface) found on cells in blood that may be identified and quantified using flow cytometry include CD16, CD25, CD27, CD38, CD57, CD80, HLADR, IgM, KIR, KLRG1, NK1, NKg2a, and TIGIT. Types of cells that may have these markers include white cells and specifically lymphocytes, neutrophils, monocytes, basophils, and eosinophils. For example, T lymphocytes may include one or more of cell surface markers that may be identified and/or quantified using flow cytometry.

Cellular Senescence Assay

A biological age measurement can include senescent cell population analysis. While cellular senescence is characterized by arrested growth and termination of cell division, senescence coincides with changes in cellular phenotypes. Senescent phenotypes are not only adverse for cellular function, generally inducing lower levels of fitness (e.g., diminished energy metabolism and elevated oxidative stress), but also tend to coincide with deleterious secretory behavior, such proinflammatory exosome production, and senescence-associated secretory phenotype (SASP) secretion behavior. Exemplifying this point, a recent mouse model experiment demonstrated that as few as $1/10{,}000$ senescent cells in healthy adult mice are sufficient for causing systemic disfunction, metabolic stress, and accelerated aging (Xu et al. *Nat Med,* 2018; 24(8):1246-1256). Accordingly, cellular senescence is not only harmful to senescent cells, but can accelerate aging and aggravate aging symptoms in disparate cells within an organism.

Senescence phenotypes typically affect detectable changes in expression profile. At a cellular level, non-terminally differentiated senescent cells can often by identified by their inability to replicate or undergo DNA synthesis. On a genetic level, senescent cells can also typically be identified based on their altered regulation of proliferation-associated and growth inhibitory genes (Itahana et al. Methods to Detect Biomarkers of Cellular Senescence. In Methods in Molecular Biology: Biological Aging: Methods and Protocols. Jumana Press Inc.). However, senescent cells are most commonly identified by senescence-associated markers, which can include upregulation of the lysosome-associated protein β-galactosidase (Dimri et al. *Proc. Natl. Acad. Sci*, 1995; 92: 9363-9367); the DNA damage response marker H2AX (Campisi, *J. Annu. Rev. Physiol*, 2013 75:685-705); tumor suppressors p16ink4a, p21, and p53 (Rufini et al. *Oncogene*, 2013; 32: 5129-5143); and altered secretory profiles (for example increased proinflammatory cytokine production, Itahana et al.).

A marker associated with the cellular senescence comprises senescence-associated beta-galactosidase ("SA-β-gal") which can be measured in blood and used as a measure of cellular senescence.

Genomic Methylation Assays

DNA methylation is a prevalent epigenetic modification which can strongly affect expression, and correspondingly phenotype, in a subject. Recent studies have demonstrated that aging coincides with genome-wide DNA methylation and demethylation, with a greater prevalence of demethylation than methylation during most human lifespans. While total genomic methylation can correlate with age, a number of recent studies have identified specific sites which can serve as aging markers based on methylation or hydroxymethylation status (Salameh et al. *Front. Genet.*, 2020; 10). Accordingly, a method of the present disclosure may determine methylation status at a site or plurality of sites in genomic DNA to ascertain biological age.

Inflammatory Marker Analysis

In some cases, inflammatory markers can be used to assess biological age in a subject. As used herein, an inflammatory marker can be a species which causes or increases in concentration in response to inflammation. Inflammation tends to increase with age, often diminishing immune function, contributing to frailty, and augmenting conditions such as arthritis, asthma, atherosclerosis, and certain forms of dementia. Nonetheless, only some inflammation-related markers increase in concentration with age. For example, a recent study identified Chemokine (C-X-C motif) ligand 9 (CXCL9), EOTAXIN, macrophage inflammatory protein (Mip-1α), LEPTIN, IL-1β, interleukin-5 (TL-5), interferon-α (IFN-α), interleukin-4 (IL-4), TNF-related apoptosis-inducing ligand (TRAIL), interferon-7 (IFN-7), Chemokine (C-X-C motif) ligand 1 (CXCL1), interleukin-2 (TL-2), transforming growth factor-α (TGF-α), plasminogen activator inhibitor (PAI)-1, and leukemia inhibitory factor (LIF) as potential biomarkers for inflammation, while other inflammatory response markers, such as TL-6 and TNF-α, have minimal association with aging (Sayed et al. *Nature Aging*, 2021; 1: 598-615). Stemming from this type of observation, a method of the present disclosure can utilize one or more inflammatory markers to determine biological age.

Safety Analysis

An aging treatment disclosed herein can be combined with a safety or health assessment. In addition or alternatively to monitoring biological age in a subject receiving treatment for aging, one or more markers for health can be monitored to ensure treatment efficacy, to provide a calibrant for age measurement, or a combination thereof. Some aging treatments can cause adverse effects, such as diminished red blood cell (RBC) count or diminished liver function in certain subjects. Monitoring health prior to or concurrently with an aging treatment can allow the treatment to be tailored to the subject, can determine whether a subject is suitable for an aging treatment, and can ensure that the treatment is modified or ceased following an adverse response.

Furthermore, in some cases, markers for overall health can be important for determining biological age. As many age markers fluctuate in response to health status, calibration to a subject's health can be requisite for accurate biological age assessments. For example, certain conditions can increase autoantibody concentrations by greater degrees than aging, rendering such autoantibody analyses effective for only certain subjects. Nonlimiting examples of health assessments are outlined in TABLE II. A subject of an aging treatment can be assessed with one or with a plurality of health assessments outlined in TABLE II or otherwise consistent with methods disclosed herein.

TABLE II

Complete Blood Count (CBC) Assay
Total Protein Assay
Liver Function Assay
Blood Urea Nitrogen (BUN) Assay
Creatinine Assay
C-Reactive Protein (CRP) Assay (i) Blood-Based Assays A subject of an aging treatment method, before, during, and/or following the treatment, can be assessed with a complete blood count (CBC) assay. Complete blood count assays typically quantitatively measure multiple components of blood, such as red blood cells, white blood cells, hemoglobin and platelets, as well as health and aging factors, such as red blood cell to plasma ratios. In addition to screening for overall health, complete blood count assays can identify adverse responses to some aging treatments, such as blood diffusion-based anemia.

Analogously, a subject of an aging treatment can be assessed with a total protein test to determine protein levels in a biofluid (e.g., blood). While some total protein tests quantify specific proteins, such as albumin and globulin concentrations and/or ratios (e.g., with immunoassays), others determine total protein concentration in the biofluid (e.g., based on the 280 nm protein band in a spectrophotometric absorbance assay). Total protein tests can identify some potential side effects of aging treatments, including fatigue, edema, and nutritional deficits.

Liver function assays can test for a number of substances indicative of proper liver function and health. Many liver function assays determine blood levels for liver-based or secreted enzymes, including alanine transaminase, aspartate transaminase, alkaline phosphatase, albumin, and gamma-glutamyltransferase. A liver function assay can also assess levels of metabolites regulated (e.g., cleared) by the liver, such as bilirubin, a major heme degradation product. A liver function assay can also determine a quality of blood, such as pH or prothrombin time (how quickly blood clots). A specific set of assessments included in a liver function assay can depend on the health of the subject, as well as the type of aging treatments and diagnostics to which they are subjected.

A blood urea nitrogen (BUN) assay can assess kidney and metabolic function in a subject receiving an aging treatment. Blood urea nitrogen assays measure urea levels in blood. Blood-based ureas, which primarily derive from protein degradation, are maintained at low levels by kidney filtration. In addition to improper kidney function, high blood urea levels can indicate dehydration (a risk associated with some blood dilution methods), internal bleeding, and shock.

Creatinine assays provide an additional form of assessment for kidney function. Creatinine assays measure concentrations of creatinine, a catabolic waste product, in blood. While kidneys typically filter and thus maintain low levels of creatinine in blood, this function is hindered by a number of conditions which are identifiable with creatinine assays. In certain subjects, use of a creatinine assay can be important for monitoring kidney health prior to, during, or following an aging treatment.

C-reactive protein (CRP) assays can serve as a measure for inflammation and infections in a subject of an aging treatment. As some aging treatments increase susceptibility to infection, C-reactive protein assays can be important measures for aging treatment efficacy and subject health.

Methods for Performing Plasmapheresis

Treating and Preventing the Effects of Aging Using Plasmapheresis

The term "plasmapheresis" as used herein is interchangeable with the term "therapeutic plasma exchange," and plasmapheresis is a form of apheresis wherein some amount of a plasma of an individual is withdrawn from the body of the individual and removed. Plasmapheresis methods are described herein for treating and/or preventing a symptom or a condition associated with aging. In treating and/or preventing a symptom or a condition associated with aging, the plasmapheresis methods described herein may also increase lifespan and promote longevity.

A plasmapheresis treatment typically comprises—and begins with—the withdrawing of whole blood from an individual receiving the plasmapheresis treatment. Whole blood that is withdrawn is separated into a cellular fraction and a plasma fraction. The term "cellular fraction" as used herein can refer to or comprise red blood cells, white blood cells, and platelets. The terms "plasma fraction" or "plasma" as used herein can refer to or comprise a liquid portion of whole blood which contains, among other things, proteins, electrolytes, vitamins, and hormones. Typically, in a plasmapheresis treatment, the plasma fraction that is separated is removed while the cellular fraction is returned to the individual receiving the plasmapheresis treatment. As used herein in the context of plasmapheresis administration (or any other type of apheresis procedure), the terms "withdraw," "withdrawal," "withdrawn," and "withdrawing" (or any other conjugation of "withdraw") means to draw blood out (actively or passively) from the vascular system of an individual receiving plasmapheresis (or other type of apheresis procedure) which may be achieved using any suitable vascular access, which includes but is not limited to peripheral intravenous lines and central lines. As used herein in the context of plasmapheresis administration (or any other type of apheresis procedure), the terms "return" or "returning" (or any other conjugation of "return") or "infuse," or "infusing" (or any other conjugation of "infuse") means to return blood back (actively or passively) to the vascular system of an individual receiving plasmapheresis (or other type of apheresis procedure) which may be achieved using any suitable vascular access. As used herein in the context of plasmapheresis administration (or any other type of apheresis procedure), the terms "remove," "removal," "removed," and "removing" (or any other conjugations of "remove") means to remove at least a portion of whole blood withdrawn from an individual receiving plasmapheresis (or any other apheresis procedure) and not returning the at least portion of the whole blood to the individual receiving plasmapheresis so that it is removed from their body. As used herein, in the context of plasmapheresis (or any other apheresis procedure), the terms "separate," "separated," or "separating" (or any other conjugation of "separate") means to separate apart components of blood from one another. For example, in plasmapheresis, whole blood is withdrawn and plasma is separated from the cellular fraction of the withdrawn whole blood. As used herein, the term "plasmapheresis" may be combined with other terms such as "therapy" (i.e. plasmapheresis therapy) or "treatment" (i.e. plasmapheresis treatment) or "procedure" (i.e. plasmapheresis procedure) and, unless otherwise indicated, no specific meaning should be attributed to the use of one of these terms or the other in the context in which they appear. Of note, the term "plasmapheresis" is often used interchangeably with therapeutic plasma exchange and at other times it is used to denote a form of therapeutic plasma exchange where less plasma is removed than that removed in therapeutic plasma exchange. To avoid confusion with respect to terminology, the term plasmapheresis is used throughout, and, as stated, as used herein the term therapeutic plasma exchange is interchangeable with the term plasmapheresis. However, in no way should the term plasmapheresis be deemed to be limiting on the scope of the disclosure found herein which may be relevant to different types of apheresis based on context.

A plasmapheresis therapy session may begin with the initial step of withdrawing whole blood from a blood vessel of a patient using an apheresis device. Apheresis devices are well known and are machines configured to carry out procedures including plasmapheresis. Apheresis devices may be configured to withdraw whole blood from an individual through an intravenous line, separate the whole blood into components, and return an infusion to the individual through an intravenous line. The infusion returned to the individual may include separate components which may include blood that has had the plasma component removed from it. In addition, an infusion given to the individual may include an exchange fluid as well. An apheresis device can be an ex vivo apheresis system or machine comprising one or more centrifugal chambers. An ex vivo apheresis system or machine can also comprise a return flow controller and one or more sensors for monitoring plasma or blood density. An apheresis device can also be configured to deliver an anticoagulant to the patient during the procedure. In some embodiments, the anticoagulant can be citrate dextrose. It should, however, be understood that any method or device for carrying out plasmapheresis is suitable for use with the methods and formulations described herein and the description provided should not be deemed to limit the inventive methods or formulations described herein which are suitable for use with any device or method for carrying out plasmapheresis.

An exchange fluid is typically administered with plasmapheresis wherein the exchange fluid is administered to the individual receiving plasmapheresis intravascularly (i.e. through intravenous access; e.g. peripheral or central line) during the plasmapheresis treatment. An exchange fluid may comprise any fluid that is suitable for use in intravenous fluid administration. For example, non-limiting examples of fluids suitable for intravascular administration with the administration of plasmapheresis as described herein are commonly referred to as isotonic fluids and include Normal Saline (i.e. a 0.9% saline solution) and Lactated Ringer's. An exchange fluid solution suitable for use in plasmapheresis as described herein may further include albumin such as human albumin. For example, an exchange fluid may comprise a normal saline solution that includes 5% albumin by weight. Typically, a source of albumin is human derived albumin also referred to as human serum albumin (HSA). As an example, an exchange fluid suitable for use with plasmapheresis may comprise a sterile liquid preparation comprising an amount of human-derived protein in the amount of 50 g per 1000 ml of the sterile liquid preparation wherein at least 96% of the human-derived protein is human serum albumin protein. Besides the human-derived serum albumin protein, the remainder of the HSA preparation can comprise a saline solution and small amounts of potassium, N-acetyl-DL-tryptophan, caprylic acid, or a combination thereof. A 5% HSA preparation of an exchange fluid can be an FDA-approved 5% HSA preparation. More specifically, the 5% HSA preparation can be manufactured by an FDA-approved procedure such as the Cohn-Oncley cold ethanol fractionation procedure followed by ultra-filtration and pasteurization. Replacing plasma withdrawn from an individual receiving plasmapheresis with 5% HSA is useful for regulating and stabilizing the volume of circulatory blood within the individual.

An exchange fluid may be mixed or combined in any suitable way with the cellular fraction of the whole blood that is withdrawn during plasmapheresis, which remains after separation of plasma and which is returned to the individual receiving plasmapheresis during the procedure. An exchange fluid suitable for use with plasmapheresis may also include one or more therapeutics. For example, a therapeutic that reduces inflammation may be provided with plasmapheresis by, for example, mixing the therapeutic with an exchange fluid. An exchange fluid for plasmapheresis may also comprise or be mixed together one or more blood products (i.e. not including the cellular fraction that is returned) including but not limited to fresh frozen plasma and platelets. It should be understood, that when mixed with an exchange fluid, therapeutics and blood products will to at least some degree be withdrawn back from the individual receiving the plasmapheresis and as such it may be beneficial to administer or infuse a therapeutic and/or blood product after completing the blood withdrawal from the individual so that the therapeutic and/or blood product will not be withdrawn from the individual during the plasmapheresis therapy.

As stated, in a typical plasmapheresis procedure, a volume of whole blood is withdrawn from an individual and a portion of it is returned to the individual along with an exchange fluid. Typically, the exchange fluid is returned to the individual simultaneously with the withdrawal of the whole blood which makes calculations related to the plasmapheresis process not entirely simple and straightforward.

Typically, as stated above, exchange fluid is infused to the individual receiving plasmapheresis simultaneously with withdrawal of the whole blood and removal of the plasma so that the exchange fluid is essentially reconstituting some of the plasma volume during the procedure, and it is not, therefore, possible to remove the entire plasma volume during a typical plasmapheresis procedure because, to some degree, plasma is being continuously replenished as it is being removed. As used herein, "plasma volume" refers to the entire volume of plasma within the whole blood of an individual, which can be calculated using numerous methods that are well known for calculating plasma volume. In a typical plasmapheresis procedure, a volume of plasma that is equal to about 1 plasma volume is removed from the individual receiving plasmapheresis or 1 plasma volume up to 1.5 plasma volumes may be removed in a typical plasmapheresis procedure. Typically, during a plasmapheresis administration as described herein, an amount of exchange fluid is returned to the patient that is essentially equal to the amount of plasma volume that is withdrawn from the patient so that the removed plasma volume (that is not returned to the patient) is "exchanged" with the exchange fluid that is returned to the patient and replaces the volume of plasma that is removed. While the exchange fluid in some embodiments may be more or less than the plasma volume removed, again, typically it is essentially equal in volume. For example, where one plasma volume is removed from an individual in a method described herein, a volume of exchange fluid equal (or essentially equal) to one plasma volume is returned to the individual.

As explained, because exchange fluid is simultaneously infused to an individual during a plasmapheresis procedure, removing anywhere from 1-1.5 plasma volumes during a plasmapheresis procedure does not typically mean that the plasma (and its contents) are completely removed even though a volume equal to 1-1.5 plasma volumes is removed, because the removed volume includes exchange fluid that had been infused to the individual and then removed as part of the total volume removed. According to Winters (*Hematology Am Soc Hematol Educ Program,* 2012; 2012(1):7-12), in a typical plasmapheresis treatment where 1-1.5 of plasma volume exchanged, approximately 60%-70% of substances present in the plasma at the start of plasmapheresis will be removed which means that approximately 30-40% of substances present in the plasma at the start of plasmapheresis will remain in the body of the individual receiving plasmapheresis following a typical single plasmapheresis treatment.

Depending on the weight of the individual receiving plasmapheresis, the volume of plasma removed can be between approximately 2 L to 4 L. When 2 L to 4 L of plasma is removed during plasmapheresis, the volume of whole blood that is withdrawn from the patient is necessarily greater than 2.0 L to 4.0 L, which is to say that the withdrawn whole blood volume contains the volume of plasma to be removed and therefore the whole blood volume withdrawn is necessarily always larger than the volume of plasma that is removed. It should be understood that plasma volume in an individual is dependent on a number of factors including weight and gender and so 2 L to 4 L is used here only as a non-limiting example of a range of plasma that might be removed in a plasmapheresis procedure. plasmapheresis, in some instances may involve removal of less than 2 L of plasma or more than 4 L of plasma.

Blood can be withdrawn from a blood vessel of the patient including a peripheral blood vessel, a central blood vessel, or a combination thereof. Since the blood flow from the patient into the apheresis device has to be steady and preferably faster than 50 mL/min, the site of vascular access is typically a blood vessel capable of withstanding high negative pressure without collapsing.

Moreover, a site of vascular access for receiving an exchange fluid or a mixture that includes an exchange fluid and one or more other components is typically another blood vessel (or another peripheral or central access point) capable of tolerating relatively high positive pressure. In some embodiments of the methods described herein, whole blood can be withdrawn using a large-bore needle or cannula from a patient's peripheral vein such as the antecubital fossa, the basilica vein, or the cephalic vein. Additionally, if determined by a plasmapheresis provider to be an optimal vascular access point, whole blood can also be withdrawn by cannulation of a radial artery of an individual receiving plasmapheresis. If determined by a plasmapheresis provider to be an optimal vascular access point, whole blood can be withdrawn using an intravascular or implantable device such as a central venous catheter (CVC), an arteriovenous (AV)

shunt, an AV fistulae, or a port-CVC. For example, whole blood can be withdrawn from an internal jugular vein, a subclavian vein, or a femoral vein or artery of the individual receiving plasmapheresis. Blood from an individual receiving plasmapheresis can be withdrawn at a rate of approximately 90 ml/min. However it is also suitable, in the methods described herein, that blood from an individual receiving plasmapheresis be withdrawn at a rate of between approximately 90 ml/min and 135 ml/min. It should be understood that, under certain conditions, withdrawal at a rate of less than 90 ml/min or more than 135 ml/min may be optimal for the individual receiving plasmapheresis. As previously discussed, typically, a site of vascular access for receiving a fluid to be returned to an individual receiving plasmapheresis, which may comprise, for example, an exchange fluid, a cellular fraction, a therapeutic, or a blood product and mixtures thereof, is different from a site of vascular access for initial blood withdrawal. For example, a cannula or catheter extending from or otherwise coupled to an apheresis device can be used to deliver a fluid to be returned to an individual receiving plasmapheresis comprising a cellular fraction and an exchange fluid to a blood vessel in an arm, hand, neck, or chest of an individual receiving plasmapheresis.

In some embodiments of the methods described herein, each plasmapheresis treatment session can last approximately 90 minutes to 2 hours. However, it should be understood that plasmapheresis session length can be varied based on the objective of the plasmapheresis treatment and sessions shorter than 90 minutes or longer than 2 hours are suitable with the methods and formulations described herein. In addition, a plasmapheresis treatment session duration can vary depending on certain factors associated with the individual receiving the plasmapheresis including but not limited to the weight of the individual receiving the plasmapheresis or the overall health of the individual.

In an exemplary method for administering plasmapheresis to an individual, a plasmapheresis method can comprise one or a plurality of plasmapheresis therapies. A plasmapheresis method can begin with the step of identifying an individual in need of a plasmapheresis treatment. The treatment method can further comprise withdrawing whole blood from a blood vessel of the individual receiving plasmapheresis using an apheresis device or other technique for withdrawing blood. The plasmapheresis method can further comprise separating the whole blood withdrawn into a cellular fraction and a plasma fraction using the apheresis device or other technique for separating blood components. The plasmaphersis method can further comprise infusing back to the individual receiving plasmapheresis an exchange fluid and the cellular fraction while removing the plasma fraction from the individual. An amount of exchange fluid returned to the individual may be approximately equal to an amount of plasma that is removed. For example, if one plasma volume is removed from an individual receiving plasmapheresis, in certain methods described herein, an amount of an exchange fluid returned to the individual will also be approximately equal to one plasma volume. Alternatively, an amount of exchange fluid returned may also exceed the amount of plasma volume removed. For example, if one plasma volume is removed, more than one plasma volume may be infused back to the individual receiving the plasmapheresis.

Factors involved in aging are located within the plasma of a patient and therefore, using the innovative plasmapheresis methods described herein, the factors involved with aging are removed from the body of an individual receiving plasmapheresis with removal of plasma from the body of the individual.

As explained, aging is likely a multifactorial process that currently has not been fully elucidated, which has generally precluded development of effective therapies to treat and prevent the effects of aging. However, while the entire pathophysiology of aging may not yet be completely clear, there are clear choke-points in the pathophysiology of aging where the innovative methods described herein are effective. For example, it is understood that factors that affect aging including cytokines and peptides associated with aging can all be found in plasma. As used herein "plasma content" describes all of the separate components of plasma, and we know that at least some of the plasma content has components in it that affect aging (even if we don't know what they are specifically within the plasma content). The presence of these aging factor or factors within the plasma, makes the plasma a potential choke point of the aging process because these targeted aging-related factor or factors must necessarily travel through the vascular system within plasma in order to get to the cells and/or tissue upon which they act, and, therefore, these factor or factors can be effectively collected and removed from the vascular system choke point using the innovative methods described herein. Even if it is not necessarily known which factor or factors found in blood are to be targeted by an age-related therapy, removing all of the plasma content or as much as is possible using the innovative methods and formulations described herein also necessarily removes the factor or factors that affect aging from the body and therefore diminishes or prevents the aging activity that removed factor or factors are associated with.

As already explained, a plasmapheresis session typically removes about 60-70% of plasma content which means that about 30-40% of the plasma content in the body of the individual receiving a typical single plasmapheresis treatment, including those factors associated with aging, remain within the blood of the individual receiving plasmapheresis after a single plasmapheresis treatment.

In certain methods described herein, a plasmapheresis protocol removes more plasma than is removed in a typical single plasmapheresis treatment so that more than 60-70% of the plasma content of an individual receiving plasmapheresis is removed from the body of the individual. For example, in certain methods described herein, a first plasmapheresis treatment may remove 60-70% of plasma content of an individual and the individual then undergoes an additional plasmapheresis treatment within a window of time relative to the first plasmapheresis treatment so that the first plasmapheresis treatment together with the additional plasmapheresis treatment achieves a cumulative removal of plasma greater than 60-70%. In these embodiments, the additional plasmapheresis treatment is administered before the plasma that is removed from the individual who received the plasmapheresis is fully replenished in the blood of the individual who received the plasmapheresis. In these embodiments, a plasmapheresis therapy method as described herein may be carried out and then a subsequent plasmapheresis therapy method as described herein may be carried out a time that is within 72 hours of the initial plasmapheresis therapy. Similarly, a plasmapheresis therapy method as described herein may be carried out and then an additional plasmapheresis therapy method as described herein may be carried out a time that is within 48 hours of the initial plasmapheresis therapy. For example, a plasmapheresis therapy method as described herein may be carried out and then an additional plasmapheresis therapy method as described herein may be carried out a time that is within 24 hours of the initial plasmapheresis therapy. Similarly, in these methods, an additional plasmapheresis treatment may also be carried out within a window of time where an additional plasmapheresis treatment in an individual is within four days, within five days, within six days, within seven days, within 8 days, within 9 days, within 10 days, within 11 days, within 12 days, within 13 days, or within 14 days of an initial plasmapheresis treatment in the individual.

Other approaches to achieving as much removal of plasma content as is possible include withdrawing more than 1.5 times of the plasma volume in a single plasmapheresis session. For example, a method for performing plasmapheresis as described herein includes withdrawing 1.5 times the plasma volume of an individual receiving plasmapheresis in a single plasmapheresis treatment. For example, a method for performing plasmapheresis as described herein includes withdrawing 1.6 times the plasma volume of an individual receiving plasmapheresis in a single plasmapheresis treatment. For example, a method for performing plasmapheresis as described herein includes withdrawing 1.7 times the plasma volume of an individual receiving plasmapheresis in a single plasmapheresis treatment. For example, a method for performing plasmapheresis as described herein includes withdrawing 1.8 times the plasma volume of an individual receiving plasmapheresis in a single plasmapheresis treatment. For example, a method for performing plasmapheresis as described herein includes withdrawing 1.9 times the plasma volume of an individual receiving plasmapheresis in a single plasmapheresis treatment. For example, a method for performing plasmapheresis as described herein includes withdrawing 2 times the plasma volume of an individual receiving plasmapheresis in a single plasmapheresis treatment. Likewise, a method for performing plasmapheresis as described herein may include withdrawing 2 or more times the plasma volume of an individual receiving plasmapheresis in a single plasmapheresis treatment.

In each case where a high percentage of plasma content is removed, clotting factors and/or platelets may be infused back to the individual receiving the plasmapheresis to replenish the clotting factors and platelets removed with the plasma content to address any elevated bleeding risk post the plasmapheresis treatment due to removal of the clotting factors and platelets.

A "plasmapheresis regimen" as used herein includes within its scope any application of plasmapheresis as described herein for the treatment or prevention of aging and/or promotion of longevity. A plasmapheresis regimen may include one or more treatments carried out over a particular time period and may in certain implementations include therapeutics provided together with plasmapheresis.

In the innovative methods described herein, plasmapheresis may be used in a plasmapheresis regimen in order to remove a relatively large amount of plasma content from an individual receiving plasmapheresis. In certain plasmapheresis regimens, plasmapheresis may be administered on a twice a week schedule to achieve a cumulative effect with respect to plasma content removal as described herein with the time period between a first and a second plasmapheresis treatment being delivered to an individual within 24 hours of each other (including within the same day), within 36 hours of each other, within 48 hours of each other, within 60 hours of each other, within 72 hours of each other, within 84 hours of each other, within 96 hours of each other, within 108 hours of each other, within 120 hours of each other, within 134 hours of each other, within 156 hours of each other, or within 168 hours of each other. An additional plasmapheresis treatment may also be carried out within a window of time where an additional plasmapheresis treatment in an individual is within four days, within five days, within six days, within seven days, within eight days, within nine days, within ten days, within eleven days, within twelve days, within thirteen days, or within fourteen days of an initial plasmapheresis treatment in the individual.

A plasmapheresis regimen as described that is carried out twice a month may be performed every week in a month for a total of eight plasmapheresis treatments per month, every other week for a total of four plasmapheresis treatments per month, or once a month for a total of two treatments in a month. A plasmapheresis regimen as described herein with twice weekly treatments may be carried out for 6 months in total of twice weekly treatments. Within that 6 month period the twice weekly treatments may all be carried out with the same amount of time between each of the two weekly treatments or the amount of time may be varied between the two weekly treatments.

A plasmapheresis regimen as described herein may comprise performance of plasmapheresis once per week. For example, a plasmapheresis regimen as described that is carried out once a month may be performed once a week every week in a month for a total of four plasmapheresis treatments per month, every other week for a total of two plasmapheresis treatments per month, or once a month for a total of one treatment in a month. Any plasmapheresis regimen as described herein with once weekly treatments may be carried out for 6 months in total.

In certain plasmapheresis treatments described herein, any subsequent plasmapheresis treatment session can be undertaken only after 24 days have passed since the last plasmapheresis treatment session. In these and other embodiments, the entire treatment method can cease after 125 days have passed since the first plasmapheresis treatment session. The treatment method can also comprise continuing the treatment method by repeating the method when at least 24 days have passed since the last treatment session. In these embodiments, no plasmapheresis treatment sessions should occur during this intervening waiting period. For example, the various plasmapheresis treatment sessions can be separated by 24 days, 25 days, 26 days, 27 days, 28 days, 29 days, or any combination thereof. The various plasmapheresis treatment sessions can be separated by the same number of days or be separated by a differing number of days. As a more specific example, the first plasmapheresis treatment session can be separated by the second plasmapheresis treatment session by 24 days and the second plasmapheresis treatment session can be separated by the third plasmapheresis treatment session by 25 days or 26 days. In other example methods, the first plasmapheresis treatment session can be separated by the second plasmapheresis treatment session by 26 days and the second plasmapheresis treatment session can be separated by the third plasmapheresis treatment session by 25 days or 24 days. In some embodiments, the treatment method can cease entirely when 125 days have passed since the first treatment session. In other embodiments, the treatment method can cease when at least six plasmapheresis treatment sessions have been undertaken, regardless of the number of days passed since the first plasmapheresis treatment session. In additional embodiments, the treatment method can cease when at least seven or at least eight plasmapheresis treatment sessions have been undertaken, regardless of the number of days passed since the first plasmapheresis treatment session. In another treatment method for performing plasmapheresis, the treatment method can comprise six (6) plasmapheresis treatment sessions in total. The first plasmapheresis treatment session can occur on the first day (day 1) of the treatment, the second plasmapheresis treatment session can occur on the twenty-fifth day (day 25) of the treatment method, the third plasmapheresis treatment session can occur on the fiftieth day (day 50) of the treatment method, the fourth plasmapheresis treatment session can occur on the seventy-fifth day (day 75) of the treatment method, the fifth plasmapheresis treatment session can occur on the one-hundredth day (day 100) of the treatment method, and the sixth plasmapheresis treatment session can occur on the one-hundred and twenty-fifth day (day 125) of the treatment method. In this embodiment, no plasmapheresis treatment sessions occur during the intervening periods between the aforementioned treatment sessions. In other embodiments, a plasmapheresis treatment regimen may extend as long as needed and include as many separate sessions/treatments as needed to achieve one or more measurable effects.

With respect to the use of plasmapheresis in the treatment of aging and aging related conditions, an anti-inflammatory or other immune-modulating therapeutic may be used together with plasmapheresis treatment in a synergistic way. More specifically, an anti-inflammatory or immune-modulating therapeutic may synergistically modulate, reduce, or eliminate the effect of inflammatory and immune cells and factors (e.g. cytokines) that remain in the blood following plasmapheresis treatment and thereby further reducing the effect of these cells and factors. In certain of the methods described herein, a therapeutic is administered to target an aspect of aging found within blood of an individual receiving the plasmapheresis treatment. For example, inflammation is a known part of the aging process and is sometimes referred to as "inflammaging" wherein effects of aging correlate with an elevated level of inflammatory agents within the blood. As such, an anti-inflammatory delivered together with plasmapheresis can act to reduce inflammatory activity and as such disrupt the effect of inflammation in age related conditions. With plasmapheresis in particular, there's a strong synergy in that using the methods described herein most of the non-cellular inflammatory factors found within the plasma content are removed from the body of the individual receiving the plasmapheresis treatment and any remaining inflammatory cells may be further affected with therapeutics. As such, in the example provided, with a single typical plasmapheresis about 30-40% of the inflammatory factors within the plasma content will remain after the single typical plasmapheresis treatment and if an anti-inflammatory or other immune-modulator is administered with or soon after plasmapheresis is performed, the anti-inflammatory or other immune-modulator can act synergistically with the removal of the inflammatory factors to further attenuate the effect of the inflammatory cells and factors remaining after the plasmapheresis treatment. Applying a therapy in this targeted way creates a cumulative inhibition effect that increases the benefit to the individual receiving the plasmapheresis.

A plasmapheresis treatment as described herein can further comprise delivering a therapeutically-effective dosage of intravenous immunoglobulin (IVIG) to a blood vessel of the individual receiving the plasmapheresis treatment. In certain plasmapheresis treatments as described herein, IVIG is delivered to an individual receiving plasmapheresis after returning the cellular fraction and the exchange fluid to the individual receiving the plasmapheresis. This is to say that a therapeutically-effective dosage of IVIG may be provided to an individual separately from infusion of the cellular fraction and the exchange fluid to the individual receiving the plasmapheresis. For example, IVIG may be infused in the individual receiving plasmapheresis after a plasmapheresis treatment is completed so that any infused IVIG will not be removed in the plasmapheresis process. It is also possible to administer IVIG concurrently with the administration of plasmapheresis.

The therapeutically-effective dosage of IVIG can be approximately 2.0 g of IVIG per kg of bodyweight of the individual receiving plasmapheresis. The IVIG delivered can contain certain antibodies and cytokines which can have a positive effect on the immune system of the individual receiving plasmapheresis and may contribute to establishing an optimal systemic environment for cell growth. As stated above, it is suitable for administration of a therapeutic such as IVIG mixed together with an exchange fluid and/or a cellular fraction during a portion of the plasmapheresis procedure when blood is being withdrawn or it is also suitable to administer IVIG to the individual as part of a method for administering plasmapheresis as described herein when blood is no longer being withdrawn from the individual receiving plasmapheresis. The therapeutically-effective dosage of IVIG can be any FDA-approved IVIG or immune globulin intravenous (IGIV) infusion or preparation. For example, the IVIG can comprise primarily of gamma globulins.

The steps described do not require the particular order shown to achieve the desired result. Moreover, certain steps or processes may be omitted or occur in parallel in order to achieve the desired result.

Each of the plasmapheresis treatment sessions can comprise the steps of withdrawing whole blood from a blood vessel of a patient using an apheresis device, separating the whole blood withdrawn into a cellular fraction and a plasma fraction using the apheresis device, admixing the cellular fraction with an exchange fluid comprising albumin derived from human plasma, returning the mixture comprising the cellular fraction and the exchange fluid to the blood vessel of the patient using an apheresis device, and delivering a therapeutically-effective dosage of intravenous immunoglobulin (IVIG) to the blood vessel of the individual receiving plasmapheresis after returning the mixture comprising the cellular fraction and the exchange fluid to a blood vessel of the individual.

A biological age or any other measurable feature or marker of the efficacy of plasmapheresis on an individual may be measured using the numerous markers and assays described herein. In particular, a biological age, physiological measurement (e.g. strength, walking, or balance), mental assessment (e.g. an emotional wellness survey), or marker in the blood of the individual (e.g. cell surface marker) that is measured using any of the analysis techniques, markers, and assays described herein may be used in conjunction with a plasmapheresis regimen as described herein wherein a biological age, physiological measurement, mental assessment, or marker that is identified, quantified, or determined to be present is used to affect a modification in a plasmapheresis regimen.

For example, a biological age, physiological measurement, mental assessment, or marker in the blood of an individual may be measured, using any of the markers and/or assays described herein, before and after a plasmapheresis regimen as described herein (including one or more plasmapheresis treatments over a period of time) and the plasmapheresis regimen may be extended if a decrease (or increase if an increase and not a decrease is beneficial with respect to the item that is measured) in the biological age, physiological measurement, mental assessment, or marker in the blood of the individual (as measured before the regimen is administered) is not achieved. The plasmapheresis regimen can then be continued until the decrease (or increase if an increase and not a decrease is beneficial with respect to the item that is measured) in the biological age, physiological measurement, mental assessment, or marker that is sought is achieved.

Similarly, biological age, a physiological measurement, a mental assessment, or a marker found in the blood of an individual can shape the plasmapheresis regimen itself, wherein, for example, a biological age, a physiological measurement, a mental assessment, or a marker in the blood of an individual is measured before and after a single plasmapheresis therapy and subsequent plasmapheresis therapies are administered until the biological age is decreased below a level that is sought.

In an exemplary method, a plasmapheresis method can begin with the step of identifying an individual in need of a plasmapheresis therapy. A blood sample is taken from the individual, either before initiation of the plasmapheresis, or from the whole blood that is withdrawn and used to determine a biological age of the individual using the markers and/or assays described herein. In some embodiments, physiological and mental assessment is carried to assess one or more of the individual's strength, walking, balance, or mental status (wherein exemplary techniques for obtaining these measurements are described herein such as in the section below describing the pilot study and results). The plasmapheresis method can further comprise withdrawing whole blood from a blood vessel of the individual receiving plasmapheresis using an apheresis device or other technique for withdrawing blood. The plasmapheresis method can further comprise separating the whole blood withdrawn into a cellular fraction and a plasma fraction using the apheresis device or other technique for separating blood components. The treatment method can further comprise infusing back to the individual receiving plasmapheresis an exchange fluid and the cellular fraction while removing the plasma fraction from the individual. An amount of exchange fluid returned to the individual may be approximately equal to an amount of plasma that is removed. For example, if one plasma volume is removed from an individual receiving plasmapheresis, in certain methods described herein, an amount of an exchange fluid returned to the individual will also be approximately equal to one plasma volume. Alternatively, an amount of exchange fluid returned may also exceed the amount of plasma volume removed. For example, if one plasma volume is removed, more than one plasma volume may be infused back to the individual receiving the plasmapheresis. Once the plasmapheresis therapy is completed, a second sample is obtained and a second biological age is determined using the markers and/or assays described herein. Should one or more of the biological age, physiological measurement, mental assessment, or marker found in the blood of the individual be determined after the plasmapheresis therapy not to have been lowered or raised sufficiently (as compared to the biological age, physiological measurement, mental assessment, or the marker determined before the start of the plasmapheresis therapy), additional plasmapheresis therapy is administered with repeated sampling and measuring of biological age, physiological measurement, mental assessment, or the marker with the plasmapheresis continuing until the biological age, physiological measurement, mental assessment, or the marker is decreased by an amount that is sought.

Also described herein is a method for treating aging by carrying out a blood dilution. As described herein, plasma content can be removed and exchange fluid added. The removal of plasma content (even with partial replacement) together with the addition of exchange fluid typically lowers the concentrations of one or more constituents of plasma in an individual receiving plasmapheresis treatment. Essentially, solute (the plasma content) is decreased while the solvent (the liquid portion of plasma replaced by the exchange fluid) remains the same. In this way, in addition to removing plasma content components, the methods described herein dilute one or more components of plasma content that remain in the blood of the individual receiving plasmapheresis following a plasmapheresis treatment.

Plasma content dilution can achieve synergistic affects to removal of plasma content alone in that, at least, dilution causes the plasma composition of an individual receiving plasmapheresis to resemble a plasma composition of a biologically younger individual. This is to say that factors found in plasma that are associated with aging are found empirically to have a lower concentration in younger individuals than older individuals. As in a younger individual where the aging-associated factors found in plasma are less active, the decrease in concentration of the plasma content in individuals receiving plasmapheresis as described herein lowers the relative activity further of the factors associated with aging in those individuals receiving the plasmapheresis therapy as described herein.

(i) Modeling Blood Dilution

A number of models may be used to calculate an amount of dilution that is achieved with a plasmapheresis treatment as described herein. For example, Reverberi and Reverberi (*Blood Transfus*, 2007; 5(3):164-174) provide formulas for modeling residual plasma analyte concentrations from which Formulas (I), (Ia), and (Ib) are derived:

$$\text{Residual Solute Concentration} = 100\% * e^{-\frac{v_p * n}{v_b}} \quad \text{(I)}$$

wherein $v_p$ is plasma volume, n is number of plasma volume units exchanged, and $v_b$ is total blood volume (i.e. whole blood volume).

As an illustrative example of Formula (I), using a plasma volume of 3 L, 1 plasma volume to be exchanged, and a total volume of 5 L of whole blood would be expected to result in a residual plasma content concentration of approximately 54% of the original concentration following a single plasmapheresis treatment. For the same plasma volume and total volume of blood but a plasma exchange of 1.5 plasma volumes, the residual solute concentration would be approximately 40%.

Typically, plasma analytes exhibit an instantaneous concentration drops following blood exchange, followed by reconcentration along a logarithmic-like trends to pre-blood dilution levels. Formula (I) can be modified to Formula (Ia) to estimate plasma analyte levels $n_d$ days following plasma exchange, assuming a half-time $t_{1/2}$ for the analytes to return to pre-blood dilution levels:

$$\text{Residual Solute Concentration} = 100\% * \left(1 - \left(\frac{1}{2}\right)^{\frac{n_d}{t_{1/2}}} e^{-\frac{v_p * n}{v_b}}\right) \quad \text{(Ia)}$$

Noting that not all plasma analytes reestablish homeostasis at equal rates, as typical plasma analytes return to pre-blood dilution levels after about 10 days, $t_{1/2}$ of 3 to 4 days is often a suitable estimate. Once again using 3 L, 1 plasma volume, and 5 L of whole blood with a half-life of 3 days and measured 3 days after the initial plasmapheresis treatment, the residual solute concentration increases from approximately 54% following the plasmapheresis treatment to approximately 72% three days (i.e. 72 hours) later.

Winters (cited above) provides the following simplified formula: $Y/Y0=e^{-x}$, where Y is the final concentration of a substance, Y0 is the initial concentration, and X is the number of times the patient's plasma volume is exchanged. Continuing with the approximately 72% residual concentration calculated above using Formula (Ia), if plasmapheresis is administered once again 72 hours after the initial plasmapheresis, Y0=72%, x=1, and Y=26.5% residual plasma concentration following the second plasmapheresis treatment.

Formula (Ia) can further be used to determine the degree of plasma analyte clearance following multiple rounds of plasma exchanges by setting n as above. For such an application, Formula (Ia) can be estimated as a sum, expressed as Formula (Ib), where each plasma exchange event, i, is attenuated by analyte regeneration over $n_{di}$ days following the plasma exchange event:

$$\text{Residual Solute Concentration} = 100\% * \left(1 - \sum_i \left(\frac{1}{2}\right)^{\frac{n_{di}}{t_{\frac{1}{2}}}} e^{-\frac{v_p}{v_b}}\right) \quad \text{(Ib)}$$

This equation does not account for diminished plasma exchange efficacy over multiple cycles, reflecting exchange of partially diluted plasma. However, in cases where $t_{1/2}$ is approximately equal to or less than the time between plasma exchange events, and for therapies with limited numbers of plasma exchanges, discrepancies from this estimation are typically small.

Formulas (I), (Ia), (Ib), and the formula provided by Winters all provide excellent and useful approximations of dilution levels which are suitable for use with the methods described herein. It is also noted that if higher accuracy in calculating plasma content dilution should be achieved, the following factors and issues should also be considered: First, many plasma separation methods only partially separate plasma from cellular components. While multiple rounds of separation can increase efficiencies, single iterations of centrifuge-based plasma separation and membrane-based plasma separation typically achieve 80% and 30% plasma separation efficiencies (Williams and Balogun. *Clin J Am Soc Nephrol*, 2014; 9(1): 181-190). For a 500 mL blood draw, which will typically contain about 55% (275 mL) plasma these efficiencies translate to 220 mL plasma removed by centrifugation and 82.5 mL plasma removed by filtration. The effect of incomplete plasma separation from cellular components is a concomitant decrease in plasma exchange efficiency. If plasma is centrifugally separated from blood with 80% efficiency, then plasma exchange will typically be 80% efficient given a volume of blood separated and exchanged. Second, many plasma components actively exchange into spaces outside of the vasculature. While a typical adult male human has about 5 liters of blood, the majority of fluids, and analogously, analytes, are contained in interstitial and intracellular spaces, which account for about 10.5 and 28 liters of fluid, respectively. As used herein, intracellular spaces can include all volumes contained within cell membranes of an organism, including all fluids within these spaces, while interstitial spaces can denote spaces surrounding tissues. Many plasma analytes actively equilibrate between the blood and these spaces, such that fractions of their total populations are contained within the blood at any given time. Removal of such species by plasma exchange can be attenuated by their partitioning outside of the blood. For example, only about 60% to 70% of IgG1 immunoglobulins are present in the blood at any given time, such that plasma exchange can only target 60% to 70% of the IgG1 population. Furthermore, disruption of homeostasis, for example through blood dilution, can affect osmotic gradients which draw species into blood from extravascular spaces, thereby hastening return to pre-treatment blood analyte levels. Third, plasma analytes regenerate at a range of rates. Following a blood composition altering event, such as blood dilution, blood analyte concentrations tend to return to their original, resting levels. Although blood dilution can alter resting levels of individual blood analytes (for example lowered blood triglyceride levels as outlined in Dehal and Adashek. *Case Rep Med*, 2018; 2018: 4017573), diluted species tend to increase in concentration while concentrated species (e.g., albumin provided from a high concentration exchange fluid) tend to decrease in concentration to reestablish pre-dilution levels. While some species (in particular many cytokines) exhibit complex re-equilibration patterns, many follow simple exponential growth or decay curves. However, the rates of these processes can vary significantly between species. For example, IgG immunoglobulins often return to pre-blood dilution levels in about 4 days (Harris et al. *Journal of Scleroderma and Related Disorders*, 2018; 3(2):132-152), while low-density lipoproteins can take more than 2 weeks to return to resting levels (McGowan. *Journal of Clinical Lipidology*, 2013; 7(3):S21-S26).

May et al. (*Am J Clin Pathol*, 1989; 91(6):688-94) presents a model which accounts for extravascular compartmentalization and species regeneration. This model, adapted as Formula (II) below, captures rates of plasma analyte loss through plasma exchange and clearance:

$$A_t = A_0 * e^{\left[-\frac{(r+k_1)t}{V_p}\right]} + \frac{V_p k_2 \left[1 - e^{\left[-\frac{(r+k_1)t}{V_p}\right]}\right]}{r + k_1}, \quad \text{(II)}$$

wherein $A_t$ denotes a plasma analyte concentration at time t, $A_0$ denotes the initial concentration of the analyte, $k_1$ denotes a rate of clearance of the analyte (e.g., through degradation, biliary clearance, etc.), and $k_2$ denotes a rate at which the analyte is released from extracellular tissues. The May et al. model does not account for regeneration of the analyte, and further assumes plasma analyte distribution according to a two-compartment system (intravascular and extravascular). Accordingly, the model may not be appropriate for analytes dynamically exchanged across multiple compartments (e.g., antibodies with appreciable endosomal and interstitial concentrations), or analytes which are rapidly produced following dilution. However, this model can be corrected for inefficient plasma removal during exchange, as outlined above, through correction to clearance rate ($k_1$).

Human Pilot Study Results

An IRB approved pilot study was carried out to assess the effect of plasmapheresis on aging in human participants. The study included eight human participants over the age of 50 (in chronological years) who each received six plasmapheresis treatments over a three month period. Three of the eight treated participants were female and five were male. In addition, a group of three participants each received three sham plasmapheresis treatments over three months and served as controls for the eight participants who each received six plasmapheresis treatments. All three participants who received sham treatments were male.

The administration of the plasmapheresis treatments was overseen by a licensed physician using Spectra Optia plasma cell separators manufactured by Terumo BCT, Inc., and FDA approved for that purpose. Plasmapheresis was administered in a clinical setting to the eight participants receiving the plasmapheresis treatment so that during each of the six plasmapheresis treatments at least one plasma volume was exchanged with an exchange fluid comprising 5% albumin over 2-3 hours. The three sham patients, used as controls, were given the appearance of receiving plasmapheresis in a clinical setting but did not actually receive plasmapheresis.

Data that was collected and analyzed included macro data and micro data. macro data included measures of strength, balance, walking, and mental and emotional wellbeing. micro data included blood studies that measured and quantified cell surface markers associated with aging.

Macro Data

For the macro data, each participant had data collected before each of their six plasmapheresis treatments. This included measures of strength, balance, walking, and mental and emotional wellbeing. For strength, hand grip strength was measured using a grip strength measuring device. For balance, the participants were asked to stand and balance on one leg and the total time they were able to stand on the one leg was recorded for a maximum time of 120 seconds. For walking, the participants stood from a seated position and walked a set distance and the total time it took the participant to stand and walk the distance was recorded. For mental and emotional wellbeing the participants answered questions from the SF-12 survey, a recognized large-data-developed quality-of-life questionnaire consisting of questions that measure emotional and mental health.

FIG. 1 shows multiple graphs of macro data for a first participant ("PT1") in the pilot study who is female and who received six treatments of plasmapheresis. PT1 had macro data collected before each one of her six plasmapheresis treatments. The exchange fluid of PT1 included 2 grams of IVIG for each plasmapheresis treatment that PT1 received. The graphs of FIG. 1 are titled to indicate which macro data they present. For each of the five graphs shown in FIG. 1, the x-axis has numbers 1 through 6 indicating a time before each of the six plasmapheresis treatments when data was collected. For the graph titled "PT1 Hand Grip", the y-axis shows the measurements of grip strength in units of Kg measured with a standard grip strength device. As can be seen, PT1's measured hand strength increased overall over the course of the six treatments. For the graph titled "PT1 Up&Go" the y-axis is the time in seconds that it took PT1 to stand from a seated position and walk a fixed distance that PT1 walked each of the six times that the measurement was taken (each participant tested also walked the same distance). As can be seen, PT1's time to walk the distance decreased between the first measurement and the last measurement indicating an improvement. For the graph titled "PT1 Balance" the y-axis is the time in seconds that PT1 was able to stand with one leg raised and where the maximum time measured was 120 seconds. As can be seen, PT1 was able to stand the maximum measured time throughout the duration of the study. For the graph titled "PT1 SF-12 Physical Health" the y-axis represents an SF-12 survey score for subjective physical health. As can be seen, PT1 showed an overall improvement in scores over the course of the six treatments. For the graph titled "PT1 SF-12 Emotional Health" the y-axis represents an SF-12 survey score for subjective emotional health. As can be seen, PT1 showed an overall improvement in scores over the course of the six treatments.

Figure 2:
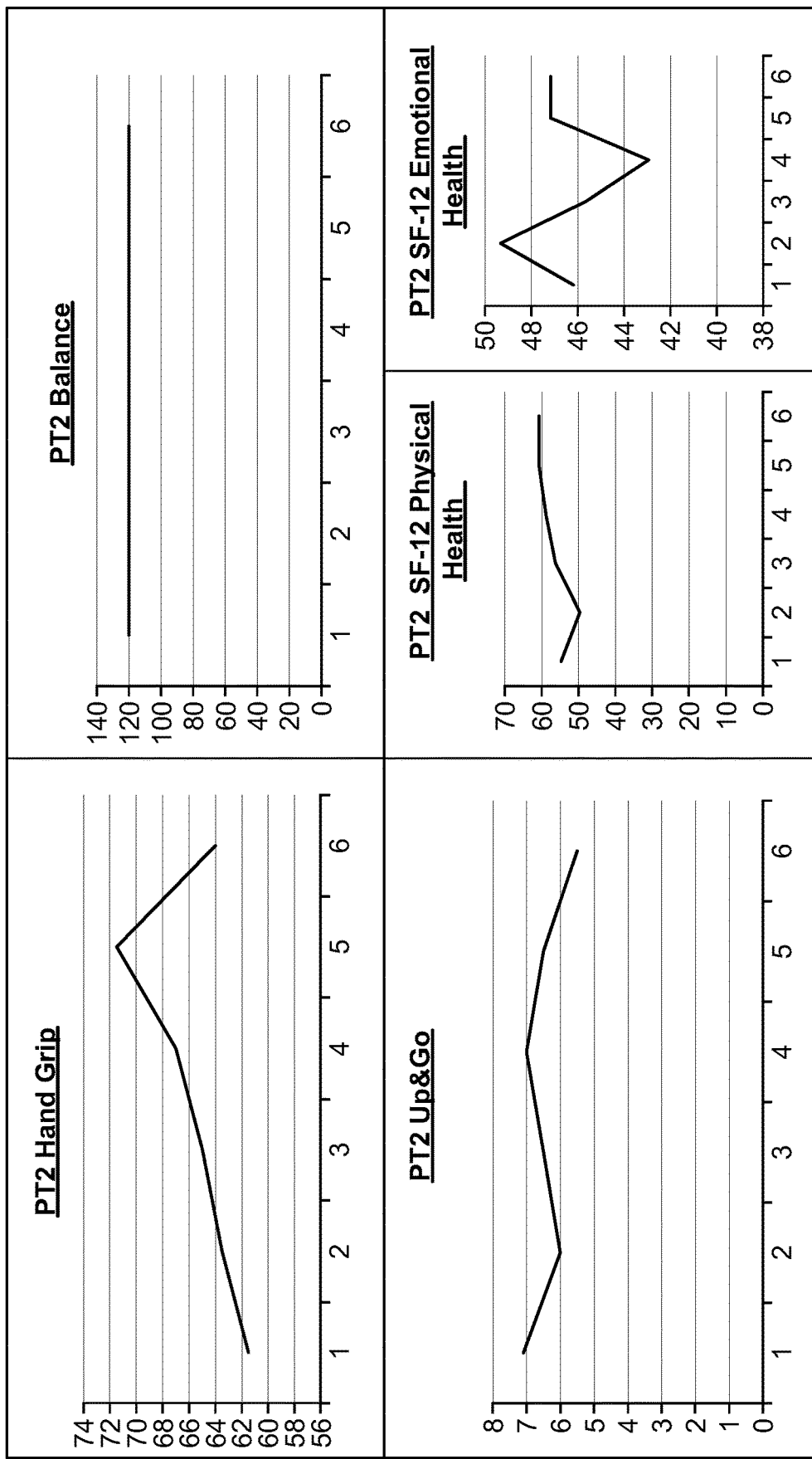
FIG. 2 is a series of graphs of physical, and mental macro data for a male collected over the course of six plasmapheresis treatments.

FIG. 2 shows multiple graphs of macro data for a second participant ("PT2") in the pilot study who is male and who received six treatments of plasmapheresis. PT2 had macro data collected before each one of his six plasmapheresis treatments. The graphs of FIG. 2 are titled to indicate which macro data they present. For each of the five graphs shown in FIG. 2, the x-axis has numbers 1 through 6 indicating a time before each of the six plasmapheresis treatments when data was collected. For the graph titled "PT2 Hand Grip", the y-axis shows the measurements of grip strength in units of Kg measured with a standard grip strength device. As can be seen, PT2's measured hand strength increased overall over the course of the six treatments. For the graph titled "PT2 Up&Go" the y-axis is the time in seconds that it took PT2 to stand from a seated position and walk a fixed distance that PT2 walked each of the six times that the measurement was taken (each participant tested also walked the same distance). As can be seen, PT2's time to walk the distance decreased between the first measurement and the last measurement indicating an improvement. For the graph titled "PT2 Balance" the y-axis is the time in seconds that PT2 was able to stand with one leg raised and where the maximum time measured was 120 seconds. As can be seen, PT2 was able to stand the maximum measured time throughout the duration of the study. For the graph titled "PT2 SF-12 Physical Health" the y-axis represents an SF-12 survey score for subjective physical health. As can be seen, PT2 showed an overall improvement in scores over the course of the six treatments. For the graph titled "PT2 SF-12 Emotional Health" the y-axis represents an SF-12 survey score for subjective emotional health. As can be seen, PT2 showed an overall improvement in scores over the course of the six treatments.

Figure 3:
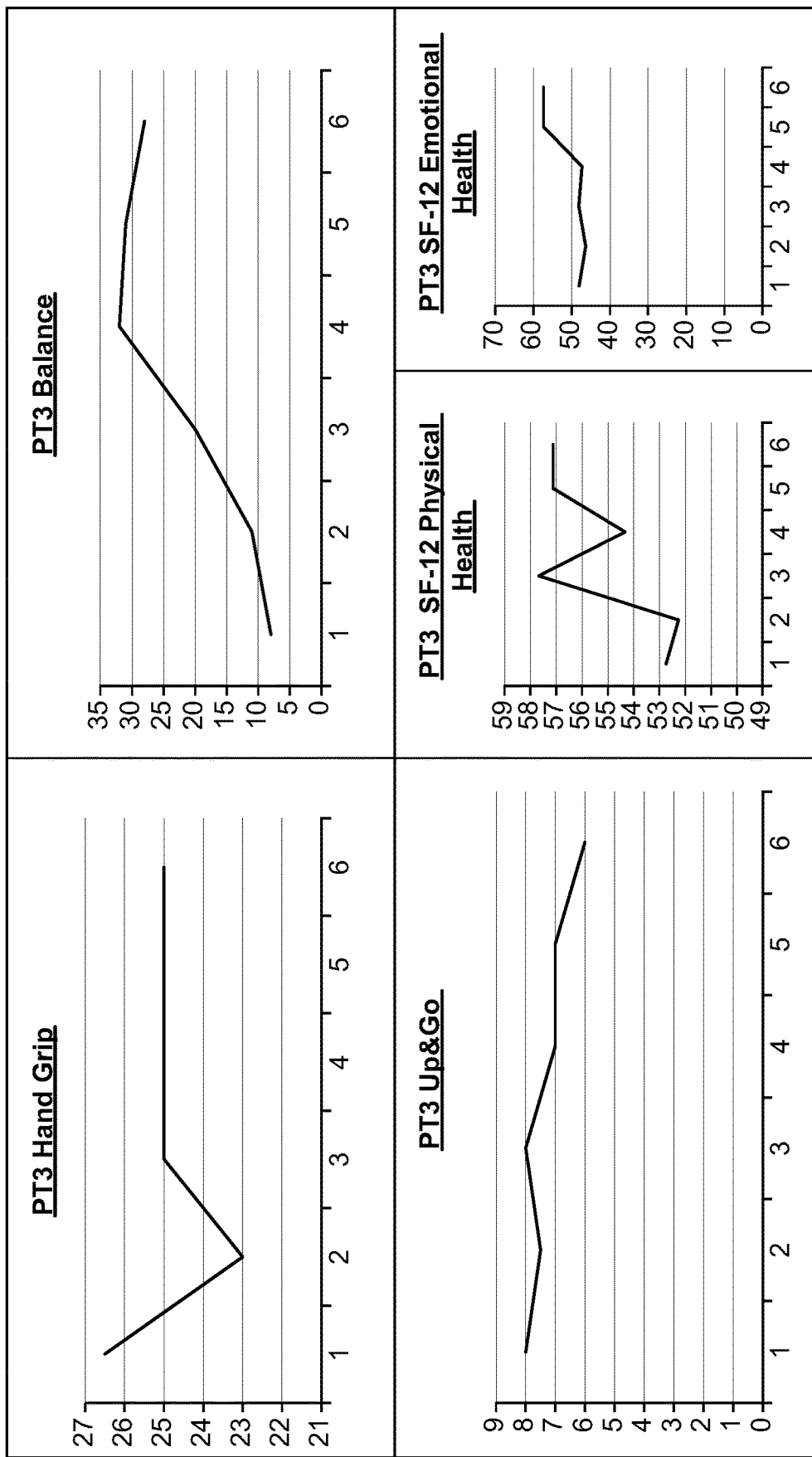
FIG. 3 is a series of graphs of physical, and mental macro data for a female collected over the course of six plasmapheresis treatments.
Figure 4:
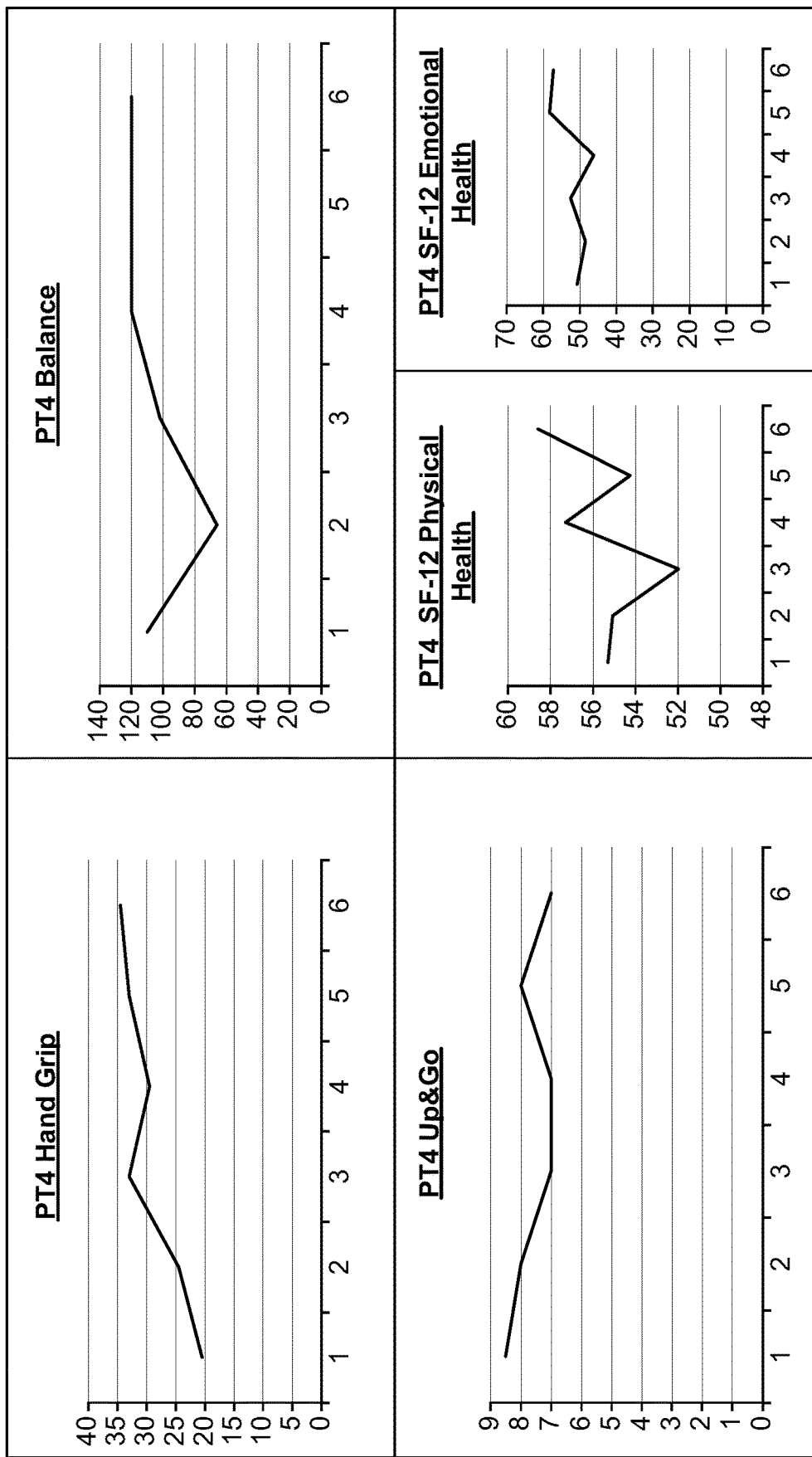
FIG. 4 is a series of graphs of physical, and mental macro data for a female collected over the course of six plasmapheresis treatments.

FIG. 3 shows multiple graphs of macro data for a third participant ("PT3") in the pilot study who is female and who received six treatments of plasmapheresis. PT3 had macro data collected before each one of her six plasmapheresis treatments. The exchange fluid of PT3 included 2 grams of IVIG for each plasmapheresis treatment that PT3 received. The graphs of FIG. 3 are titled to indicate which macro data they present. For each of the five graphs shown in FIG. 3, the x-axis has numbers 1 through 6 indicating a time before each of the six plasmapheresis treatments when data was collected. For the graph titled "PT3 Hand Grip", the y-axis shows the measurements of grip strength in units of Kg measured with a standard grip strength device. As can be seen, PT3's measured hand strength measurements decreased from an initially high measurement and then rose and appeared to plateau at a lower value than the initial strength measurement through the course of the six treatments. For the graph titled "PT3 Up&Go" the y-axis is the time in seconds that it took PT3 to stand from a seated position and walk a fixed distance that PT3 walked each of the six times that the measurement was taken (each participant tested also walked the same distance). As can be seen, PT3's time to walk the distance decreased between the first measurement and the last measurement indicating an improvement. For the graph titled "PT3 Balance" the y-axis is the time in seconds that PT3 was able to stand with one leg raised and where the maximum time measured was 120 seconds. As can be seen, PT3's ability to balance on one leg increased overall through the course of the six treatments. For the graph titled "PT3 SF-12 Physical Health" the y-axis represents an SF-12 survey score for subjective physical health. As can be seen, PT3 showed an overall improvement in scores over the course of the six treatments. For the graph titled "PT3 SF-12 Emotional Health" the y-axis represents an SF-12 survey score for subjective emotional health. As can be seen, PT3 showed an overall improvement in scores over the course of the six treatments. FIG. 4 shows multiple graphs of macro data for a fourth participant ("PT4") in the pilot study who is female and who received six treatments of plasmapheresis. PT4 had macro data collected before each one of her six plasmapheresis treatments. The graphs of FIG. 4 are titled to indicate which macro data they present. For each of the five graphs shown in FIG. 4, the x-axis has numbers 1 through 6 indicating a time before each of the six plasmapheresis treatments when data was collected. For the graph titled "PT4 Hand Grip", the y-axis shows the measurements of grip strength in units of Kg measured with a standard grip strength device. As can be seen, PT4's measured hand strength increased overall over the course of the six treatments. For the graph titled "PT4 Up&Go" the y-axis is the time in seconds that it took PT4 to stand from a seated position and walk a fixed distance that PT4 walked each of the six times that the measurement was taken (each participant tested also walked the same distance). As can be seen, PT4's time to walk the distance decreased between the first measurement and the last measurement indicating an improvement. For the graph titled "PT4 Balance" the y-axis is the time in seconds that PT4 was able to stand with one leg raised and where the maximum time measured was 120 seconds. As can be seen, PT4's ability to balance on one leg increased overall through the course of the six treatments. For the graph titled "PT4 SF-12 Physical Health" the y-axis represents an SF-12 survey score for subjective physical health. As can be seen, PT4 showed an overall improvement in scores over the course of the six treatments. For the graph titled "PT4 SF-12 Emotional Health" the y-axis represents an SF-12 survey score for subjective emotional health. As can be seen, PT4 showed an overall improvement in scores over the course of the six treatments.

Figure 5:
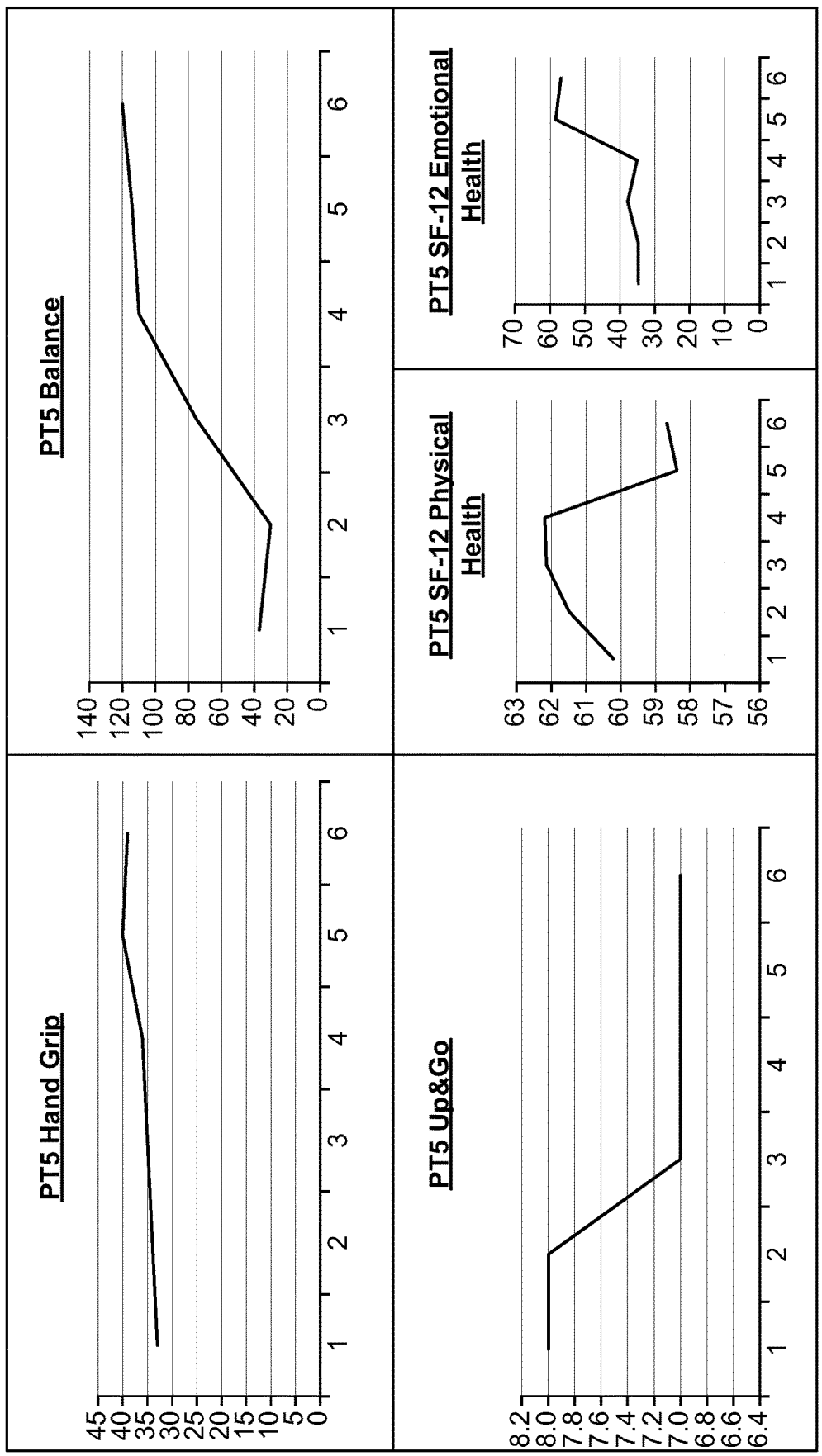
FIG. 5 is a series of graphs of physical, and mental macro data for a male collected over the course of six plasmapheresis treatments.

FIG. 5 shows multiple graphs of macro data for a fifth participant ("PT5") in the pilot study who is male and who received six treatments of plasmapheresis. PT5 had macro data collected before each one of his six plasmapheresis treatments. The graphs of FIG. 5 are titled to indicate which macro data they present. For each of the five graphs shown in FIG. 5, the x-axis has numbers 1 through 6 indicating a time before each of the six plasmapheresis treatments when data was collected. For the graph titled "PT5 Hand Grip", the y-axis shows the measurements of grip strength in units of Kg measured with a standard grip strength device. As can be seen, PT5's measured hand strength increased overall over the course of the six treatments. For the graph titled "PT5 Up&Go" the y-axis is the time in seconds that it took PT5 to stand from a seated position and walk a fixed distance that PT5 walked each of the six times that the measurement was taken (each participant tested also walked the same distance). As can be seen, PT's time to walk the distance decreased between the first measurement and the last measurement indicating an improvement. For the graph titled "PT5 Balance" the y-axis is the time in seconds that PT5 was able to stand with one leg raised and where the maximum time measured was 120 seconds. As can be seen, PT5's ability to balance on one leg increased overall through the course of the six treatments. For the graph titled "PT5 SF-12 Physical Health" the y-axis represents an SF-12 survey score for subjective physical health. As can be seen, PT5 showed an overall improvement in scores initially over the course of the six treatments that then decreased. For the graph titled "PT5 SF-12 Emotional Health" the y-axis represents an SF-12 survey score for subjective emotional health. As can be seen, PT5 showed an overall improvement in scores over the course of the six treatments.

Figure 6:
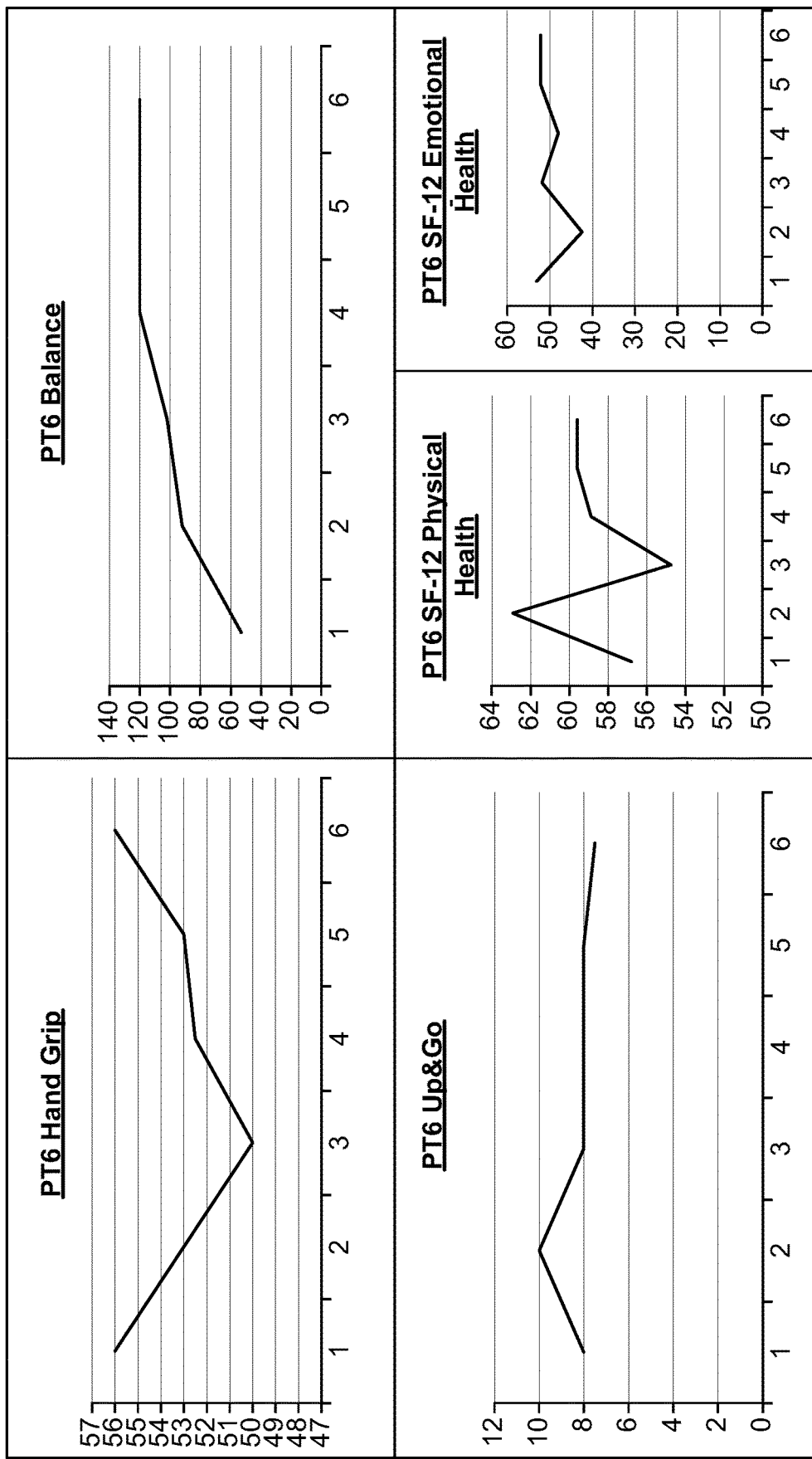
FIG. 6 is a series of graphs of physical, and mental macro data for a male collected over the course of six plasmapheresis treatments.

FIG. 6 shows multiple graphs of macro data for a fourth participant ("PT6") in the pilot study who is male and who received six treatments of plasmapheresis. PT6 had macro data collected before each one of his six plasmapheresis treatments. The exchange fluid of PT6 included 2 grams of IVIG for each plasmapheresis treatment that PT6 received. The graphs of FIG. 6 are titled to indicate which macro data they present. For each of the five graphs shown in FIG. 6, the x-axis has numbers 1 through 6 indicating a time before each of the six plasmapheresis treatments when data was collected. For the graph titled "PT6 Hand Grip", the y-axis shows the measurements of grip strength in units of Kg measured with a standard grip strength device. As can be seen, PT6's measured hand strength decreased initially and then increased so that overall over the course of the six treatments there was no measured overall change. For the graph titled "PT6 Up&Go" the y-axis is the time in seconds that it took PT6 to stand from a seated position and walk a fixed distance that PT6 walked each of the six times that the measurement was taken (each participant tested also walked the same distance). As can be seen, PT6's time to walk the distance decreased between the first measurement and the last measurement indicating an improvement. For the graph titled "PT6 Balance" the y-axis is the time in seconds that PT6 was able to stand with one leg raised and where the maximum time measured was 120 seconds. As can be seen, PT6's ability to balance on one leg increased overall through the course of the six treatments. For the graph titled "PT6 SF-12 Physical Health" the y-axis represents an SF-12 survey score for subjective physical health. As can be seen, PT6 showed an overall improvement in scores over the course of the six treatments. For the graph titled "PT6 SF-12 Emotional Health" the y-axis represents an SF-12 survey score for subjective emotional health. As can be seen, PT6 showed an overall slight decrease in scores over the course of the six treatments.

Figure 7:
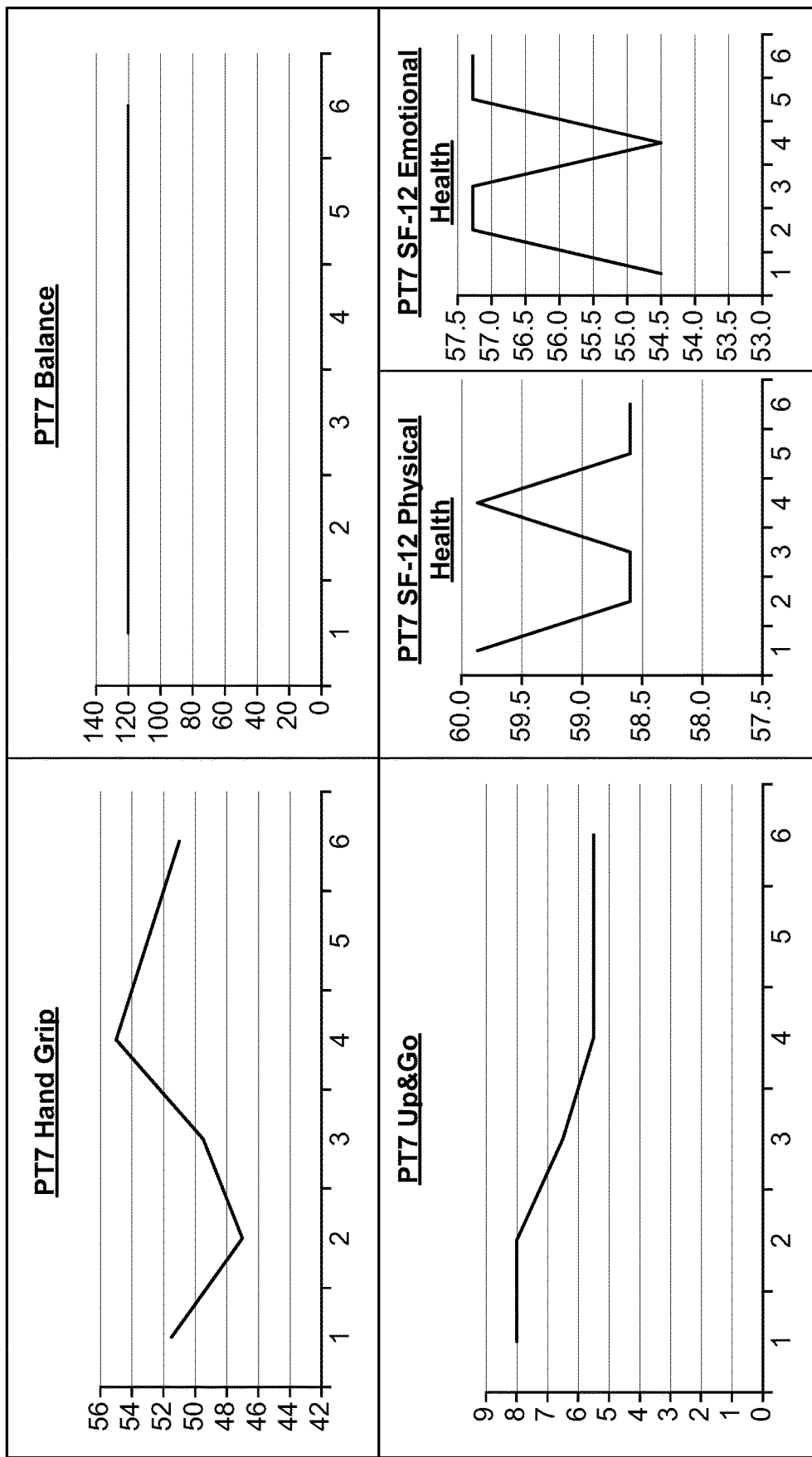
FIG. 7 is a series of graphs of physical, and mental macro data for a male collected over the course of six plasmapheresis treatments.

FIG. 7 shows multiple graphs of macro data for a fourth participant ("PT7") in the pilot study who is male and who received six treatments of plasmapheresis. PT7 had macro data collected before each one of his six plasmapheresis treatments. The graphs of FIG. 7 are titled to indicate which macro data they present. For each of the five graphs shown in FIG. 7, the x-axis has numbers 1 through 6 indicating a time before each of the six plasmapheresis treatments when data was collected. For the graph titled "PT7 Hand Grip", the y-axis shows the measurements of grip strength in units of Kg measured with a standard grip strength device. As can be seen, PT7's measured hand strength decreased initially and then increased so that overall over the course of the six treatments there a slight decrease in overall measured strength. For the graph titled "PT7 Up&Go" the y-axis is the time in seconds that it took PT7 to stand from a seated position and walk a fixed distance that PT7 walked each of the six times that the measurement was taken (each participant tested also walked the same distance). As can be seen, PT7's time to walk the distance decreased between the first measurement and the last measurement indicating an improvement. For the graph titled "PT7 Balance" the y-axis is the time in seconds that PT7 was able to stand with one leg raised and where the maximum time measured was 120 seconds. As can be seen, PT7 was able to stand the maximum measured time throughout the duration of the study. For the graph titled "PT7 SF-12 Physical Health" the y-axis represents an SF-12 survey score for subjective physical health. As can be seen, PT7 showed an overall improvement in scores initially over the course of the six treatments that then decreased. For the graph titled "PT7 SF-12 Emotional Health" the y-axis represents an SF-12 survey score for subjective emotional health. As can be seen, PT7 showed an overall slight decrease in scores over the course of the six treatments.

Figure 8:
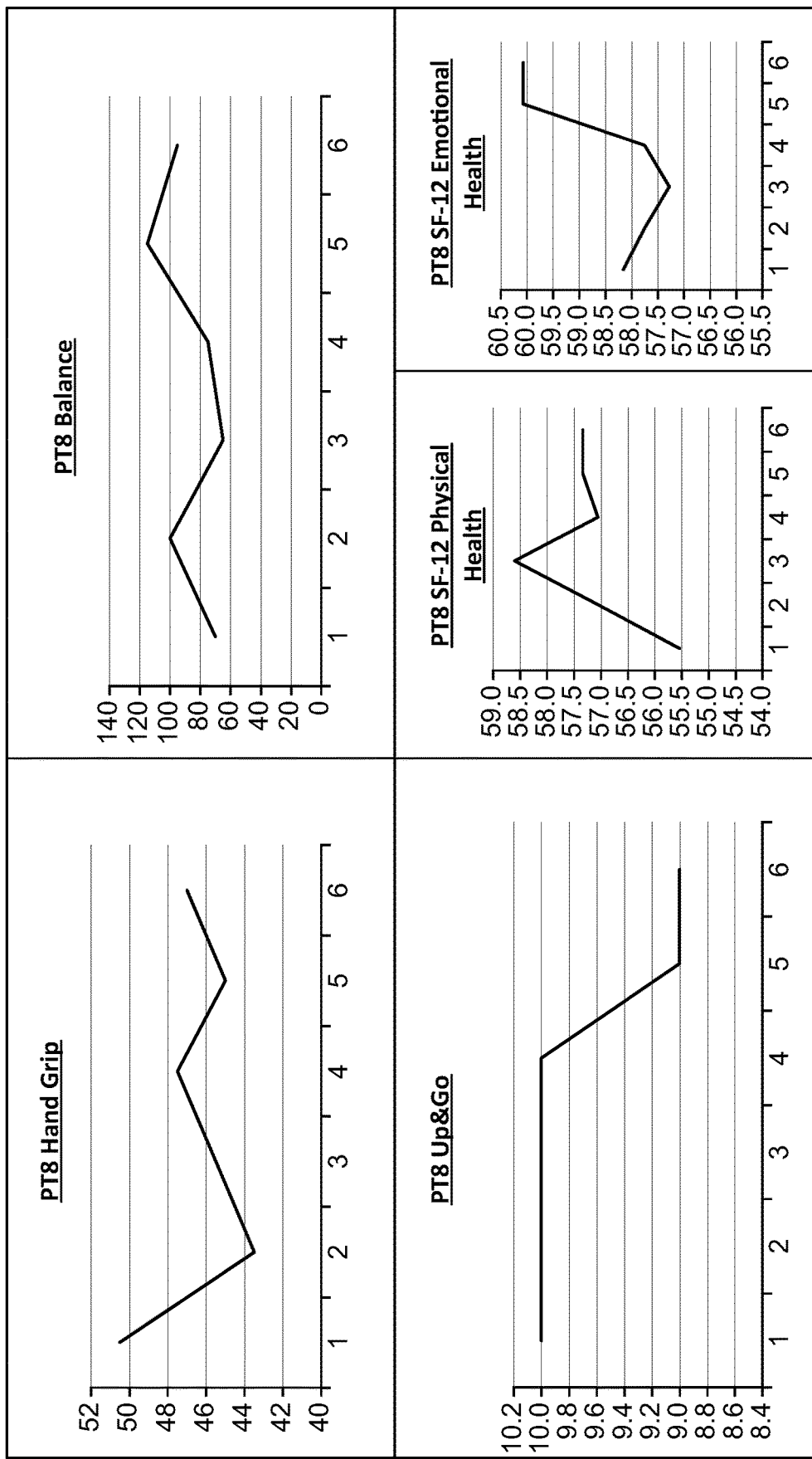
FIG. 8 is a series of graphs of physical, and mental macro data for a male collected over the course of six plasmapheresis treatments.

FIG. 8 shows multiple graphs of macro data for an eight participant ("PT8") in the pilot study who is male and who received six treatments of plasmapheresis. PT8 had macro data collected before each one of his six plasmapheresis treatments. The exchange fluid of PT8 included 2 grams of IVIG for each plasmapheresis treatment that PT8 received. The graphs of FIG. 8 are titled to indicate which macro data they present. For each of the five graphs shown in FIG. 8, the x-axis has numbers 1 through 6 indicating a time before each of the six plasmapheresis treatments when data was collected. For the graph titled "PT8 Hand Grip", the y-axis shows the measurements of grip strength in units of Kg measured with a standard grip strength device. As can be seen, PT8's measured hand strength decreased initially and then increased slightly but overall decreased over the course of the six treatments. For the graph titled "PT8 Up&Go" the y-axis is the time in seconds that it took PT8 to stand from a seated position and walk a fixed distance that PT8 walked each of the six times that the measurement was taken (each participant tested also walked the same distance). As can be seen, PT8's time to walk the distance decreased between the first measurement and the last measurement indicating an improvement. For the graph titled "PT8 Balance" the y-axis is the time in seconds that PT8 was able to stand with one leg raised and where the maximum time measured was 120 seconds. As can be seen, PT8's ability to balance on one leg increased overall through the course of the six treatments. For the graph titled "PT8 SF-12 Physical Health" the y-axis represents an SF-12 survey score for subjective physical health. As can be seen, PT8 showed an overall improvement in scores over the course of the six treatments. For the graph titled "PT8 SF-12 Emotional Health" the y-axis represents an SF-12 survey score for subjective emotional health. As can be seen, PT8 showed an overall improvement in scores over the course of the six treatments.

Figure 9:
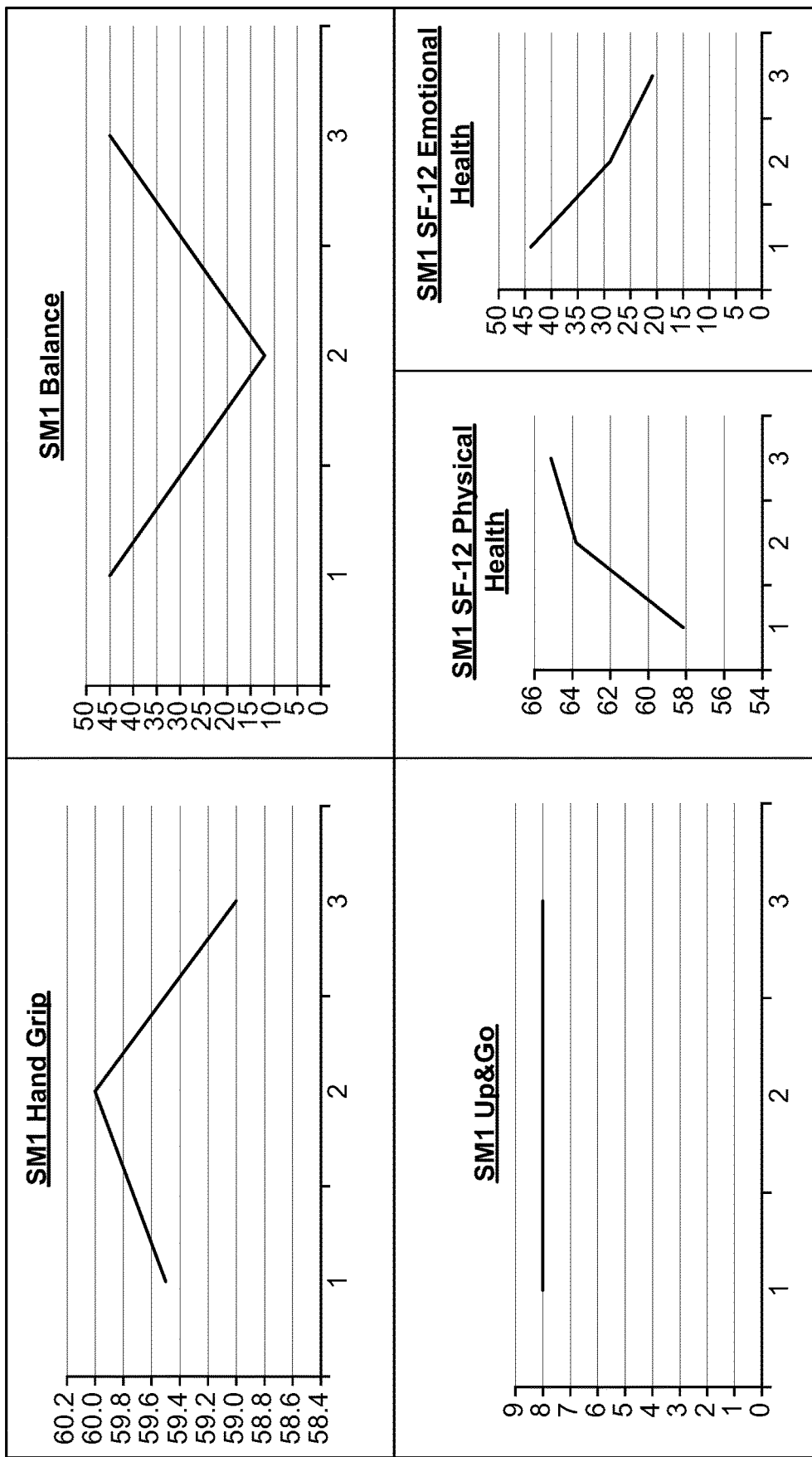
FIG. 9 is a series of graphs of physical, and mental macro data for a male collected over the course of three sham plasmapheresis treatments.

FIG. 9 shows multiple graphs of macro data for a first sham participant ("SM1") in the pilot study who is male and who received three sham plasmapheresis treatments (i.e. no plasmapheresis treatments were delivered but participant was given illusion that plasmapheresis was administered). SM1 was the first of three participants who provided control data that is presented here. SM1 had macro data collected before each one of his three sham plasmapheresis treatments. The graphs of FIG. 9 are titled to indicate which macro data they present. For each of the five graphs shown in FIG. 9, the x-axis has numbers 1 through 3 indicating a time before each of the three sham plasmapheresis treatments when data was collected. For the graph titled "SM1 Hand Grip", the y-axis shows the measurements of grip strength in units of Kg measured with a standard grip strength device. As can be seen, SM1's measured hand strength decreased overall over the course of the three sham treatments. For the graph titled "SM1 Up&Go" the y-axis is the time in seconds that it took SM1 to stand from a seated position and walk a fixed distance that SM1 walked each of the three times that the measurement was taken (each participant tested, including the plasmapheresis treated participants, also walked the same distance). As can be seen, SM1's time to walk the distance remained unchanged over the period of receiving sham plasmapheresis treatments. For the graph titled "SM1 Balance" the y-axis is the time in seconds that SM1 was able to stand with one leg raised and where the maximum time measured was 120 seconds. As can be seen, SM1's ability to balance on one leg initially decreased and then increased to end overall unchanged through the course of the three sham plasmapheresis treatments. For the graph titled "SM1 SF-12 Physical Health" the y-axis represents an SF-12 survey score for subjective physical health. As can be seen, SM1 showed an overall improvement in scores over the course of the three sham plasmapheresis treatments. For the graph titled "SM1 SF-12 Emotional Health" the y-axis represents an SF-12 survey score for subjective emotional health. As can be seen, SM1 showed an overall decrease in scores over the course of the three sham plasmapheresis treatments.

Figure 10:
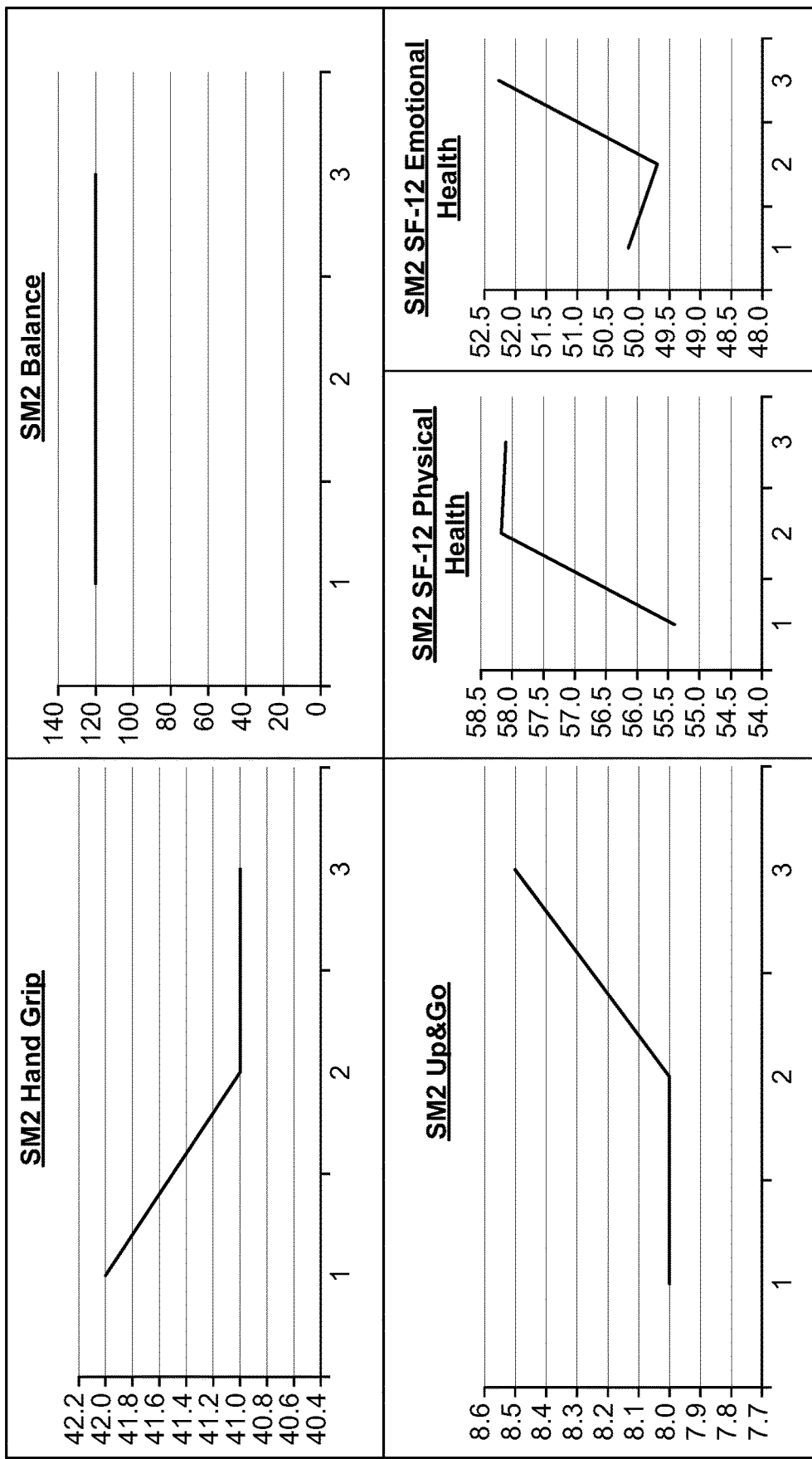
FIG. 10 is a series of graphs of physical, and mental macro data for a male collected over the course of three sham plasmapheresis treatments.

FIG. 10 shows multiple graphs of macro data for a first sham participant ("SM2") in the pilot study who is male and who received three sham plasmapheresis treatments (i.e. no plasmapheresis treatments were delivered but participant was given illusion that plasmapheresis was administered). SM2 was the second of three participants who provided control data that is presented here. SM2 had macro data collected before each one of his three sham plasmapheresis treatments. The graphs of FIG. 10 are titled to indicate which macro data they present. For each of the five graphs shown in FIG. 10, the x-axis has numbers 1 through 3 indicating a time before each of the three sham plasmapheresis treatments when data was collected. For the graph titled "SM2 Hand Grip", the y-axis shows the measurements of grip strength in units of Kg measured with a standard grip strength device. As can be seen, SM2's measured hand strength decreased overall over the course of the three sham treatments. For the graph titled "SM2 Up&Go" the y-axis is the time in seconds that it took SM2 to stand from a seated position and walk a fixed distance that SM2 walked each of the three times that the measurement was taken (each participant tested, including the plasmapheresis treated participants, also walked the same distance). As can be seen, SM2's time to walk the distance increased over the course of the sham plasmapheresis treatments which indicates a worsening overall. For the graph titled "SM2 Balance" the y-axis is the time in seconds that SM2 was able to stand with one leg raised and where the maximum time measured was 120 seconds. As can be seen, SM2 was able to stand the maximum measured time throughout course of receiving sham plasmapheresis treatments. For the graph titled "SM2 SF-12 Physical Health" the y-axis represents an SF-12 survey score for subjective physical health. As can be seen, SM2 showed an overall improvement in scores over the course of the three sham plasmapheresis treatments. For the graph titled "SM1 SF-12 Emotional Health" the y-axis represents an SF-12 survey score for subjective emotional health. As can be seen, SM2 showed an overall increase in scores over the course of the three sham plasmapheresis treatments.

Figure 11:
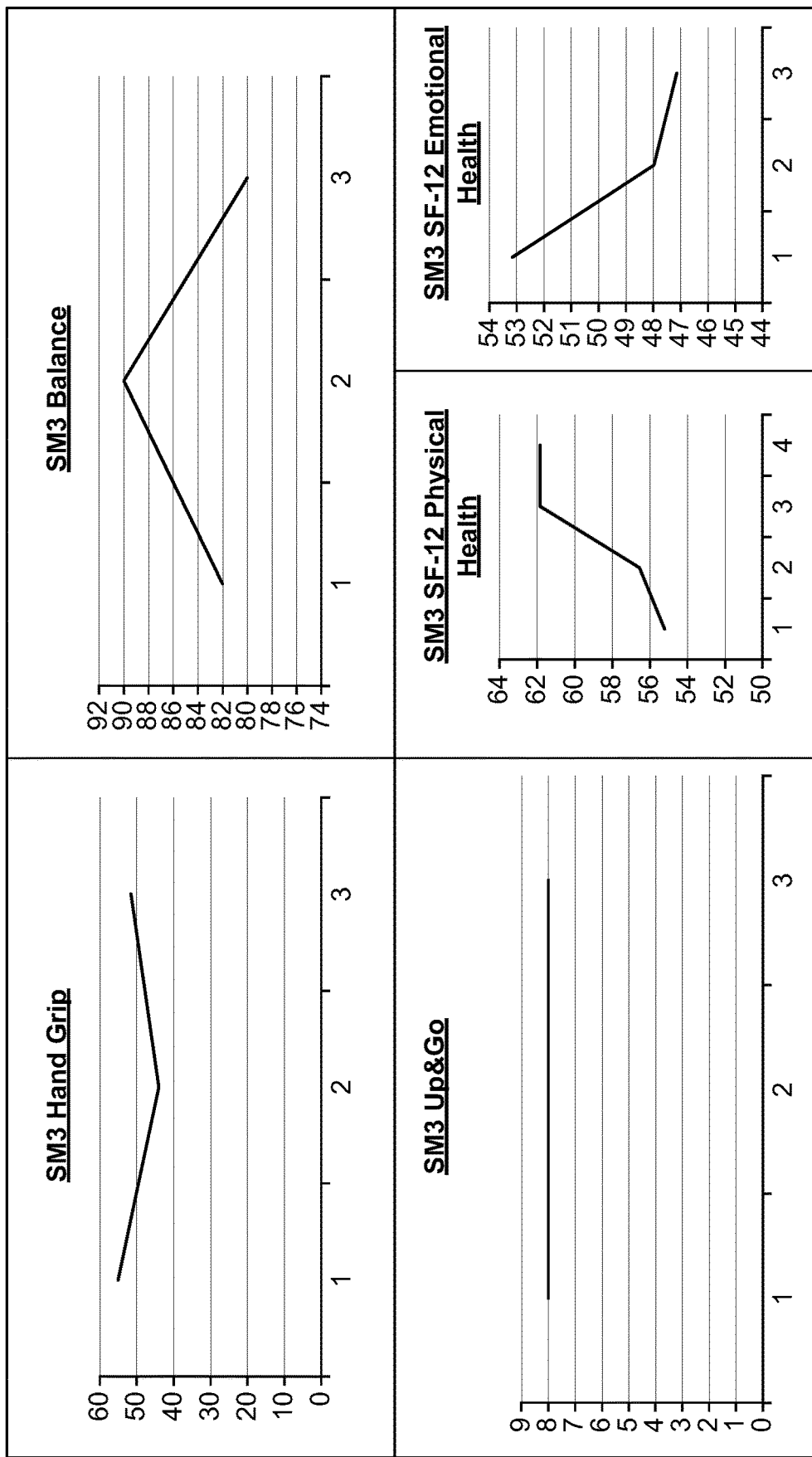
FIG. 11 is a series of graphs of physical, and mental macro data for a male collected over the course of three sham plasmapheresis treatments.

FIG. 11 shows multiple graphs of macro data for a first sham participant ("SM3") in the pilot study who is male and who received three sham plasmapheresis treatments (i.e. no plasmapheresis treatments were delivered but participant was given illusion that plasmapheresis was administered). SM3 was the third of three participants who provided control data that is presented here. SM3 had macro data collected before each one of his three sham plasmapheresis treatments. The graphs of FIG. 11 are titled to indicate which macro data they present. For each of the five graphs shown in FIG. 11, the x-axis has numbers 1 through 3 indicating a time before each of the three sham plasmapheresis treatments when data was collected. For the graph titled "SM3 Hand Grip", the y-axis shows the measurements of grip strength in units of Kg measured with a standard grip strength device. As can be seen, SM3's measured hand strength decreased overall over the course of the three sham treatments. For the graph titled "SM3 Up&Go" the y-axis is the time in seconds that it took SM3 to stand from a seated position and walk a fixed distance that SM3 walked each of the three times that the measurement was taken (each participant tested, including the plasmapheresis treated participants, also walked the same distance). As can be seen, SM3's time to walk the distance was unchanged over the course of the sham plasmapheresis treatments. For the graph titled "SM3 Balance" the y-axis is the time in seconds that SM3 was able to stand with one leg raised and where the maximum time measured was 120 seconds. As can be seen, SM3 had an overall decrease in time he was able to balance on one leg over the course of the three sham plasmapheresis treatments. For the graph titled "SM3 SF-12 Physical Health" the y-axis represents an SF-12 survey score for subjective physical health. As can be seen, SM3 showed an overall improvement in scores over the course of the three sham plasmapheresis treatments. For the graph titled "SM3 SF-12 Emotional Health" the y-axis represents an SF-12 survey score for subjective emotional health. As can be seen, SM3 showed an overall decrease in scores over the course of the three sham plasmapheresis treatments.

In terms of timing of treatments, each of PT1, PT2, PT3, PT4, PT5, PT6, PT7, and PT8 received two treatments a month for three total months, and each of the two monthly treatments for all eight participants were always within at most one week of each other (i.e. at most one week between treatment #1 and #2, treatment #3 and #4, and treatment #5 and #6). In addition, for PT3, there were 48 hours between treatment #3 and treatment #4. For PT4, there were 48 hours between treatment #3 and treatment #4. For PT5, there were 48 hours between treatment #1 and treatment #2, there were 48 hours between treatment #3 and treatment #4, and there were 48 hours between treatment #5 and treatment #6. For PT6, there were 72 hours between treatment #3 and treatment #4, and there were 48 hours between treatment #5 and treatment #6. For PT7, there were 72 hours between treatment #1 and treatment #2, there were 48 hours between treatment #3 and treatment #4, and there were 48 hours between treatment #5 and treatment #6. For PT5, there were 48 hours between treatment #1 and treatment #2, there were 48 hours between treatment #3 and treatment #4, and there were 48 hours between treatment #5 and treatment #6. As such, over half of the paired monthly treatments delivered for PT1, PT2, PT3, PT4, PT5, PT6, PT7, and PT8 were within 72 hours of one another.

TABLE III

| ID | Hand Grip | UP & Go | Balance | S-12/P | SF-12/E |
|---|---|---|---|---|---|
| PT1 | 6.5 | −0.5 | 0(120) | 15.68 | 21.75 |
| PT2 | 2.5 | −1.6 | 0(120) | 5.91 | 0.98 |
| PT3 | −1.5 | −2 | 20 | 4.38 | 9.33 |
| PT4 | 14 | −1.5 | 10(110) | 3.3 | 6.52 |
| PT5 | 6 | −1 | 83 | −1.54 | 22.17 |
| PT6 | 0 | −0.5 | 67 | 2.8 | −0.93 |
| PT7 | −0.5 | −2.5 | 0(120) | −1.27 | 2.78 |
| PT8 | −3.5 | −1 | 25 | 1.8 | 1.91 |
| SM1 | −0.5 | 0 | 0(45) | 6.98 | −23.14 |
| SM2 | −1 | 0.5 | 0(120) | 2.7 | 2.1 |
| SM3 | −3.5 | 0 | −2 | 6.61 | −6.01 |

TABLE III above shows aggregate macro data for all 11 participants for which macro data is shown and described herein in FIGS. 1-11 and their respective accompanying descriptions. More specifically, the numerical data in TABLE III is the difference (or delta) between the first data point and the last data point for each macro data parameter measured for all 11 participants. That is, for the eight participants that received six plasmapheresis treatments each number in TABLE III is the last measured data value (i.e. preceding the sixth plasmapheresis treatment) minus the first measured data value (i.e. preceding the first plasmapheresis treatment). Similarly, for each of the three ham controls each number is the last measured data value (i.e. preceding the third sham plasmapheresis treatment) minus the first measured data value (i.e. preceding the first sham plasmapheresis treatment). In addition, where there are numbers in parentheses, these numbers are the first measured value. As can be seen for the participants, PT1, PT2, PT3, PT4, PT5, PT6, PT7, and PT8, there was across the board overall improvement in the multiple different metrics and especially with respect to the Up&Go metric where every treated patient showed improvement (for the Up&Go a decrease in value is an improvement). Compared to the three sham controls, SM1, SM2, and SM3, none of whom showed improvement in strength, walking, or balance, and far less overall improvement in subjective measures, there was strong indication that plasmapheresis had positive affect on strength, walking, balance, and mental wellbeing metrics as compared to controls.

Micro Data

For the micro data, each study participant had three blood samples taken in the course of the plasmapheresis study, one before a first plasmapheresis treatment, one in the middle of the plasmapheresis treatment cycle (i.e. before the fourth plasmapheresis treatment), and one before receiving the last plasmapheresis treatment. Blood samples had flow cytometry (including use of fluorescent coupled antibodies) performed on them to assess and quantify cell distribution as well as cell surface protein quantification (i.e. cell count of cells having cell surface protein phenotype). Flow cytometry and analysis of blood samples of participants from the pilot study was performed at the Buck Institute for Aging in Novato, California. For each sample, amounts of expression of the following cell surface markers (i.e. cell surface proteins) was measured: CD16, CD25, CD27, CD38, CD57, CD80, HLADR, IgM, KIR, KLRG1, NK1, NKg2a, and TIGIT. In addition, SA-β-gal, an indicator of cellular senescence was quantified as well.

Figure 12:
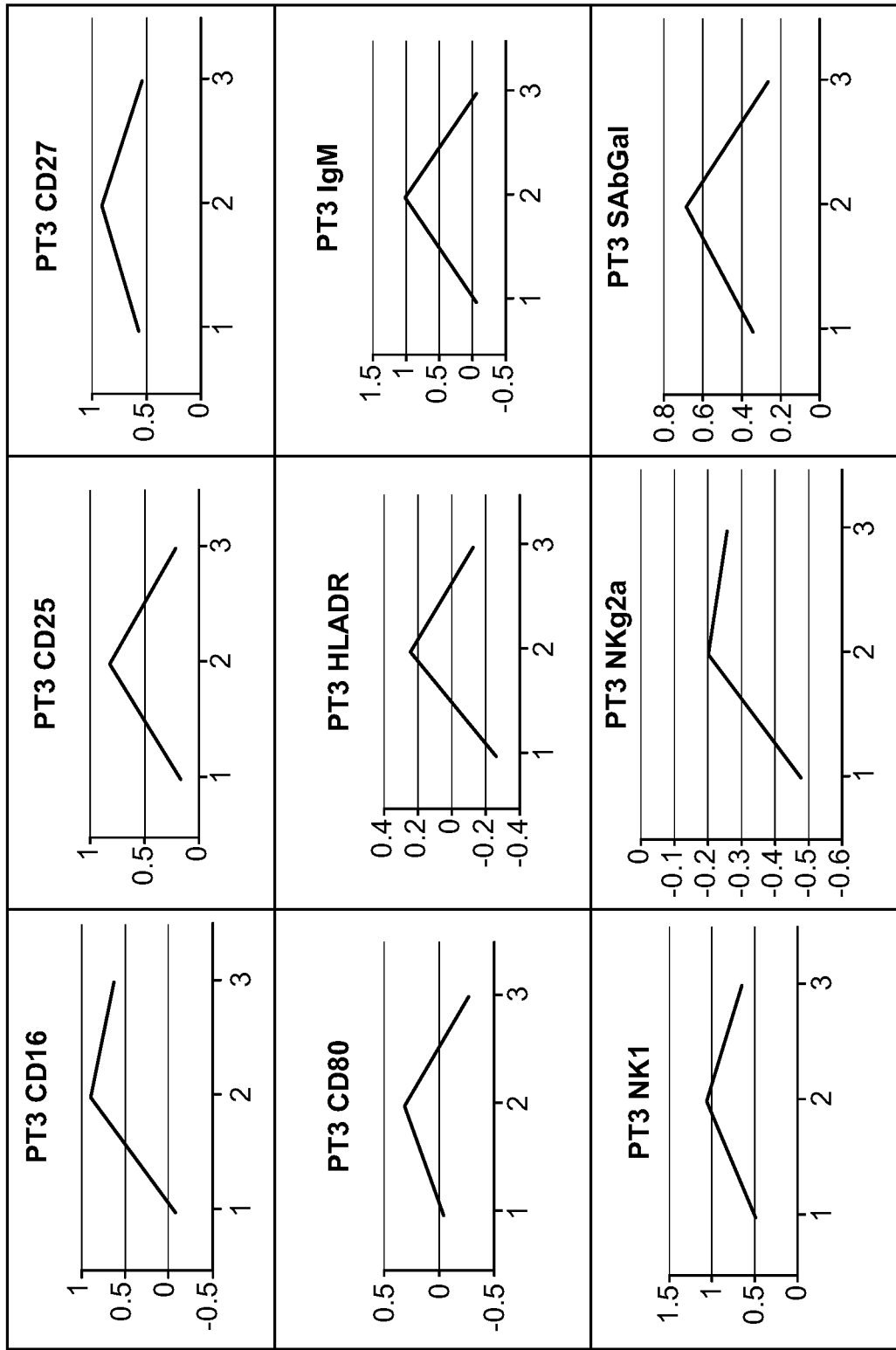
FIG. 12 is a series of graphs of biological aging marker levels measured in the blood of a female subjected to a regimen of six plasmapheresis treatments.
Figure 12:
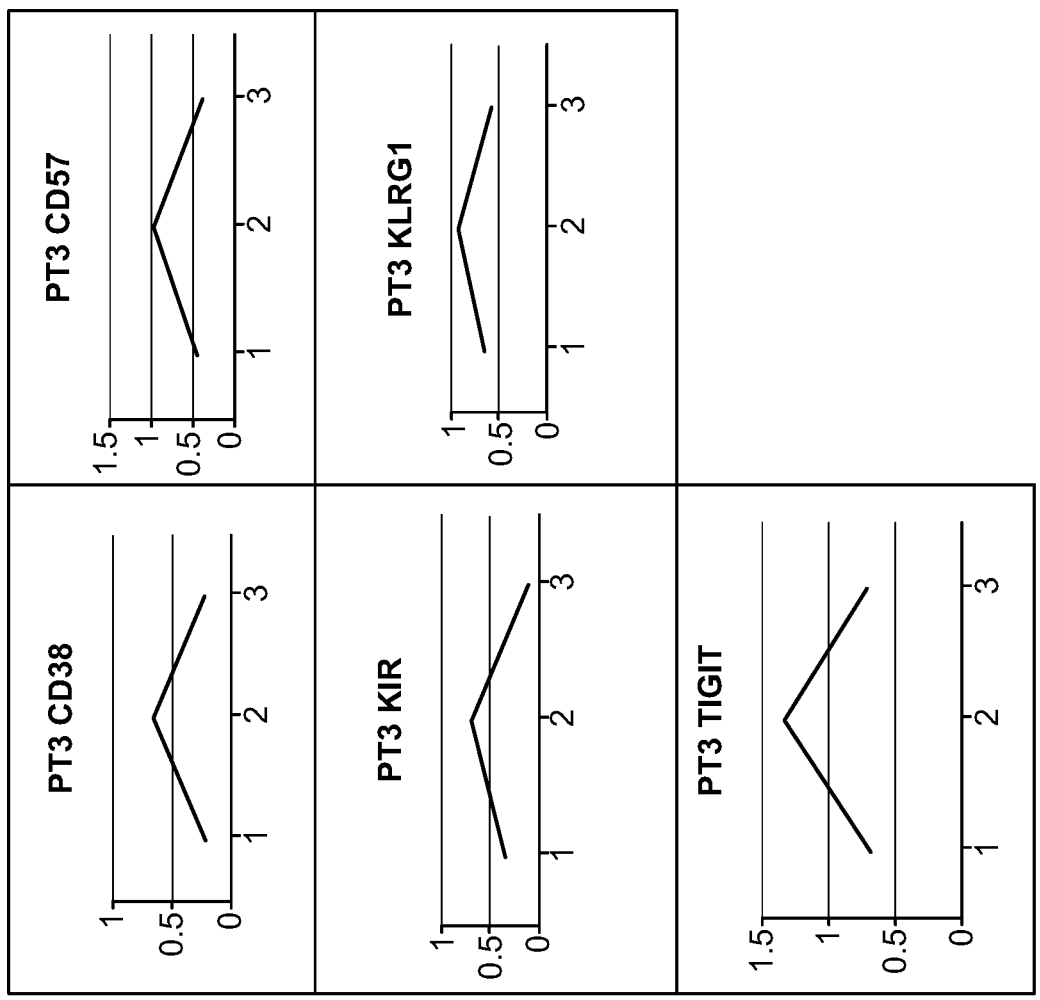

FIG. 12 shows graphs of normalized flow cytometry micro data assaying for degree of expression of the cell surface markers CD16, CD25, CD27, CD38, CD57, CD80, HLADR, IgM, KIR, KLRG1, NK1, NKg2a, and TIGIT in cells from blood samples taken from participants in the pilot study. An assay was performed on expression of SA-β-gal as well in cells from blood samples taken from participants in the pilot study. The graphs in FIG. 12 show micro data for blood samples taken from PT3. Three blood samples were taken from PT3, one before the first plasmapheresis treatment, one before the fourth plasmapheresis treatment, and one before the sixth and last plasmapheresis treatment, and these are the x-values 1, 2, and 3 of each graph.

Figure 13:
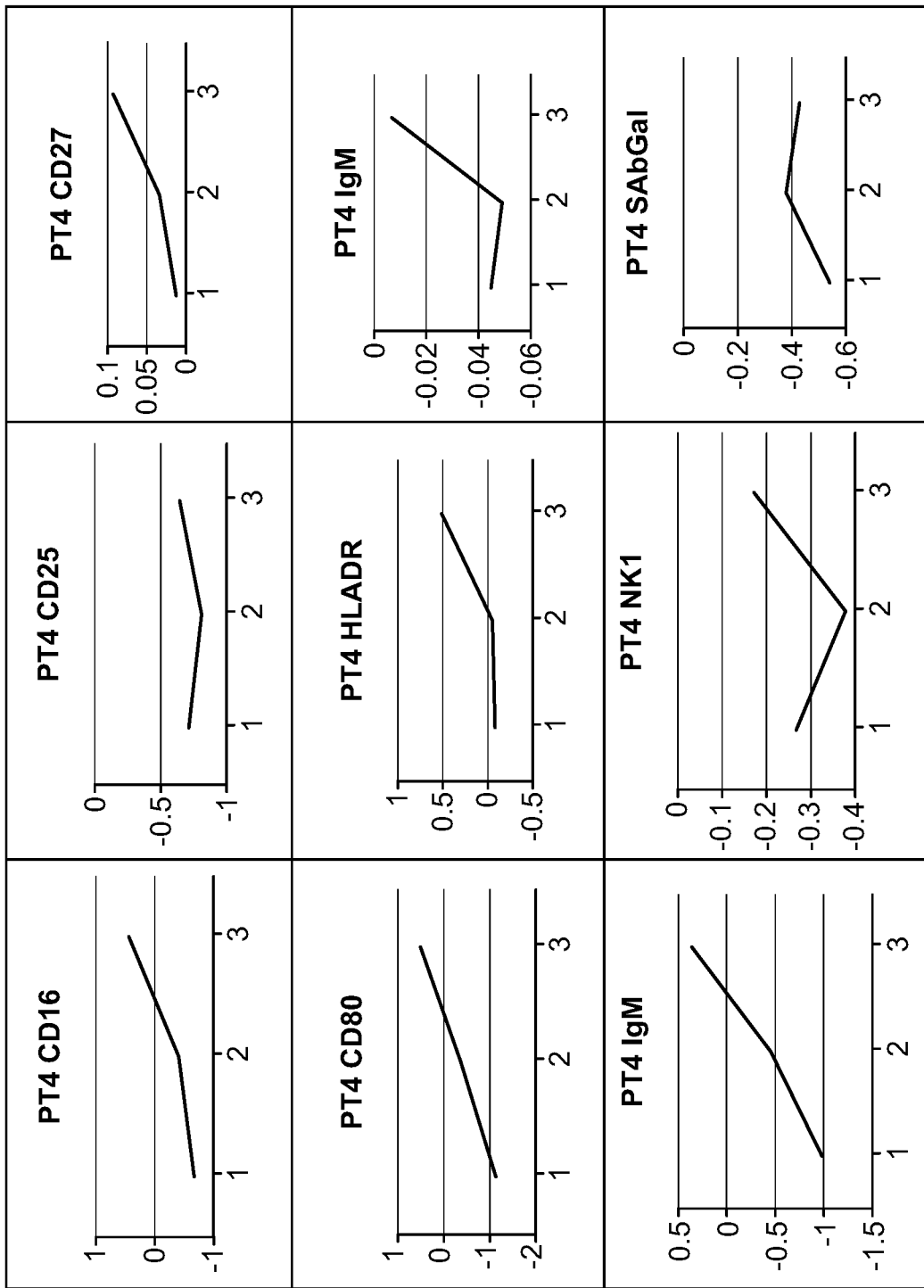
FIG. 13 is a series of graphs of biological aging marker levels measured in the blood of a female subjected to a regimen of six plasmapheresis treatments.
Figure 13:
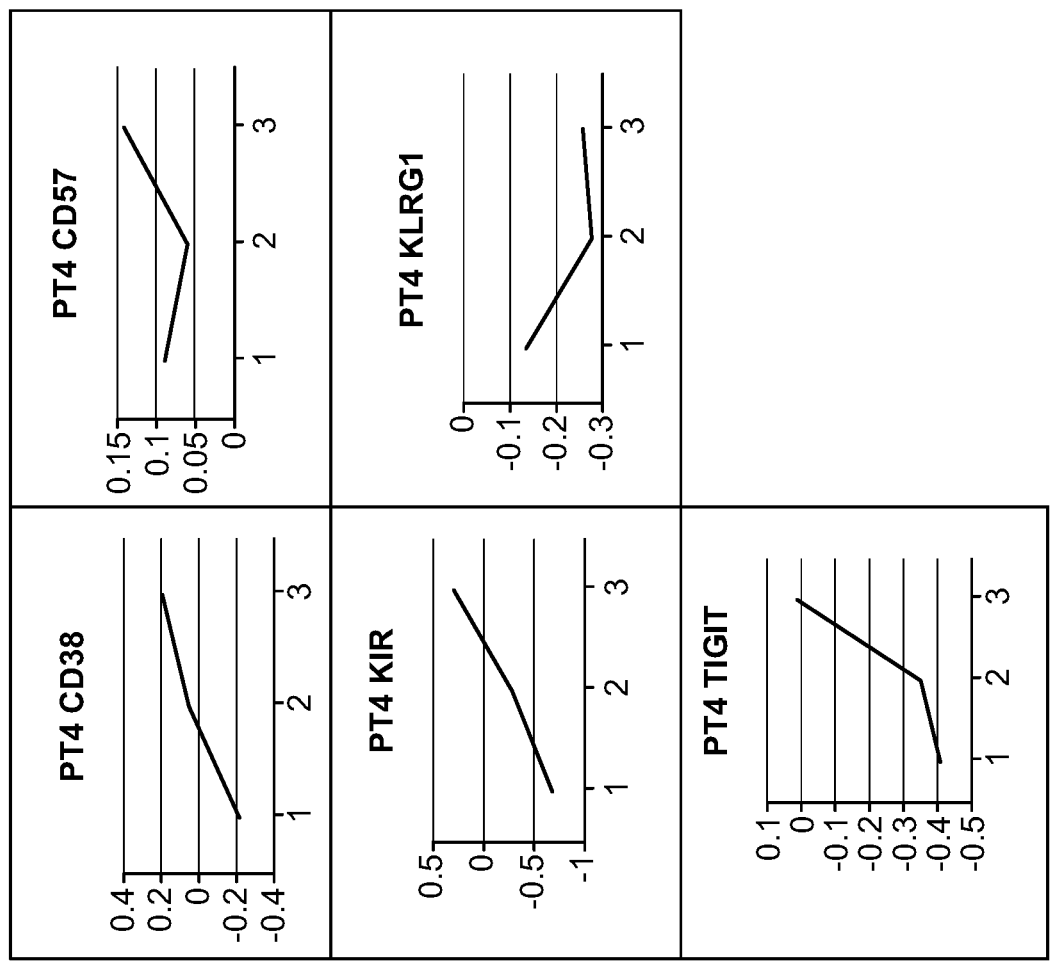

FIG. 13 shows graphs of normalized flow cytometry micro data assaying for degree of expression of the cell surface markers CD16, CD25, CD27, CD38, CD57, CD80, HLADR, IgM, KIR, KLRG1, NK1, NKg2a, and TIGIT in cells from blood samples taken from participants in the pilot study. An assay was performed on expression of SA-β-gal as well in cells from blood samples taken from participants in the pilot study. The graphs in FIG. 13 show micro data for blood samples taken from PT4. Three blood samples were taken from PT4, one before the first plasmapheresis treatment, one before the fourth plasmapheresis treatment, and one before the sixth and last plasmapheresis treatment, and these are the x-values 1, 2, and 3 of each graph.

Figure 14:
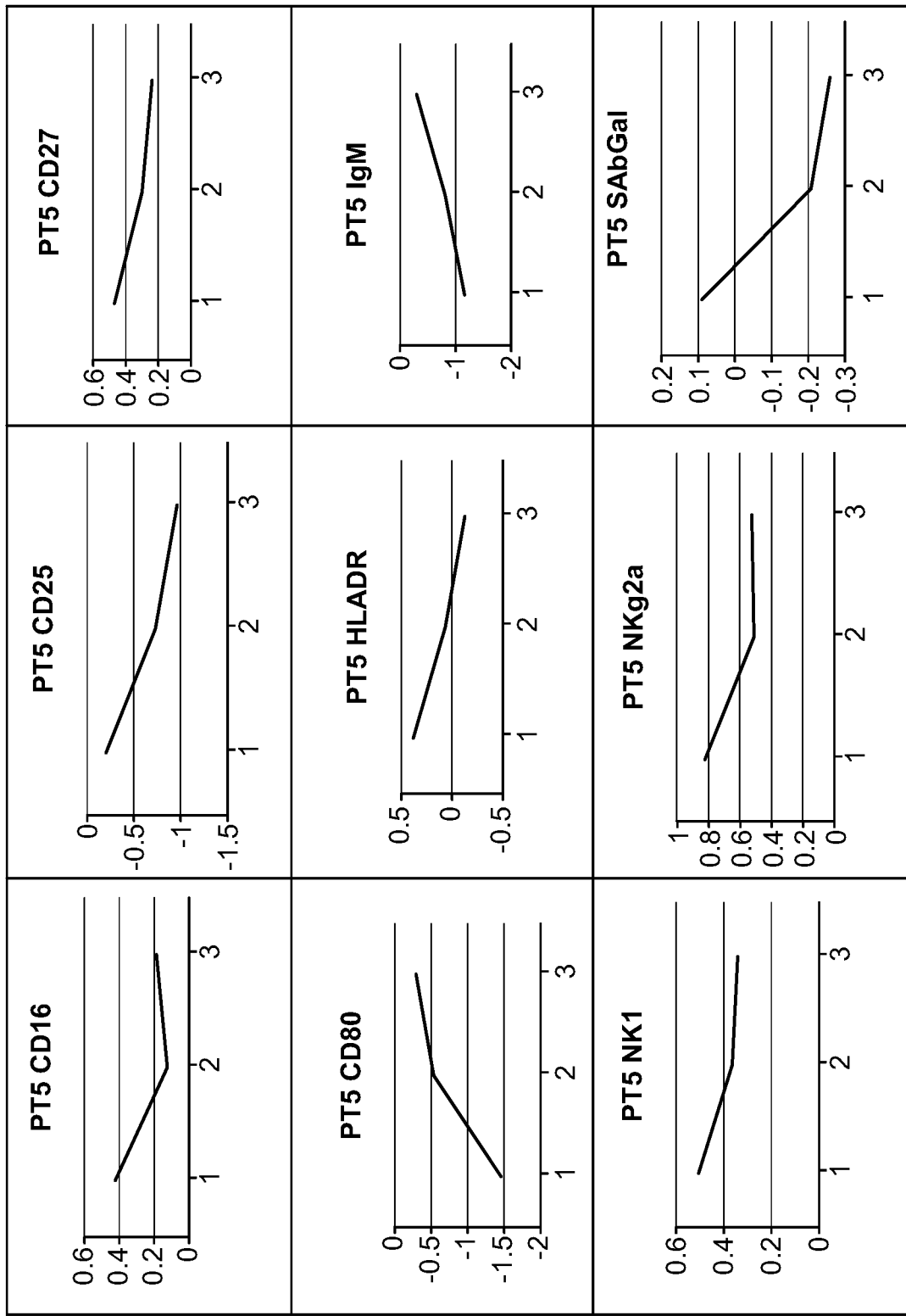
FIG. 14 is a series of graphs of biological aging marker levels measured in the blood of a male subjected to a regimen of six plasmapheresis treatments.
Figure 14:
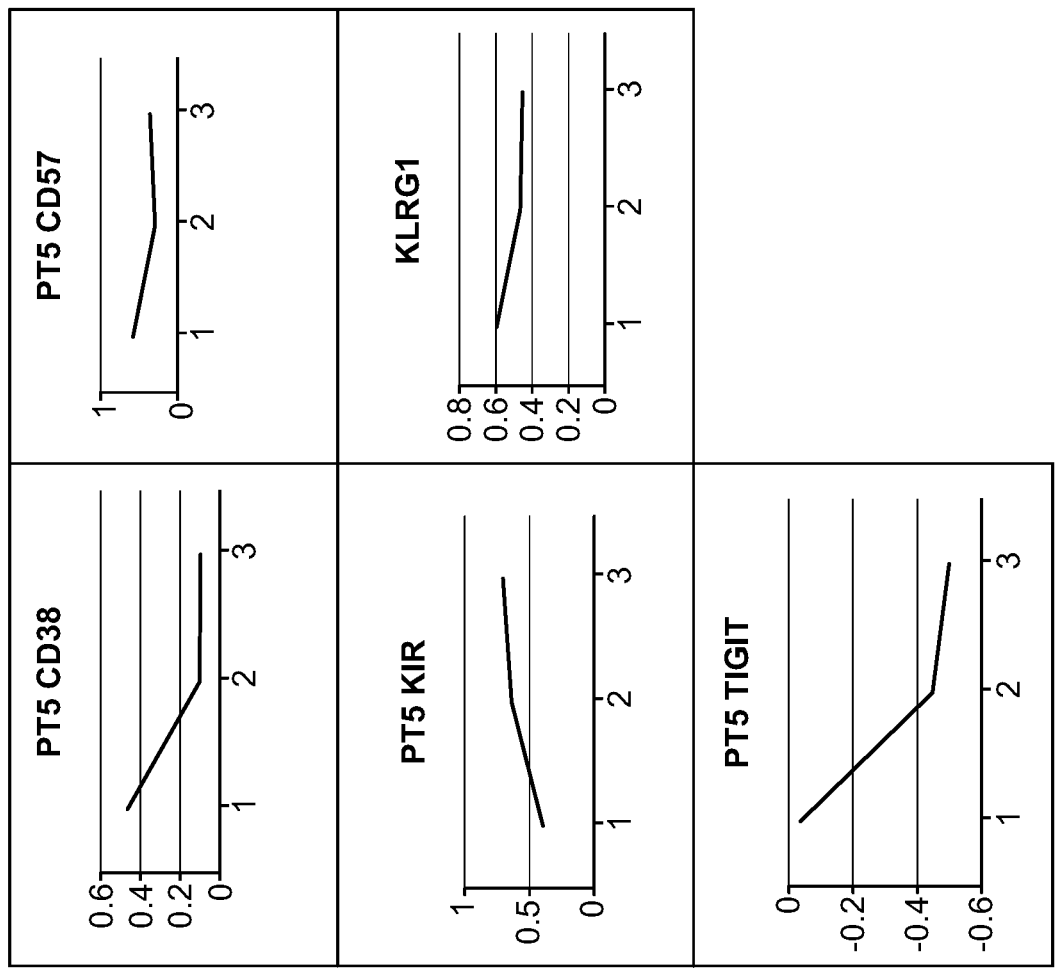

FIG. 14 shows graphs of normalized flow cytometry micro data assaying for degree of expression of the cell surface markers CD16, CD25, CD27, CD38, CD57, CD80, HLADR, IgM, KIR, KLRG1, NK1, NKg2a, and TIGIT in cells from blood samples taken from participants in the pilot study. An assay was performed on expression of SA-β-gal as well in cells from blood samples taken from participants in the pilot study. The graphs in FIG. 14 show micro data for blood samples taken from PT5. Three blood samples were taken from PT5, one before the first plasmapheresis treatment, one before the fourth plasmapheresis treatment, and one before the sixth and last plasmapheresis treatment, and these are the x-values 1, 2, and 3 of each graph.

Figure 15:
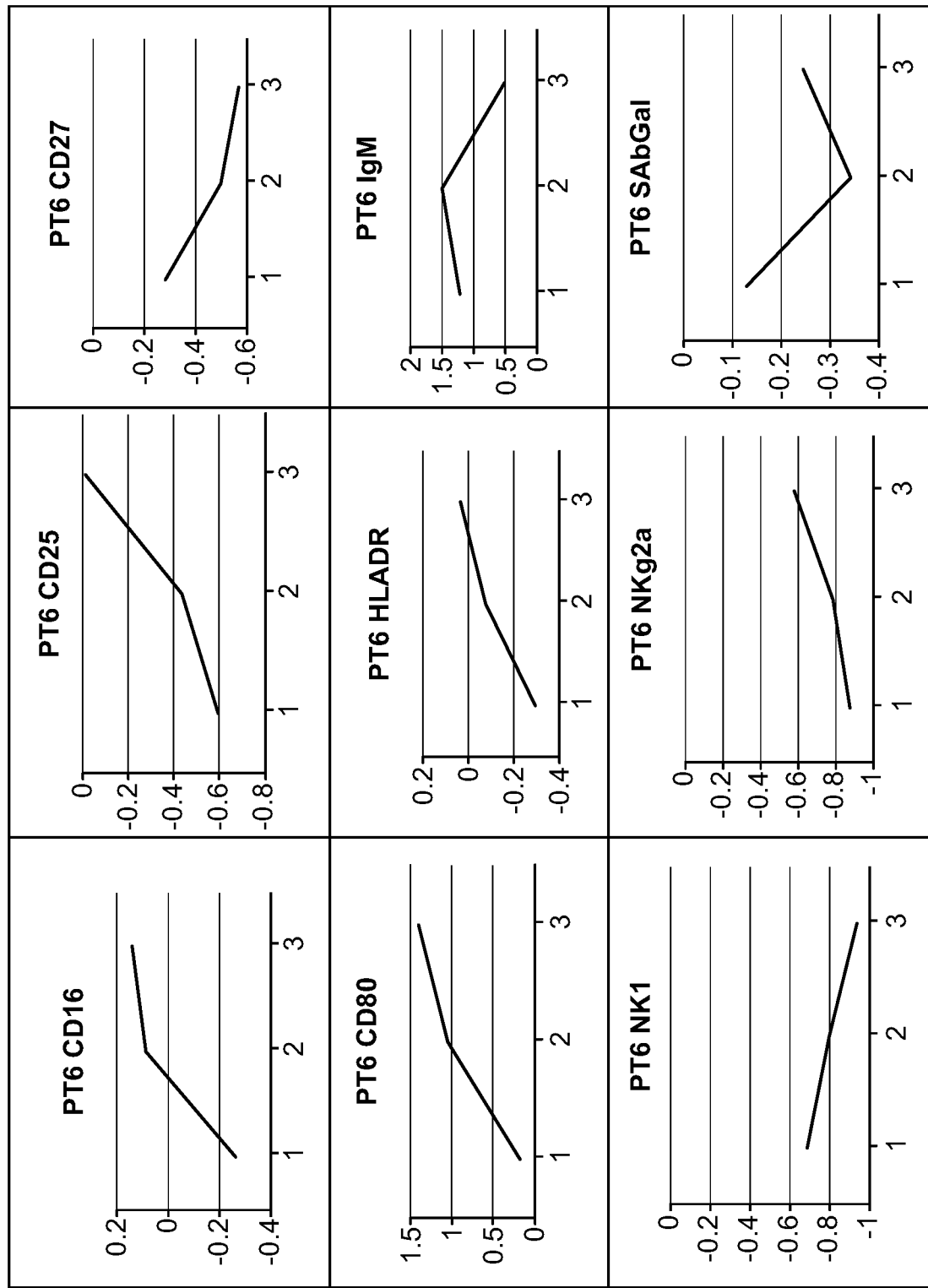
FIG. 15 is a series of graphs of biological aging marker levels measured in the blood of a male subjected to a regimen of six plasmapheresis treatments.
Figure 15:
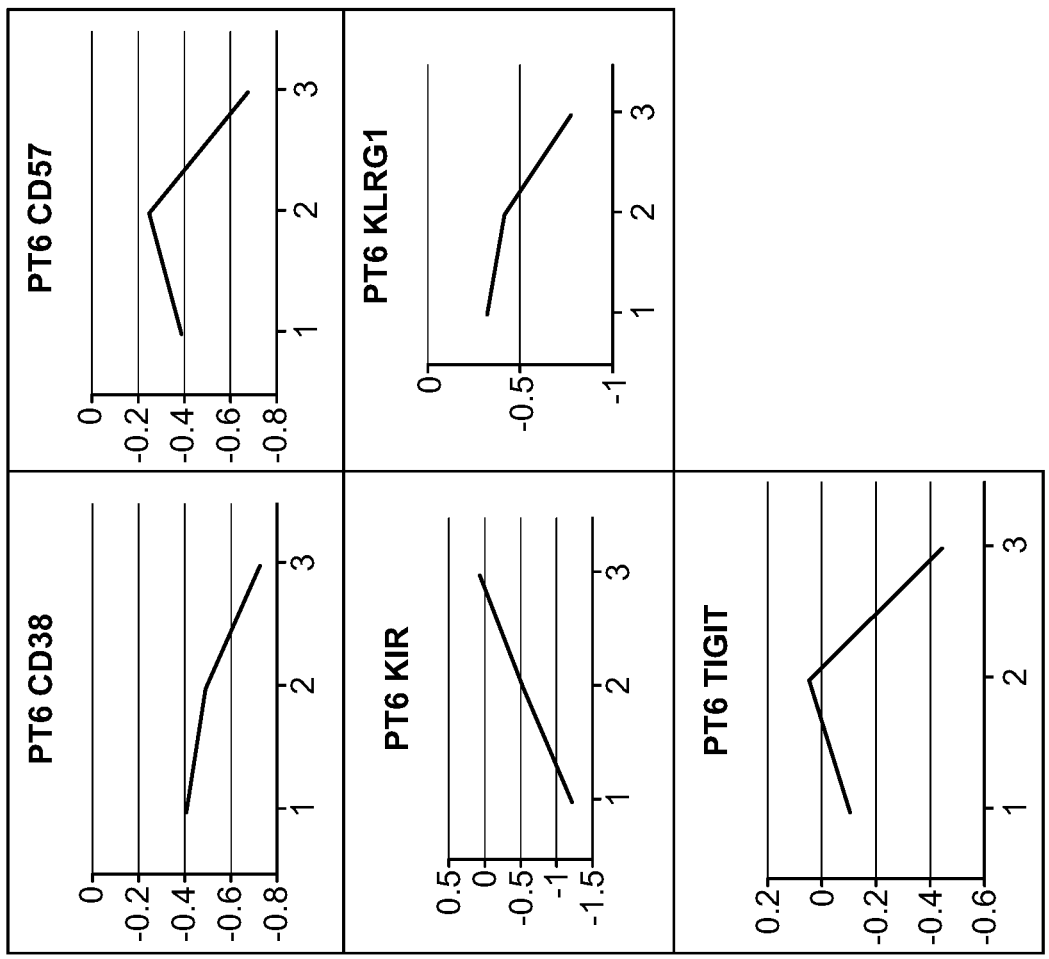

FIG. 15 shows graphs of normalized flow cytometry micro data assaying for degree of expression of the cell surface markers CD16, CD25, CD27, CD38, CD57, CD80, HLADR, IgM, KIR, KLRG1, NK1, NKg2a, and TIGIT in cells from blood samples taken from participants in the pilot study. An assay was performed on expression of SA-β-gal as well in cells from blood samples taken from participants in the pilot study. The graphs in FIG. 15 show micro data for blood samples taken from PT6. Three blood samples were taken from PT6, one before the first plasmapheresis treatment, one before the fourth plasmapheresis treatment, and one before the sixth and last plasmapheresis treatment, and these are the x-values 1, 2, and 3 of each graph.

Figure 16:
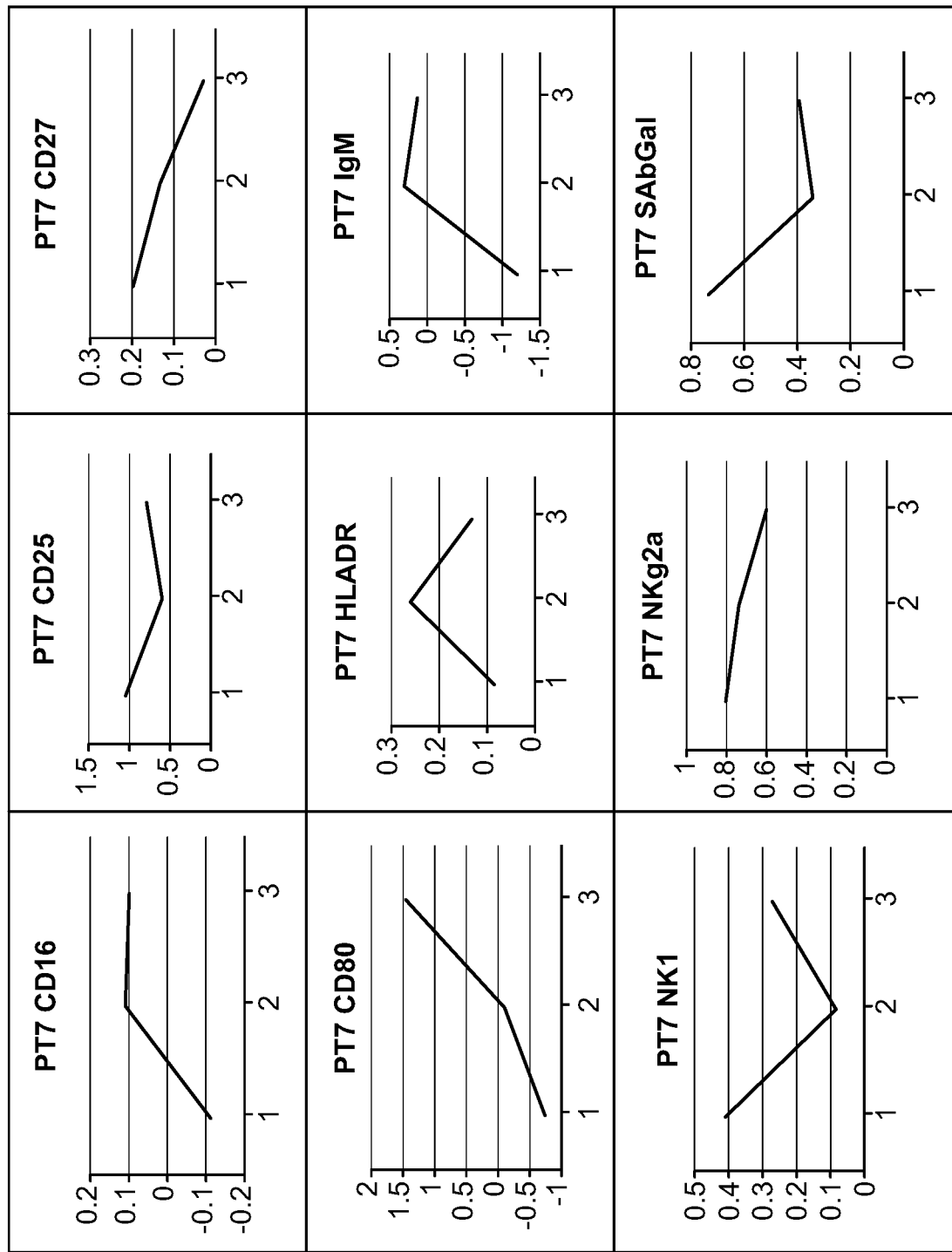
FIG. 16 is a series of graphs of biological aging marker levels measured in the blood of a male subjected to a regimen of six plasmapheresis treatments.
Figure 16:
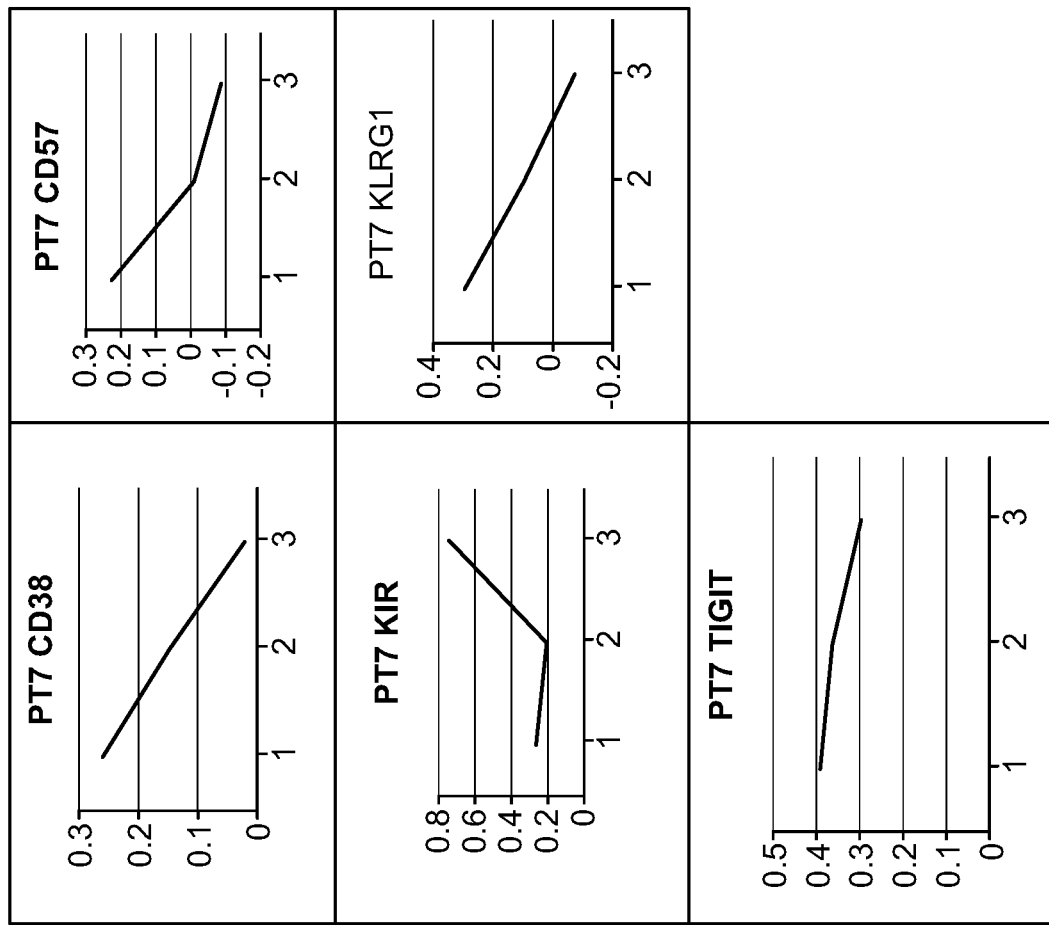

FIG. 16 shows graphs of normalized flow cytometry micro data assaying for degree of expression of the cell surface markers CD16, CD25, CD27, CD38, CD57, CD80, HLADR, IgM, KIR, KLRG1, NK1, NKg2a, and TIGIT in cells from blood samples taken from participants in the pilot study. An assay was performed on expression of SA-β-gal as well in cells from blood samples taken from participants in the pilot study. The graphs in FIG. 16 show micro data for blood samples taken from PT7. Three blood samples were taken from PT7, one before the first plasmapheresis treatment, one before the fourth plasmapheresis treatment, and one before the sixth and last plasmapheresis treatment, and these are the x-values 1, 2, and 3 of each graph.

Figure 17:
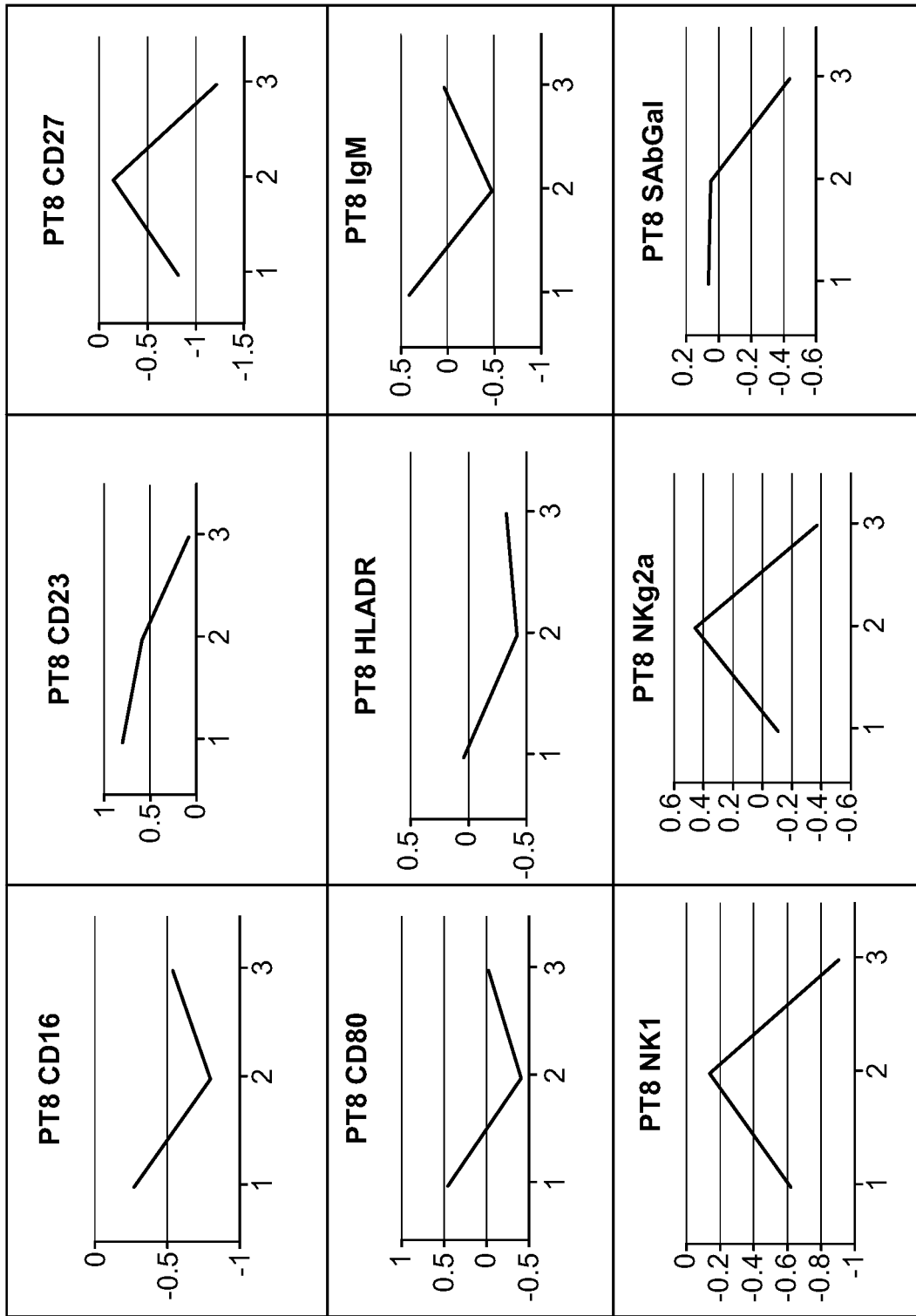
FIG. 17 is a series of graphs of biological aging marker levels measured in the blood of a male subjected to a regimen of six plasmapheresis treatments.
Figure 17:
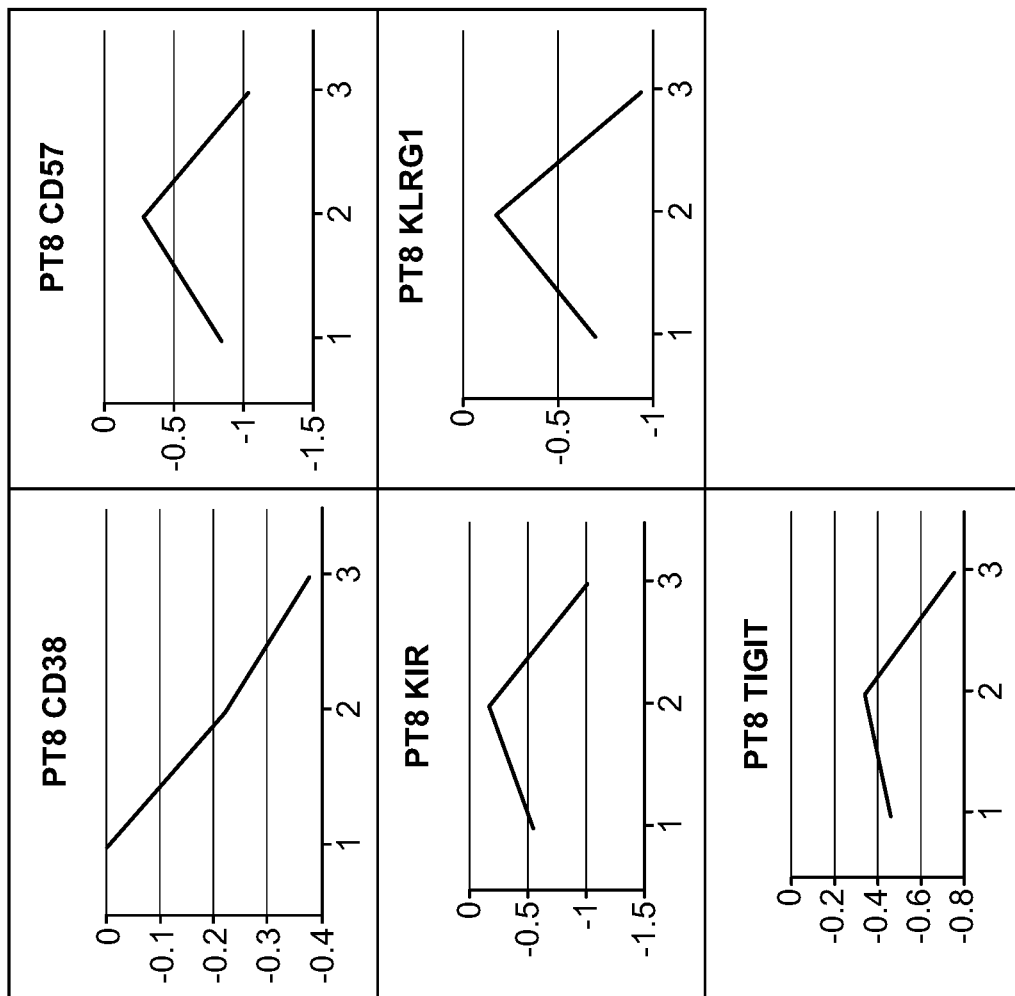

FIG. 17 shows graphs of normalized flow cytometry micro data assaying for degree of expression of the cell surface markers CD16, CD25, CD27, CD38, CD57, CD80, HLADR, IgM, KIR, KLRG1, NK1, NKg2a, and TIGIT in cells from blood samples taken from participants in the pilot study. An assay was performed on expression of SA-β-gal as well in cells from blood samples taken from participants in the pilot study. The graphs in FIG. 17 show micro data for blood samples taken from PT8. Three blood samples were taken from PT8, one before the first plasmapheresis treatment, one before the fourth plasmapheresis treatment, and one before the sixth and last plasmapheresis treatment, and these are the x-values 1, 2, and 3 of each graph.

TABLE IV

| ID | CD16 | CD25 | CD27 | CD38 | CD57 | CD80 | HLADR |
|---|---|---|---|---|---|---|---|
| PT3 | 0.71240857 | 0.04503152 | −0.0305988 | 0.00910674 | −0.064439 | −0.2246972 | 0.13545528 |
| PT4 | 1.1129187 | 0.06767628 | 0.08079247 | 0.41053551 | 0.05358887 | 1.63658564 | 0.5941538 |
| PT5 | −0.2377705 | −0.7618762 | −0.2326512 | −0.3667022 | −0.2180597 | 1.16876294 | −0.5084983 |
| PT6 | 0.40331989 | 0.58625418 | −0.2862214 | −0.3193115 | −0.2878076 | 1.24095402 | 0.32989073 |
| PT7 | 0.211982 | −0.2566571 | −0.1681396 | −0.2390395 | −0.3137011 | 2.2009023 | 0.04759931 |
| PT8 | −0.2686451 | −0.7306268 | −0.3970219 | −0.3786687 | −0.1898519 | −0.4777714 | −0.3679932 |

| ID | IgM* | KIR | KLRG1 | NK1 | NKg2a* | TIGIT | SAbGal |
|---|---|---|---|---|---|---|---|
| PT3 | 0.00069104 | −0.2419516 | −0.0754772 | 0.1607978 | 0.22066851 | 0.02742771 | −0.0782061 |
| PT4 | 1.34452284 | 0.97827381 | −0.1218445 | 0.03809551 | 0.09519207 | 0.42050767 | 0.11329363 |
| PT5 | 0.87019931 | 0.31031164 | −0.1434073 | −0.1634698 | −0.2987369 | −0.4628126 | −0.3486344 |
| PT6 | −0.7027636 | 1.28626122 | −0.4544701 | −0.2493025 | 0.29713981 | −0.3410597 | −0.1158705 |
| PT7 | 1.32938848 | 0.47897551 | −0.3687835 | −0.1381616 | −0.2044997 | −0.0942918 | −0.3409115 |
| PT8 | −0.3768263 | −0.4654095 | −0.2407952 | −0.2823279 | −0.2643162 | −0.2939654 | −0.4999459 |

TABLE IV above is broken into three parts to fit here and shows micro data for the six participants (PT3, PT4, PT5, PT6, PT7, and PT8) for which micro data is shown and described herein in FIGS. 12-17 and their respective accompanying descriptions. More specifically, the numerical data in TABLE IV is the difference (or delta) between the first data point and the last data point for each micro data parameter measured for PT3, PT4, PT5, PT6, PT7, and PT8 who all received six plasmapheresis treatments. That is, for PT3, PT4, PT5, PT6, PT7, and PT8 each number in TABLE IV is the last measured data value (i.e. preceding the sixth plasmapheresis treatment) minus the first measured data value (i.e. preceding the first plasmapheresis treatment). In general, consensus for the cell surface markers is that decreases in values indicate an improvement (i.e. through, at least, indicating a decrease in inflammation) except for the markers IgM and NKg2a which are marked with an asterisk to indicate that some research has indicated that an increase in the values measured for these two markers indicates improvement. Values in TABLE IV that indicate improvement over the course of the plasmapheresis treatments delivered to PT3, PT4, PT5, PT6, PT7, and PT8 that indicate improvement are bolded in TABLE IV. As shown, PT5, PT6, PT7, and PT8 all had improvement in expression of cell surface markers over the majority of markers measured between the first and last blood samples. In addition looking at individual markers, KLRG1 expression decreased in all participants shown in TABLE IV and CD27, CD57, and SAbGal expression decreased in almost all participants in TABLE IV.

General Statements Regarding this Disclosure

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. For example, the methods described herein do not necessarily require the particular order of steps illustrated to achieve the desired result but rather one or more of the steps of a method as described herein may be performed in a different order with respect to the other steps. Moreover, additional steps or operations may be provided or steps or operations may be eliminated to achieve the desired result.

It will be understood by one of ordinary skill in the art that all or a portion of the methods disclosed herein may be embodied in a non-transitory machine readable or accessible medium comprising instructions readable or executable by a processor or processing unit of a computing device or other type of machine.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application.

Reference to a singular item includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth but is intended to cover alternatives, modifications, and equivalents of the variations or embodiments described herein. Further, the scope of the disclosure fully encompasses other variations or embodiments that may become obvious to those skilled in the art in view of this disclosure.

What is claimed is:

1. A method of providing plasmapheresis to an individual in order to improve a health status of the individual, comprising the steps of:
   (a) measuring, before an administration of plasmapheresis, one or more of a strength of the individual, a balance of the individual, a mental status of the individual, and a walking of the individual, thereby generating a pre-treatment health status of the individual;
   (b) administering plasmapheresis to the individual;
   (c) measuring, following step (b), one or more of the strength of the individual, the balance of the individual, the mental status of the individual, and the walking of the individual, thereby generating a post-treatment health status of the individual;
   (d) comparing the post-treatment health status of the individual with the pre-treatment health status of the individual, wherein the comparing the post-treatment health status of the individual with the pre-treatment health status of the individual results in a determination of a quantitative difference between the post-treatment health status of the individual and the pre-treatment health status of the individual; and
   (e) repeating steps (b) through (d) until the quantitative difference between the post-treatment health status of the individual and the pre-treatment health status of the individual is a specific value.

2. The method of claim 1, wherein step (a) occurs within 24 hours of the administering of the plasmapheresis to the individual in step (b).

3. The method of claim 1, wherein the strength of the individual is measured in step (a), step (c), or steps (a) and (c) by measuring a grip strength of the individual.

4. The method of claim 1, wherein the balance of the individual is measured in step (a), step (c), or steps (a) and (c) by having the individual stand on one leg and measuring how long the individual remains standing with one leg raised.

5. The method of claim 1, wherein the mental status is measured in step (a), step (c), or steps (a) and (c) using a survey comprising questions that assess emotional wellbeing.

6. The method of claim 1, wherein the walking of the individual is measured in step (a), step (c), or steps (a) and (c) by having the individual stand from a seated position and walk.

7. The method of claim 1, wherein the plasmapheresis that is administered in step (b) exchanges at least one unit of plasma volume.

8. The method of claim 1, wherein the plasmapheresis that is administered in step (b) is administered over a plurality of treatment sessions.

9. The method of claim 8, wherein two treatment sessions of the plurality of treatment sessions are within 72 hours of each other.

10. The method of claim 1, wherein the plasmapheresis that is administered in step (b) is administered over a single treatment session.

11. The method of claim 1, comprising repeating step (a) before repeating steps (b) through (d).

12. A method of providing plasmapheresis to an individual in order to improve a health status of the individual, comprising the steps of:
   (a) measuring, before an administration of plasmapheresis, one or more of a strength of the individual, a balance of the individual, a mental status of the individual, and a walking of the individual, thereby generating a pre-treatment health status of the individual;
   (b) administering plasmapheresis to the individual;
   (c) measuring, following step (b), one or more of the strength of the individual, the balance of the individual, the mental status of the individual, and the walking of the individual, thereby generating a post-treatment health status of the individual;

(d) comparing the post-treatment health status of the individual with the pre-treatment health status of the individual, wherein the comparing the post-treatment health status of the individual with the pre-treatment health status of the individual results in a determination of a quantitative difference between the post-treatment health status of the individual and the pre-treatment health status of the individual; and (e) repeating steps (b) and (c) until the post-treatment health status of the individual is a specific value.

* * * * *

UNITED STATES PATENT AND TRADEMARK OFFICE
CERTIFICATE OF CORRECTION

| | | |
|---|---|---|
| PATENT NO. | : 12,005,172 B2 | Page 1 of 2 |
| APPLICATION NO. | : 18/204293 | |
| DATED | : June 11, 2024 | |
| INVENTOR(S) | : Dobri Kiprov | |

It is certified that error appears in the above-identified patent and that said Letters Patent is hereby corrected as shown below:

In the Specification

In Column 1, Line 20, delete "cardio vascular" and insert -- cardiovascular --.

In Column 3, Line 3, delete "KTR." and insert -- KIR. --.

In Column 6, Line 15, delete "KTR." and insert -- KIR. --.

In Column 6, Line 56, delete "KTR." and insert -- KIR. --.

In Column 7, Line 22, delete "reasured" and insert -- measured --.

In Column 9, Line 34, delete "corelated" and insert -- correlated --.

In Column 18, Line 39, delete "(3-" and insert -- β- --.

In Column 19, Line 19, delete "C-reative" and insert -- C-reactive --.

In Column 19, Line 19, delete "IL-10," and insert -- IL-1β, --.

In Column 23, Line 44, delete "(TL" and insert -- (IL --.

In Column 23, Line 45, delete "-7" and insert -- -γ --.

In Column 23, Line 46, delete "-7)," and insert -- -γ), --.

In Column 24, Lines 50-51, delete "gamma-glutamyltranserase." and insert -- gamma-glutamyltransferase. --.

Signed and Sealed this
Fourth Day of November, 2025

John A. Squires
*Director of the United States Patent and Trademark Office*

CERTIFICATE OF CORRECTION (continued)
U.S. Pat. No. 12,005,172 B2

In Column 28, Lines 42-43, delete "plasmapheresis," and insert -- Plasmapheresis, --.

In Column 29, Line 50, delete "plasmaphersis" and insert -- plasmapheresis --.

In Column 39, Line 20, delete "macro" and insert -- Macro --.

In Column 39, Line 22, delete "micro" and insert -- Micro --.